US005955318A

United States Patent [19]
Simons et al.

[11] Patent Number: 5,955,318
[45] Date of Patent: *Sep. 21, 1999

[54] REAGENTS AND METHODS USEFUL FOR CONTROLLING THE TRANSLATION OF HEPATITIS GBV PROTEINS

[75] Inventors: John N. Simons, Grayslake; Suresh M. Desai, Libertyville; Isa K. Mushahwar, Grayslake, all of Ill.

[73] Assignee: Abbott Laboratories, Abbott Park, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/639,857

[22] Filed: Apr. 19, 1996

Related U.S. Application Data

[63] Continuation-in-part of application No. 08/580,038, Dec. 21, 1995
[60] Provisional application No. 60/002,265, Aug. 14, 1995.
[51] Int. Cl.[6] .......................... C12P 21/02; C07H 21/02; C07H 21/04
[52] U.S. Cl. ...................... 435/71.1; 435/69.1; 536/23.1; 536/24.5; 935/36
[58] Field of Search ................................ 536/23.1, 24.5; 514/44; 935/36; 435/71.1, 69.1

[56] References Cited

U.S. PATENT DOCUMENTS

| | | | |
|---|---|---|---|
| 4,743,535 | 5/1988 | Carrico | 435/6 |
| 4,876,187 | 10/1989 | Duck et al. | 435/6 |
| 5,275,947 | 1/1994 | Arima et al. | |
| 5,399,346 | 3/1995 | Anderson et al. | 424/93.21 |
| 5,527,669 | 6/1996 | Resnick et al. | 435/5 |
| 5,576,302 | 11/1996 | Cook et al. | 514/44 |

FOREIGN PATENT DOCUMENTS

| | | |
|---|---|---|
| 0318216 | 5/1989 | European Pat. Off. . |
| 9000597 | 1/1990 | WIPO . |
| 9408002 | 4/1994 | WIPO . |
| 9418217 | 8/1994 | WIPO . |
| 9532290 | 11/1995 | WIPO . |
| 9532291 | 11/1995 | WIPO . |
| 9532292 | 11/1995 | WIPO . |
| 9506266 | 5/1996 | WIPO . |

OTHER PUBLICATIONS

P. Yarbough et al., Hepatitis E Virus: Identification of Type–Common Epitopes, *Journal of Virology* vol. 65 No. 11: pp. 5790–5797 (1991).
H. Alter et al., Detection of Antibody to Hepatitis C Virus in Prospectively Followed Transfusion Recipients with Acute and Chronic Non–A, Non–B Hepatitis, *The New England Journal of Medicine* vol. 321 No. 22: pp. 1494–1500 (1989).
M. Alter et al., Risk Factors for Acute Non–A, Non–B Hepatitis in the United States and Association With Hepatitis C Virus Infection, *JAMA* vol. 264 No. 17: pp. 2231–2235 (1990).
J. Dienstag, Hepatitis Non–A, Non–B: C at Last, *Gastroenterology* vol. 99 No. 4: pp. 1177–1180 (1990).
G. Reyes et al., Isolation of a cDNA from the Virus Responsible for Enterically Transmitted Non–A, Non–B Hepatitis, *Science* vol. 247 : pp. 1335–1339 (1990).
G. Kuo et al., An Assay for Circulating Antibodies to a Major Etiologic Virus of Human Non–A, Non–B Hepatitis, *Science* vol. 244 : pp. 362–364 (1989).
A. Weiner et al., Detection of hepatitis C viral sequences in non–A, non–B hepatitis, *The Lancet* vol. 335: pp. 1–3 (1990).
G. Schlauder et al., Viraemia in Egyptian children with hepatitis E virus infection, *The Lancet* vol. 341: p. 378 (1993).
N. Lisitsyn et al., Cloning the Differences Between Two Complex Genomes, *Science* vol. 259: pp. 946–951 (1993).
V. Thiers et al., Post–transfusional anti–HCV–negative non–A non–B hepatitis (II) serological and polymerase chain reaction analysis for hepatitis C and hepatitis B viruses, *Journal of Hepatology* vol. 18: pp. 34–39 (1993).
Hepatitis C virus upstanding, *The Lancet* vol. 335: pp. 1431–1432 (1990).
W. Parks et al., Attempted Isolation of Hepatitis Viruses in Marmosets, *The Journal of Infectious Diseases* vol. 120 No. 5: 539–547 (1969).
A. Holmes et al., Specific Neutralization of Human Hepatitis Type A in Marmoset Monkeys, *Nature* vol. 243: pp. 419–420 (1973).
P. Provost et al., Physical, Chemical and Morphologic Dimensions of Human Hepatitis A Virus Strain CR326 (38578), *Proceeding of the Society for Experimental Biology and Medicine* vol. 148: pp. 532–539 (1975).
Q. Choo et al., Isolation of a cDNA Clone Derived from a Blood–Borne Non–A, Non–B Viral Hepatitis Genome, *Science* vol. 244: pp. 359–361 (1989).
J. Almeida et al., Morphology of the GB hepatitis agent, *Nature* vol. 261: pp. 608–609 (1976).
F. Deinhardt et al., Studies on the Transmission of Human Viral Heptitis to Marmoset Monkeys, *Journal of Experimental Medicine* vol. 125: pp. 673–688, Plate 81–86 (1966).
J. Dienstag, Non–A, Non–B Hepatitis. II. Experimental Transmission, Putative Virus Agents and Markers, and Prevention, *Gastroenterology* vol. 85 No. 3: pp. 743–768 (1983).
F. Hollinger et al., Transfusion–Transmitted Viruses Study: Experimental Evidence for Two Non–A, Non–B Hepatitis Agents, *Journal of Infectious Diseases* vol. 142 No. 3: pp. 400–407 ( 1980).
D. Bradley, Transmission, Etiology, and Pathogenesis of Viral Hepatitis Non–A, Non–B in Non–Human Primates, *Advances in Hepatitis Research*: pp. 268–280 (1984).

(List continued on next page.)

*Primary Examiner*—Stephanie W. Zitomer
*Attorney, Agent, or Firm*—Priscilla E. Porembski; Dianne Casuto

[57] ABSTRACT

Reagents and composition for controlling the translation of hepatitis GB virus (HGBV)-A, -B or -C peptides from viral nucleic acid. These reagents and methods comprise control elements of the 5' NTR region of the HGBV-A, -B, or -C viral genome.

5 Claims, 13 Drawing Sheets

OTHER PUBLICATIONS

F. Deinhardt et al., Hepatitis in marmosets, *The American Journal of the Medical Sciences* vol. 270: pp. 73–80 (1975).

S. Kalter, Comparison of Infectivity of Human Non–A/Non–B Hepatitis and the GB Hepatitis Agent in Marmosets, *Viral and Immunological Diseases in Nonhuman Primates*;: pp. 221–224 (1983).

E. Tabor et al., Transmission of Human Non–A, Non–B Hepatitis to Chimpanzees Following Failure to Transmit GB Agent Hepatitis, *Journal of Medical Virology:* pp. 103–108 (1980).

D. Bradley et al., Posttransfusion Non–A, Non–B Hepatitis: Physicochemical Properties of Two Distinct Agents, *The Journal of Infectious Diseases* vol. 148 No. 2: pp. 254–265 (1983).

J. Dienstag, Virus–like particles and GB agent hepatitis, *Nature* vol. 264: pp. 260–261 (1976).

P. Karayiannis et al., Studies of GB Hepatitis Agent in Tamarins, *Hepatology* vol. 9 No. 2: pp. 186–192 (1989).

J. Melnick, Classification of Hepatitis A Virus as Enterovirus Type 72 and of Hepatitis B Virus as Hepadnavirus Type 1, *Intervirology* vol. 18: pp. 105–106 (1982).

W. Parks et al., Characterization of Marmoset Hepatitis Virus, *The Journal of Infectious Diseases* vol. 120 No. 5: pp. 548–559 (1969).

S. Feinstone et al., Hepatitis A: Detection by Immune Electron Microscopy of a Viruslike Antigen Associated with Acute Illness, *Science* vol. 182: pp. 1026–1028 (1973).

E. Tabor et al., Lack of Susceptibility of Marmosets to Human Non–A, Non–B Hepatitis, *The Journal of Infectious Diseases* vol. 140 No. 5: pp. 794–797 (1979).

E. Fagan et al., Toga Virus–Like Particles in Acute Liver Failure Attributed to Sporadic Non–A, Non–B Hepatitis and Recurrence After Liver Transplantation, *Journal of Medical Virology* vol. 38: pp. 71–77 (1992).

J. Dienstag, Virus particles in marmoset hepatitis, *Nature* vol. 267: pp. 729–730 (1977).

F. Dienhardt et al., Hepatitis in Marmosets, *The Journal of Infectious Diseases* vol. 121 No. 3: pp. 351–354 (1970).

F. Dienhardt et al., The Mythology of Various Hepatitis A Virus Isolates, *International Symposium on Viral Hepatitis:* pp. 390–404 (1975).

M. Alter et al., The Natural History of Community–Acquired Hepatitis C in the United States, *The New England Journal of Medicine* vol. 327 No. 27: pp. 1899–1905 (1992).

R. Gibbs, Polymerase chain reaction techniques, *Analytical Biotechnology:* pp. 69–75 (1991).

S. Friedman et al., The core element of the EcoRII methylase as defined by protease digestion and deletion analysis, *Nucleic Acids Research* vol. 19 No. 19: pp. 5403–5408 (1991).

A. Rosenthal et al., Genomic walking and sequencing by oligo–cassette mediated polymerase chain reaction, *Nucleic Acids Research* vol. 18 No. 10: pp. 3095–3096 (1990).

A. Akowitz, Protected endogenous retroviral sequences copurify with infectivity in experimental Creutzfeldt–Jakob disease, *Archives of Virology* vol. 130: pp. 301–316 (1993).

Non–A, Non–B?, *The Lancet* vol. 2: pp. 64–65 (1975).

F. Hollinger, Non–A, Non–B Hepatitis Viruses, *Virology* : pp. 2239–2273 (1990).

J. Dienstag, Non–A, Non–B Hepatitis I. Recognition, Epidemiology, and Clinical Features, *Gastroenterology* vol. 85 No. 2: pp. 439–462 (1983).

J. Strauss et al., Structure and Function of the Flavivirus and Pestivirus Genomes, *Viral Hepatitis and Liver Disease*: pp. 333–344 (1990).

H. Alter et al., Posttransfusion Hepatitis After Exclusion of Commercial and Hepatitis–B Antigen–Positive Donors, *Annals of Internal Medicine* vol. 77 No. 5: pp. 691–699 (1972).

H. Alter et al., Clinical and Serological Analysis of Transfusion–Associated Hepatitis, *The Lancet:* pp. 838–841 (1975).

S. Feinstone et al., Transfusion–Associated Hepatitis Not Due To Viral Hepatitis Type A or B, *The New England Journal of Medicine* vol. 292 No. 15: pp. 767–770 (1975).

J. Simons et al., Indentification of two flavivirus–like genomes in the GB Hepatitis agent, *Proc. Natl. Acad. Sci. USA* vol. 92: pp. 3401–3405 (1995).

J. Simons et al., Isolation of novel virus–like sequences associated with human hepatitis, *Nature Medicine* vol. 1 No. 6: pp. 564–568 (1995).

G. Schlauder et al., Molecular and Serologic Analysis in the Transmission of the GB Hepatitis Agents, *Journal of Medical Virology* vol. 46: pp. 81–90 (1995).

M. Yoshiba et al., Detection of the GBV–C hepatitis virus genome in serum from patients with fulminant hepatitis of unknown aetiology, *The Lancet* vol. 346: pp. 1131–1132 (1995).

J. Linnen et al., Molecular Cloning and Disease Association of Hepatitis G Virus: A Transfusion–Transmissible Agent, *Science* vol. 271: pp. 505–508 (1996).

A. Zuckerman, The new GB hepatitis viruses, *The Lancet* vol. 345: pp. 1453–1455 (1995).

L. Altman, Three Newly Discovered Viruses May Cause Unexplained Hepatitis, *The New York Times Medical Science* , Apr. 11, 1995.

L. Altman, Newly Found Viruses May Cause Hepatitis, *The New York Times Medical Science,* Apr. 10, 1995.

T. Leary et al., Sequence and Genomic Organization of GBV–C: A novel Member of the Flaviviridae Associated With Human Non–A–E Hepetitis, *Journal of Medical Virology* vol. 48: pp. 80–87 (1996).

G. Caetano–Anolles et al., DNA Amplification Fingerprinting Using Arbitrary Oligonucleotide Primers, *Applied Biochemistry and Biotechnology* vol. 42: pp. 189–200 (1993).

B. Bassam, DNA amplification fingerprinting of bacteria, *Applied Microbiology and Biotechnology* vol. 38: pp. 70–76 (1992).

G. Caetano–Anolles et al., DNA Amplification Fingerprinting Using Very Short Arbitrary Oligonucleotide Primers, *Biotechnology* vol. 9: pp. 553–557 (1991).

J. Welsh et al., Fingerprinting genomes using PCR with arbitrary primers*, *Nucleic Acids Research* vol. 18 No. 24: pp. 7213–7218 (1990).

J. Welsh et al., Arbitrarily primed PCR fingerprinting of RNA, *Nucleic Acids Research* vol. 20 No. 19: pp. 4965–4970 (1992).

J. Williams et al., DNA polymorphisms amplified by arbitrary primers are useful as genetic markers, *Nucleic Acids Research* vol. 18 No. 22: pp. 6531–6535 (1990).

P. Liang et al., Differential Display of Eukaryotic Messenger RNA by Means of the Polymerase Chain Reaction, *Science* vol. 257: pp. 967–971 (1992).

P. Liang et al., Distribution and cloning of eukaryotic mRNAs by means of differential display: refinements and optimization, *Nucleic Acids Research* vol. 21 No. 14: pp. 3269–3275 (1993).

Brown, *Washington Post,* Dec. 8, 1995, pp. 1 & A22.

Gura, Science 270: 575–577 (Oct. 27, 1995).

A. Muerhoff et al., *Journal of Virology,* 69 (9), 5621–5630 (1995).

Choo et al., *Proc. Natl. Acad. Sci. USA,* vol. 88, pp. 2451–22455 (1991).

Okamoto et al., "Polyprotein precursor –hepatitis C virus", EMBL Sequence Accession No. S40770, Submitted March 1992.

Okamoto et al., *Virology,* vol. 188, pp. 331–341 (1992).

M. J. Slater et al., *Exp. Opin. Ther. Patents,* vol. 6 (8): 739–746 (1996).

S. Chan et al., Journal of General Virology, 73: 1131–1141 (1992).

R. Koshy et al., Trends in Biotechnology, 14(10): 364–369 (1996).

| pCAT/--/Luc | Luc-A | Luc-P |
|---|---|---|
| A15-705 | 10.2 | 25.2 |
| A15-657 | 1.13 | 14.8 |
| A15-596 | 10.3 | 13.8 |
| A657-15 | 0.13 | 6.37 |
| C1-629 | 4.09 | 15.4 |
| C1-596 | 0.80 | 12.4 |
| C1-526 | 13.5 | 14.7 |
| C596-1 | 2.02 | 5.75 |
| HCV39-377 | 546 | 403 |
| HCV39-345 | 270 | 205 |

FIG.7B

SEQUENCE LISTING (1) GENERAL INFORMATION:

(iii) NUMBER OF SEQUENCES:32

(2) INFORMATION FOR SEQ ID NO:1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

CCACAAACAC TCCAGTTTGT TAC                                      23

(2) INFORMATION FOR SEQ ID NO:2:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

GCTCTAGACA TGTGCTACGG TCTACGAG                                  28

(2) INFORMATION FOR SEQ ID NO:3:

(i) SEQUENCE CHARACTERISTICS:
      (A) LENGTH: 9126 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

| | | | | | |
|---|---|---|---|---|---|
| CCCCCCCCCC | GGCACTGGGT | GCAAGCCCCA | GAAACCGACG | CCTACTGAAG | TAGACGTAA 60 |
| GGCCCCGCGC | CGAACCGGCG | ACCGGCCAAA | AGGTGGTGGA | TGGGTGATGA | CAGGGTTG 120 |
| AGGTCGTAAA | TCCCGGTCAT | CCTGGTAGCC | ACTATAGGTG | GGTCTTAAGG | GGAGGCTA 180 |
| GTCCCTCTTG | CGCATATGGA | GGAAAAGCGC | ACGGTCCACA | GGTGTTGGTC | CTACCGGT 240 |
| AATAAGGACC | CGGCGCTAGG | CACGCCGTTA | AACCGAGCCC | GTTACTCCCC | TGGGCAAA 300 |
| ACGCCCACGT | ACGGTCCACG | TCGCCCTTCA | ATGTCTCTCT | TGACCAATAG | GCGTAGCC 360 |
| CGAGTTGACA | AGGACCAGTG | GGGGCCGGGC | GGGAGGGGGA | AGGACCCCCA | CCGCTGCC 420 |
| TCCCGGGGAG | GCGGGAAATG | CATGGGGCCA | CCCAGCTCCG | CGGCGGCCTA | CAGCCGGG 480 |
| AGCCCAAGAA | CCTTCGGGTG | AGGGCGGGTG | GCATTTCTTT | TCCTATACCG | ATCATGGC 540 |
| TCCTTCTGCT | CCTACTCGTG | GTGGAGGCCG | GGCTATTTT | AGCCCCGGCC | ACCCATGC 600 |
| GTAGCGCGAA | AGGGCAATAT | TTBCTCACAA | ACTGTTGCGC | CCTGGAGGAC | ATAGGCTT 660 |
| GCCTGGAGGG | CGGATGCCTG | GTGGCTCTGG | GGTGCACCAT | TTGCACCGAC | CGCTGCTG 720 |
| CACTGTATCA | GGCGGGTTTG | GCCGTGCGGC | CCGGCAAGTC | CGCCGCCCAG | TTGGTGGG 780 |
| AACTCGGTAG | TCTCTACGGG | CCCTTGTCGG | TCTCGGCTTA | TGTGGCCGGG | ATCCTGGG 840 |
| TTGGGGAGGT | CTACTCGGGG | GTCCTCACCG | TCGGGTGGC | GTTGACGCGC | AGGGTCTA 900 |
| CGGTCCCGAA | CCTGACGTGT | GCAGTAGAGT | GTGAGTTGAA | GTGGGAAAGT | GAGTTTTG 960 |
| GATGGACTGA | ACAGCTGGCC | TCAAACTACT | GGATTCTGGA | ATACCTCTGG | AAGGTGC 1020 |
| TCGACTTTTG | GCGGGGAGTG | ATGAGCCTTT | CTCCTCTCTT | GGTGTGCGTG | GCGGCCC 1080 |
| TCCTGCTGGA | GCAGCGTATT | GTCATGGTCT | TCCTCCTGGT | CACTATGGCG | GGCATGT 1140 |
| AAGGCGCGCC | CGCCTCAGTG | TTGGGGTCAC | GGCCTTTCGA | GGCCGGGCTG | ACTTGGC 1200 |
| CTTGTTCTTG | CAGGTCGAAC | GGGTCCCGCG | CGCCGACAGG | GGAGAGGGTT | TGGGAAC 1260 |
| GGAACGTCAC | ACTTTTGTGT | GACTGCCCCA | ACGGTCCTTG | GGTGTGGGTC | CCGGCCC 1320 |
| GCCAGGCAAT | CGGATGGGGC | GACCCTATCA | CTCATTGGAG | CCACGGACGA | AATCAGT 1380 |
| CCCTTTCTTG | TCCCCAATTT | GTCTACGGCG | CCGTTTCAGT | GACCTGCGTG | TGGGGTT 1440 |
| TGTCTTGGTT | TGCTTCCACT | GGGGGTCGCG | ACTCCAAGGT | TGATGTGTGG | AGTTTGG 1500 |
| CAGTTGGCTC | TGCCAGCTGT | ACCATAGCCG | CACTGGGATC | TTCGGATCGC | GACACAG 1560 |
| TTGAGCTCTC | CGAATGGGGA | ATCCCCTGCG | CCACTTGTAT | CCTGGACAGG | CGGCCTG 1620 |
| CGTGTGGCAC | CTGTGTGAGG | GACTGCTGGC | CCGAGACCGG | GTCGGTACGT | TTCCCAT 1680 |
| ACAGGTGTGG | CGCGGGACCG | AGGCTGACCA | GAGACCTTGA | GGCTGTGCCC | TTCGTCA 1740 |
| GGACAACTCC | CTTCACCATA | AGGGGCCCC | TGGGCAACCA | GGGGCGAGGC | GACCCGG 1800 |
| GGTCGCCCTT | GGGTTTTGGG | TCCTACACCA | TGACCAAGAT | CCGAGACTCC | TTACACT 1860 |
| TGAAATGTCC | CACCCCAGCC | ATTGAGCCTC | CCACCGGAAC | GTTTGGGATC | TTCCCAG 1920 |
| TCCCCCCCCT | TAACAACTGC | ATGCTTCTCG | GCACTGAGGT | GTCAGAGGTA | TTGGGTG 1980 |
| CGGGCCTCAC | TGGGGGGTTT | TACGAACCTC | TGGTGCGGCG | GTGTTCAGAG | CTGATGG 2040 |
| GGCGGAATCC | GGTCTGCCCG | GGGTTTGCAT | GGCTCTCTTC | GGGACGGCCT | GATGGGT 2100 |
| TACATGTACA | GGGCCACTTG | CAGGAGGTGG | ATGCGGGCAA | CTTCATTCCG | CCCCCAC 2160 |

```
GGTTGCTCTT GGACTTTGTA TTTGTCCTGT CATACCTGAT GAAGCTGGCA GAGGCAC       2220
TGGTCCCGCT GATCCTCCTC CTGCTATGGT GGTGGGTGAA CCAGTTGGCG GTCCTTG       2280
TGSCGGCTGC KCRCGCCGCC GTGGCTGGAG AGGTGTTTGC GGGCCCTGCC TTGTCCT       2340
GTCTGGGCCT ACCCTTCGTG AGTATGATCC TGGGGCTAGC AAACCTGGTG TTGTACT       2400
GCTGGATGGG TCCTCAACGC CTGATGTTCC TCGTGTTGTG GAAGCTCGCT CGGGGGG       2460
TCCCGCTGGC ATTACTGATG GGGATTTCCG CCACTCGCGG CCGCACCTCT GTGCTTG       2520
CCGAATTCTG CTTTGATGTC ACCTTTGAAG TGGACACGTC AGTCTTGGGT TGGGTGG       2580
CTAGTGTGGT GGCTTGGGCC ATAGCGCTCC TGAGCTCTAT GAGCGCGGGG GGGTGGA       2640
ACAAAGCCAT AATCTATAGG ACGTGGTGTA AAGGGTACCA GGCYCTTCGC CAGCGCG       2700
TGCGTAGCCC CCTCGGGGAG GGGCGGCCCA CCAAGCCGCT GACGATAGCC TGGCGTC       2760
CCTCTTACAT CTGGCCGGAC GCTGTGATGT TGGTGGTTGT GGCCATGGTC CTCCTCT       2820
GCCTTTTCGA CGCGCTCGAT TGGGCCTTGG AGGAGCTCCT TGTGTCGCGG CCTTCGT       2880
GTCGTTTGGC AAGGGTGGTG GAGTGTTGTG TGATGGCGGG CGAGAAGGCC ACTACCG       2940
GGCTTGTGTC CAAGATGTGC GCGAGAGGGG CCTACCTGTT TGACCACATG GGGTCGT       3000
CGCGCGCGGT CAAGGAGCGC TTGCTGGAGT GGGACGCGGC TTTGGAGMCC CTGTCAT       3060
CTAGGACGGA CTGCCGCATC ATACGAGACG CCGCCAGGAC TCTGAGCTGC GGCCAAT       3120
TCATGGGCTT GCCCGTGGTG GCTAGGCGCG GCGATGAGGT CCTGGTTGGG GTCTTTC       3180
ATGTGAACCA CTTGCCTCCG GGGTTTGYTC CTACAGCGCC TGTTGTCATC CGTCGGT       3240
GAAAGGGCTT CCTCGGGGTC ACTAAGGCTG CCTTGACTGG TCGGGATCCT GACTTAC       3300
CAGGAAACGT CATGGTTTTG GGGACGGCTA CCTCGCGCAG CATGGGAACG TGCTTAA       3360
GGTTGCTGTT CACGACATTC CATGGGGCTT CTTCCCGAAC CATTGCGACA CCTGTGG       3420
CCCTTAACCC AAGGTGGTGG TCGGCCAGTG ATGACGTCAC GGTCTATCCC CTCCCCG       3480
GAGCTAACTC GTTGGTTCCC TGCTCGTGTC AGGCTGAGTC CTGTTGGGTC ATYCGAT       3540
ATGGGGCTCT TTGCCATGGC TTGAGCAAGG GGGACAAGGT AGAACTGGAC GTGGCCA       3600
AGGTTGCTGA CTTTCGTGGG TCGTCTGGGT CTCCTGTCCT ATGCGACGAG GGGCACG       3660
TAGGAATGCT CGTGTCCGTC CTTCATTCGG GGGGAGGGT GACCGCGGCT CGATTCA       3720
GGCCGTGGAC CCAAGTCCCA ACAGACGCCA AGACTACCAC TGAGCCACCC CCGGTGC       3780
CTAAAGGGGT TTTCAAAGAG GCTCCTCTTT TCATGCCAAC AGGGGCGGGG AAAAGCA       3840
GCGTCCCTTT GGAATATGGA AACATGGGGC ACAAGGTCCT GCTTCTCAAC CCGTCGG       3900
CCACTGTGAG GGCCATGGGC CCTTACATGG AGAAGCTGGC GGGGAAACAT CCTAGCA       3960
TCTGTGGACA CGACACAACA GCTTTCACAC GGATCACGGA CTCTCCATTG ACGTACT       4020
CCTATGGAG GTTTCTGGCC AACCCGAGGC AGATGCTGAG GGGAGTTTCC GTGGTCA       4080
GTGATGAGTG CCACAGTCAT GACTCAACTG TGTTGCTGGG TATAGGCAGG GGCAGGG       4140
TGGCGCGGGG GTGTGGAGTG CAATTAGTGC TCTACGCTAC TGCGACTCCC CCGGGCT       4200
CTATGACTCA GCATCCATCC ATAATTGAGA CAAAGCTGGA CGTCGGTGAG ATCCCCT       4260
ATGGGCATGG TATCCCCCTC GAGCGTATGA GGACTGGTCG CCACCTTGTA TTCTGCC       4320
CCAAGGCGGA GTGCGAGAGA TTGGCCGGCC AGTTCTCCGC GCGGGGGGTT AATGCCA       4380
CCTATTATAG GGGTAAGGAC AGTTCCATCA TCAAAGACGG AGACCTGGTG GTTTGTG       4440
CAGACGCGCT CTCTACCGGG TACACAGGAA ACTTCGATTC TGTCACCGAC TGTGGGT       4500
TGGTGGAGGA GGTCGTTGAG GTGACCCTTG ATCCCACCAT TACCATTTCC TTGCGGA       4560
```

-continued

| | |
|---|---|
| TCCCTGCTTC GGCTGAATTG TCGATGCAGC GGCGCGGACG CACGGGGAGA GGTCGGT | 4620 |
| GCCGCTACTA CTACGCTGGG GTCGGTAAGG CTCCCGCGGG GGTGGTGCGG TCTGGTC | 4680 |
| TCTGGTCGGC AGTGGAAGCT GGAGTGACCT GGTATGGAAT GGAACCTGAC TTGACAG | 4740 |
| ACCTTCTGAG ACTTTACGAC GACTGCCCTT ACACCGCAGC CGTCGCAGCT GACATTG | 4800 |
| AAGCCGCGGT GTTCTTTGCG GGCCTCGCGC CCCTCAGGAT GCATCCCGAT GTTAGCT | 4860 |
| CAAAAGTTCG CGGCGTCAAT TGGCCCCTCC TGGTGGGTGT TCAGCGGACG ATGTGTC | 4920 |
| AAACACTGTC TCCCGGCCCG TCGGACGACC CTCAGTGGGC AGGTCTGAAA GGCCCGA | 4980 |
| CTGCCCCACT ACTGCTGAGG TGGGGCAATG ATTTGCCATC AAAAGTGGCC GGCCACC | 5040 |
| TAGTTGACGA TCTGGTCCGT CGGCTCGGTG TGGCGGAGGG ATACGTGCGC TGTGATG | 5100 |
| GRCCCATCCT CATGGTGGGC TTGGCCATAG CGGGCGGCAT GATCTACGCC TCTTACA | 5160 |
| GGTCGCTAGT GGTGGTAACA GACTGGAATG TGAAGGGAGG TGGCAATCCC CTTTATA | 5220 |
| GTGGTGACCA GGCCACCCCT CAACCCGTGG TGCAGGTCCC CCCGGTAGAC CATCGGC | 5280 |
| GGGGGGAGTC TGCGCCAGCG GATGCCAAGA CAGTGACAGA TGCGGTGGCA GCCATCC | 5340 |
| TGAACTGCGA TTGGTCTGTG ATGACCCTGT CGATCGGGGA AGTCCTCACC TTGGCTC | 5400 |
| CTAAGACAGC CGAGGCCTAC GCAGCTACTT CCAGGTGGCT CGCTGGCTGC TACACGG | 5460 |
| CGCGGGCCGT CCCCACTGTA TCAATTGTTG ACAAGCTCTT CGCCGGGGGT TGGGCCG | 5520 |
| TGGTGGGTCA CTGTCACAGC GTCATTGCTG CGGTGGTGGC TGCCTATGGG GTTTCTC | 5580 |
| GTCCTCCACT GGCCGCGGCG GCATCCTACC TCATGGGGTT GGGCGTCGGA GGCAACG | 5640 |
| AGGCGCGCTT GGCTTCAGCT CTTCTACTGG GGGCTGCTGG TACGGCTCTG GGGACCC | 5700 |
| TCGTGGGACT CACCATGGCG GGGGCCTTCA TGGGCGGTGC CAGCGTGTCC CCCTCCC | 5760 |
| TCACTGTCCT ACTTGGGGCT GTGGGAGGTT GGGAGGGCGT TGTCAACGCT GCCAGTC | 5820 |
| TCTTCGACTT CATGGCTGGG AAACTTTCAA CAGAAGACCT TTGGTATGCC ATCCCGG | 5880 |
| TCACTAGTCC TGGRGCGGGC CTCGCGGGGA TTGCCCTTGG TCTGGTTTTG TACTCAG | 5940 |
| ACAACTCTGG CACTACCACA TGGCTGAACC GTCTGCTGAC GACGTTGCCA CGGTCAT | 6000 |
| GCATACCCGA CAGCTACTTC AACAGGCTG ACTACTGCGA CAAGGTCTCG GCAATGC | 6060 |
| GCCGCCTGAG CCTTACTCGC ACCGTGGTGG CCCTGGTCAA CAGGGAGCCT AAGGTGG | 6120 |
| AGGTCCAGGT GGGGTACGTC TGGGATCTGT GGGAGTGGGT AATGCGCCAG GTGCGCA | 6180 |
| TGATGTCTAG ACTCCGGGCC CTCTGCCCTG TGGTGTCACT CCCCTTGTGG CACCGCG | 6240 |
| AGGGGTGGTC CGGTGAATGG CTTCTCGATG GCACGTGGA GAGTCGTTGT CTGTGCG | 6300 |
| GTGTAATCAC CGGCGACGTC CTCAATGGGC AACTCAAAGA TCCAGTTTAC TCTACCA | 6360 |
| TGTGCAGGCA CTACTGGATG GGAACTGTGC CGGTCAACAT GCTGGGCTAC GGGGAAA | 6420 |
| CACCTCTTCT CGCCTCTGAC ACCCCGAAGG TGGTACCCTT CGGGACGTCG GGGTGGG | 6480 |
| AGGTGGTGGT GACCCCTACC CACGTGGTGA TCAGGCGCAC GTCCTGTTAC AAACTGC | 6540 |
| GCCAGCAAAT TCTTTCAGCA GCTGTAGCTG AGCCCTACTA CGTTGATGGC ATTCCGG | 6600 |
| CTTGGGAGGC TGACGCGAGA GCGCCGGCCA TGGTCTACGG TCCGGGCCAA AGTGTTA | 6660 |
| TTGATGGGGA GCGCTACACC CTTCCGCACC AGTTGCGGAT GCGGAATGTG GCGCCCT | 6720 |
| AGGTTTCATC CGAGGTCAGC ATCGAGATCG GGACGGAGAC TGAAGACTCA GAACTGA | 6780 |
| AGGCCGATTT GCCACCAGCG GCTGCTGCCC TCCAAGCGAT AGAGAATGCT GCGAGAA | 6840 |
| TCGAACCGCA CATCGATGTC AYCATGGAGG ATTGCAGTAC ACCCTCTCTC TGTGGTA | 6900 |
| GCCGAGAGAT GCCTGTGTGG GGAGAAGACA TACCCCGCAC TCCATCGCCT GCACTTA | 6960 |

```
CGGTTACGGA GAGCAGCTCA GATGAGAAGA CCCTGTCGGT GACCTCCTCG CAGGAGG        7020

CCCCGTCCTC AGACTCATTT GAAGTCATCC AAGAGTCTGA TACTGCTGAA TCAGAGG        7080

GCGTCTTCAA CGTGGCTCTT TCCGTACTAA AAGCATTATT TCCACAGAGC GTTGCCA        7140

GAAAGCTAAC GGTTAAGATG TCTTGCTGTG TTGAGAAGAG CGTAACACGC TTCTTTT        7200

TAGGGTTGAC CGTGGCTGAC GTGGCTAGCC TGTGTGAGAT GGAGATCCAG AACCATA        7260

CCTATTGTGA CAAGGTGCGC ACTCCGCTCG AATTGCAAGT TGGGTGCTTG GTGGGCA        7320

AACTTACCTT TGAATGTGAC AAGTGTGAGG CACGCCAAGA GACCCTTGCC TCCTTCT        7380

ACATATGGTC CGGGGTCCCA CTTACTCGGG CCACTCCGGC CAAACCACCA GTGGTGA        7440

CGGTGGGGTC CTTGTTGGTG GCAGACACCA CCAAGGTCTA CGTGACCAAT CCGGACA        7500

TTGGGAGGAG GGTTGACAAG GTGACTTTCT GGCGCGCTCC TCGGGTACAC GACAAGT        7560

TCGTGGACTC GATCGAGCGC GCTCGGAGAG CTGCTCAAGG CTGCCTAAGC ATGGGTT        7620

CTTATGAGGA GGCAATAAGG ACTGTTAGGC CGCATGCTGC CATGGGCTGG GGATCTA        7680

TGTCGGTCAG GGACTTGGCC ACCCCTGCGG GGAAGATGGC TGTTCATGAC CGGCTTC        7740

AGATACTTGA AGGGACTCCA GTCCCTTTTA CCCTGACTGT CAAAAAGGAG GTGTTCT        7800

AAGATCGTAA GGAGGAGAAG GCCCCCCGCC TCATTGTGTT CCCCCCCCTG GACTTCC        7860

TAGCTGAAAA GCTCATTCTG GGAGACCCGG GGCGGGTTGC AAAGGCGGTG TGGGGGG        7920

CTTACGCCTT CCAGTACACC CCCAACCAGC GGGTTAAGGA GATGCTAAAG CTGTGGG        7980

CAAAGAAGAC CCCGTGCGCC ATCTGTGTGG ATGCCACTTG CTTCGACAGT AGCATTA        8040

ARGAGGACGT GGCACTAGAG ACAGAGCTTT ACGCCCTGGC CTCGGACCAT CCAGAAT        8100

TGCGCGCCCT GGGGAAATAC TRTGCCTCTG GCACAATGGT GACCCCGGAA GGGGTGC        8160

TGGGCGAGAG GTATTGTAGG TCCTCGGGTG TGTTAACCAC AAGTGCTAGC AACTGTT        8220

CCTGCTACAT CAAAGTGAGA GCCGCCTGTG AGAGGATCGC ACTGAAAAAT GTCTCGC        8280

TCATCGCGGG CGATGACTGC TTAATTGTGT GCGAGAGGCC TGTATGCGAC CCTTGCG        8340

CCCTGGGCCG AGCCCTGGCT TCGTACGGGT ACGCGTGTGA GCCCTCGTAT CACGCTT        8400

TGGACACAGC CCCCTTCTGC TCCACTTGGC TTGCTGAGTG CAATGCGGAT GGGRAAA        8460

ATTTCTTCCT GACCACGGAC TTTCGGAGAC CACTCGCTCG CATGTCGAGC GAGTACA        8520

ACCCTATGGC TTCGGCCATT GGTTACATTC TCCTCTATCC CTGGCRTCCC ATCACAC        8580

GGGTCATCAT CCCGCATGTG CTAACATGCG CTTCTTTCCG GGGTGGTGGC ACACSGT        8640

ATCCGGTTTG GTGTCAGGTT CATGGTAACT ACTACAAGTT TCCCCTGGAC AAACTGC        8700

ACATCATCGT GGCCCTCCAC GGACCAGCAG CGTTGAGGGT TACCGCAGAC ACAACCA        8760

CAAAGATGGA GGCTGGGAAG GTTCTGAGCG ACCTCAAGCT CCCTGGTCTA GCCGTCC        8820

GCAAGAAGGC CGGGGCATTG CGAACACGCA TGCTCCGGTC GCGCGGTTGG GCGGAGT        8880

CTAGGGGCCT GTTGTGGCAT CCAGGACTCC GGCTTCCTCC CCCTGAGATT GCTGGTA        8940

CAGGGGGTTT CCCTCTGTCC CCCCCCTACA TGGGGGTGGT TCATCAATTG GATTTCA        9000

CSCAGCGGAG TCGCTGGCGG TGGTTGGGGT TCTTAGCCCT GCTCATCGTA GCGCTCT        9060

GGTGAACTAA ATTCATCTGT TGCGGCCGGA GTCAGACCTG AGCCCCGTTC AAAAGGG        9120

TGAGAC                                                              9126
```

(2) INFORMATION FOR SEQ ID NO:4:

(i) SEQUENCE CHARACTERISTICS:
        (A) LENGTH: 635 base pairs
        (B) TYPE: nucleic acid (C) STRANDEDNESS: single
           (D) TOPOLOGY: linear (ii) MOLECULE TYPE: DNA (genomic)

(xi) SEQUENCE DESCRIPTION: SEQ ID NO:4:

CACTGGGTGC AAGCCCCAGA AACCGACGCC TATCTAAGTA GACGCAATGA CTCGGCGCC       60

ACTCGGCGAC CGGCCAAAAG GTGGTGGATG GGTGATGACA GGGTTGGTAG GTCGTAAA      120

CCGGTCACCT TGGTAGCCAC TATAGGTGGG TCTTAAGAGA AGGTTAAGAT TCCTCTTG      180

CCTGCGGCGA GACCGCGCAC GGTCCACAGG TGTTGGCCCT ACCGGTGTGA ATAAGGGC      240

GACGTCAGGC TCGTCGTTAG ACCGAGCCCG TCACCCACCT GGGCAAACGT CGCCCACG      300

CGGTCCACGT CGCCCTTCAA TGTCTCTCTT GACCAATAGG CTTAGCCGGC CGAGTTGA      360

AGGACCAGTG GGGGTCGGGG GCTTGGGGAG GGACCCCAAG TCCTGCCCTT CCCGGTGG      420

CGGGAAATGC ATGGGGCCAC CCAGCTCCGC GGCGGCCTGC AGCCGGGGTA GCCCAAGA      480

CCTTCGGGTG AGGGCGGGTG GCATTTCTCT TTTCTATACC ATCATGGCAG TCCTTCTG      540

CCTTCTCGTG GTCGAGGCCG GGGCCATTCT GGCCCCGGCC ACCCACGCTT GTCGAGCG      600

TGGGGCAATA CTTCCTCACA AACTGTTGCG CCCTG                                635

(2) INFORMATION FOR SEQ ID NO:5:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:5:

TATAATAAGC TTGCCCCGGA CCTCCCACCG AG                                   32

(2) INFORMATION FOR SEQ ID NO:6:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:6:

GCTCTAGATC GGGAACAACA ATTGGAAAG                                       29

(2) INFORMATION FOR SEQ ID NO:7:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:7:

TATAATAAGC TTCACTGGGT GCAAGCCCCA GAA                                  33

(2) INFORMATION FOR SEQ ID NO:8:

(i) SEQUENCE CHARACTERISTICS:
          (A) LENGTH: 29 base pairs
          (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:8:

GCTCTAGAGG CGCAACAGTT TGTGAGGAA                                    29

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GCTCTAGACA CTGGGTGCAA GCCCCA                                       26

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TATAATAAGC TTGGCGCAAC AGTTTGTGAG                                   30

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GCTCTAGAGC ACTGGTGCCG CGAGT                                        25

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GCTCTAGAGA GGGGGAAGCA AACCA                                        25

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GCTCTAGACA TGGTGAATGT GTCGACCAC                                      29

(2) INFORMATION FOR SEQ ID NO:14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GCTCTAGAAC AAGCGTGGGT GGCCGGGG                                       28

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GCTCTAGAGA CCACGAGAAG GAGCAGAAG                                      29

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GCTCTAGACA TGATGGTATA GAAAAGAG                                       28

(2) INFORMATION FOR SEQ ID NO:17:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CCATAATCAT GAGGGAACAA CAATTGGAAA G                                   31

(2) INFORMATION FOR SEQ ID NO:18:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CATGCCATGG CGCAACAGTT TGTGAGGAA                                      29

(2) INFORMATION FOR SEQ ID NO:19:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

TATAATAAAG CTTCACTCCC CTGTGAGGAA CTAC                      34

(2) INFORMATION FOR SEQ ID NO:20:

(i) SEQUENCE CHARACTERISTICS:
        (A) LENGTH:35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GTATTGCGTC ATGATGGTTT TTCTTTGGGG TTTAG                     35

(2) INFORMATION FOR SEQ ID NO:21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TATAATAAGC TTGCCGCGAG TTGAAGAGCA C                         31

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CCATAATCAT GAGCCCCCGG ACCTCCCACC GAG                       33

(2) INFORMATION FOR SEQ ID NO:23:

(i) SEQUENCE CHARACTERISTICS:
        (A) LENGTH: 9493 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

CGTGGGAGTC CGGGGCCCCG GACCTCCCAC CGAGGTGGGG GGAAAGGGGC CCTGGACCG      60

CCGGGTGGAA GGCCCGGAAC CGGTCCATCT TCCTCAAGGT TGAGGAAGGG GTACGTCT     120

CGGTCCGGTC GGTCCGAAAG GCGTCTGGAT GCCTAGTGTT AGGGTTCGTA GGTGGTAA     180

CCCAGCTAGG CGTGAAAGCG CTATAGGATA GGCTTATCCC GGTGACCGCT GCCCCGGA     240

-continued

| | |
|---|---|
| CAGCCCCGCG GKTCTTTGGA CACGGTCCAC AGGTTGGGGG TACCGGTGTG AATAACCC | 300 |
| CGACTGAAGC GTCAGTCGTT AAACGGAGAC GGTCTCCTGA GATCGCAACG ACGCCCCA | 360 |
| TACGGGAACG CCGCCAAAAC CTTCGGGACA GCTATGCGGG TTGACAATCC CAGTGGGG | 420 |
| CCGGGGACCA GCTGATTACT TGTCCTGCGA GTTCCTCTTG AGACTGGCCG AAAGGCAG | 480 |
| ACGGGGCCAC CAAGGCGGCG CAGCGCTGCA TGCGGCAAGG GGAAAAATCC TTCGGGTG | 540 |
| CCCTGGTGGC AATCCCTTCC CTTAGGAGCA TGAGTGTGGT CGACACATTC ACCATGGC | 600 |
| GGCTGTGGTT GCTGGTTTGC TTCCCCCTCG CGGGGGGGGT GCTCTTCAAC TCGCGGCA | 660 |
| AGTGCTTCAA TGGGGACCAT TATGTGCTTT CCAATTGTTG TTCCCGAGAC GAGGTTTA | 720 |
| TCTGTTTCGG GGACGGATGT CTGGTGGCTT ATGGCTGTAC TGTTTGCACA CAGTCTTG | 780 |
| GGAAGCTCTA CCGGCCTGGG GTGGCTACTC GGCCCGGGTC CGAACCAGGT GAGCTGCT | 840 |
| GGAGATTTGG GAGTGTAATT GGTCCGGTGT CGGCTTCGGC TTACACCGCT GGAGTCCT | 900 |
| GGTTGGGTGA ACCTTACAGT TTGGCCTTCT TGGGGACGTT CCTCACCAGT CGCCTCTC | 960 |
| GGATTCCCAA CGTCACCTGC GTGAAGGCTT GTGACCTTGA GTTTACCTAC CCAGGCT | 1020 |
| CCATCGATTT TGACTGGGCG TTTACCAAGA TCTTGCAGTT GCCGGCCAAG CTGTGGC | 1080 |
| GCCTAACGGC RGCWCCGGTC TTGAGCCTCC TCGTGATCCT CATGCTGGTC CTCGAGC | 1140 |
| GCCTCCTGAT AGCCTTCCTA CTGCTTTTGG TAGTGGGCGA GGCTCAGAGG GGGATGT | 1200 |
| ACAACTGCGT GTGTGGTTAC TGGGGGGGCA AGAGGCCCCC GTCGGTGACC CCGCTGT | 1260 |
| GTGGCAACGG TACTGTGGTG TGTGACTGTG ATTTTGGAAA AATGCATTGG GCCCCCC | 1320 |
| TGTGTTCCGG YCTGGTGTGG CGGGACGGTC ATAGGAGGGG CACCGTGCGC GACCTCC | 1380 |
| CGGTTTGCCC CCGGGAGGTT CTCGGCACGG TGACAGTCAT GTGTCAGTGG GGTTCTG | 1440 |
| ACTGGATTTG GAGATTTGGG GACTGGGTTG CATTGTACGA CGAGCTACCA CGATCAG | 1500 |
| TCTGTACTTT CTTCTCAGGT CATGGTCCAC AACCTAAAGA TCTCTCAGTC TTGAATC | 1560 |
| CCGGGGCACC TTGTGCTTCT TGCGTCGTTG ACCAGAGGCC GCTGAAATGT GGTTCCT | 1620 |
| TCCGCGACTG CTGGGAGACG GGGGGTCCTG GGTTCGATGA GTGCGGTGTC GGTACTC | 1680 |
| TGACGAAGCA CCTCGAGGCC GTCCTGGTTG ATGGAGGTGT GGAGTCCAAG GTGACAA | 1740 |
| CCAAGGGTGA GCGCCCCAAA TACATAGGTC AGCACGGTGT GGGAACCTAC TACGGCG | 1800 |
| TCCGTAGCCT CAACATCAGT TACCTAGTGA CTGAGGTGGG GGGCTATTGG CATGCGC | 1860 |
| AGTGCCCGTG CGACTTTGTG CCCCGAGTGC TCCCAGAAAG AATTCCAGGT AGGCCTG | 1920 |
| ATGCATGTCT AGCTGGGAAG TCTCCGCACC CGTTCGCAAG TTGGGCTCCC GGTGGGT | 1980 |
| ACGCCCCGT GTTCACCAAG TGCAACTGGC CGAAGACCTC CGGAGTGGAT GTGTGTC | 2040 |
| GGTTTGCTTT CGATTTCCCT GGTGATCACA ACGGCTTCAT CCATGTTAAA GGCAACA | 2100 |
| AGCAGGTTTA CAGTGGTCAG CGAAGGTCTT CGCCGGCTTG GTTGCTTACT GACATGG | 2160 |
| TGGCCCTGTT GGTGGTGATG AAGTTGGCTG AGGCTAGAGT TGTCCCCCTG TTTATGC | 2220 |
| CAATGTGGTG GTGGTTGAAT GGAGCATCTG CTGCCACTAT TGTCATCATA CACCCTA | 2280 |
| TCACGAAGTC CACTGAAAGT GTTCCATTGT GGACTCCGCC CACTGTTCCA ACTCCAT | 2340 |
| GCCCGAATTC TACCACCGGA GTCGCGGACT CTACCTACAA TGCTGGTTGC TACATGG | 2400 |
| CAGGCCTGGC GGCCGGGGCT CAGGCGGTCT GGGGTGCTGC CAATGATGGT GCTCAGG | 2460 |
| TCGTTGGTGG CATCTGGCCC GCGTGGCTCA AGCTGCGAAG CTTCGCTGCC GGTCTGG | 2520 |
| GGTTGTCAAA TGTTGGGGCT TACTTGCCGG TCGTCGAGGC CGCVCTGGCT CCCGAGC | 2580 |
| TGTGCACCCC GGTGGTCGGC TGGGCAGCCC AGGAGTGGTG GTTCACTGGT TGTCTGG | 2640 |

-continued

| | |
|---|---|
| TGATGTGTGT CGTGGCGTAC CTGAATGTCC TGGGCTCTGT RAGGGCTGCC GTGCTTG | 2700 |
| CGATGCACTT CGCAAGGGGT GCTCTGCCGC TGGTATTGGT GGTAGCTGCC GGGGTRA | 2760 |
| GGGAGCGGCA CAGCGTCTTA GGGCTTGAGG TGTGCTTCGA TCTGGATGGT GGAGACT | 2820 |
| CRGACGCCAG TTGGTCTTGG GGTTTAGCAG GCGTGGTGAG CTGGGCCCTC CTGGTGG | 2880 |
| GTCTGATGAC CCACGGTGGC CGATCAGCCA GAYTGACTTG GTAYGCCAGG TGGGCCG | 2940 |
| ATTAYCAGAG GGTTCGYCGG TGGGTGAACA ACTCACCGGT TGGAGCYTTT GGYCGTT | 3000 |
| GGCGYGCCTG GAAAGCYTGG TTRGTKGTGG CTTGGTTCTT CCCCCAGACA GTTGCCA | 3060 |
| TYTCCGTCAT CTTCATACTC TGTTTGAGCA GTTTAGATGT CATTGATTTC ATCTTGG | 3120 |
| TACTCTTGGT TAACTCACCA AATCTCGCGC GCTTGGCGCG RGTGCTGGAC TCCTTAG | 3180 |
| THGCTGAGGA GCGGCTGGCC TGCTCTTGGC TGGTGGGCGT CCTGCGCAAG CGGGGCG | 3240 |
| TCCTCTACGA GCACGCYGGT CACACTAGCA GGCGCGGTGC TGCCCGCTTG CGAGAGT | 3300 |
| GYTTTGCGCT YGAGCCKGTT AGYATAACCA AGGAAGATTG YGCYATTGTT CGGGACT | 3360 |
| CTCGTGTGTT GGGCTGTGGA CAATTGGTCC ATGGGAAACC AGTGGTCGCG AGGCGAG | 3420 |
| ACGAGGTGTT GATCGGCTGT GTGAACAGTC GGTTCGACCT TCCGCCTGGC TTTGTTC | 3480 |
| CTGCTCCCGT GGTSCTTCAT CARGCWGGCA ARGGRTTYTT YGGGGTTGTG AAGACMT | 3540 |
| TGACAGGCAA GGACCCGTCC GAACACCACG GRAACGTGGT GGTCCTWGGG ACTTCAA | 3600 |
| CKCGTTCCAT GGGCTGCTGC GTGAACGGAG TAGTGTACAC RACATACCAT GGYACCA | 3660 |
| CCCGRCCKAT GGCGGGGCCK TTTGGKCCYG TCAAYGCTCG GTGGTGGTCW GCGAGYG | 3720 |
| ACGTCACGGT YTACCCGCTC CCWAATGGYG CTTCTTGCCT YCARGCWTGY AAGTGCC | 3780 |
| CAACTGGGGT GTGGGTGATC CGGAATGACG GAGCTCTTTG CCATGGAACT CTCGGCA | 3840 |
| TGGTGGATTT AGATATGCCC GCTGAGTTGT CAGACTTTCG CGGGTCTTCT GGATCAC | 3900 |
| TCTTGTGCGA TGAGGGTCAT GCTGTTGGCA TGCTGATTTC GGTGCTTCAT AGGGGGA | 3960 |
| GGGTTTCCTC GGTGCGGTAT ACCAAACCTT GGGAAACTCT CCCTCGGGAG ATTGAGG | 4020 |
| GATCGGAGGC CCCCCCTGTG CCAGGAACCA CTGGATACAG GGAGGCGCCA CTGTTCC | 4080 |
| CCACCGGAGC TGGCAAGTCG ACGCGCGTGC CGAATGAGTA CGTCAAGGCT GGACACA | 4140 |
| TGCTTGTACT AAACCCATCC ATTGCCACAG TGAGGGCCAT GGGCCCTTAC ATGGAAA | 4200 |
| TAACCGGCAA ACATCCGTCG GTGTACTGTG GCCATGACAC TACTGCATAT TCCAGGA | 4260 |
| CTGACTCATC TTTGACCTAC TGTACATACG GCAGGTTTAT GGCCAATCCC AGGAAAT | 4320 |
| TGCGGGGGAA CGACGTCGTA ATTTGCGACG AGTTGCACGT CACCGACCCG ACCTCAA | 4380 |
| TGGGGATGGG TCGGGCGAGG TTACTCGCTC GCGAGTGCGG CGTACGCCTC CTGCTTT | 4440 |
| CTACGGCGAC CCCACCGGTC TCTCCGATGG CGAAGCATGA ATCTATTCAT GAGGAGA | 4500 |
| TGGGCAGTGA GGGGGAGGTC CCCTTCTATT GCCAATTCCT CCCACTGAGT AGGTATG | 4560 |
| CTGGGAGACA CCTGCTGTTT TGTCATTCCA AGGTAGARTG CACTAGGTTA TCCTCAG | 4620 |
| TGGCCAGCTT TGGTGTCAAC ACCGTTGTGT ACTTCAGAGG CAAAGAAACT GACATTC | 4680 |
| CTGGTGACGT GTGCGTTTGC GCCACAGACG CACTTTCCAC TGGTTACACT GGCAATT | 4740 |
| ACACCGTAAC AGACTGTGGT TTAATGGTTG AGGAGGTAGT GGAAGTGACC CTGGACC | 4800 |
| CCATCACTAT CGGTGTGAAG ACCGTCCCGG CCCCTGCCGA ACTGAGGGCT CAGAGGC | 4860 |
| GTAGGTGTGG CCGTGGGAAA GCGGGCACTT ACTATCAGGC ATTGATGTCT TCGGCGC | 4920 |
| CGGGAACSGT TCGGTCTGGG GCTCTCTGGG CAGCTGTTGA GGCTGGHGTC TCGTGGT | 4980 |
| GCCTAGAGCC CGATGCTATT GGAGACCTGC TTAGGGCCTA CGACTCGTGT CCTTATA | 5040 |

-continued

```
CTGCCATCAG TGCGTCCATC GGAGAGGCCA TTGCCTTTTT TACTGGYCTA GTGCCAA       5100
GGAATTATCC TCAGGTGGTT TGGGCCAAGC AGAAGGGRCA CAACTGGCCA CTCTTGG       5160
GTGTGCAGAG GCACATGTGT GAGGACGCGG GCTGTGGTCC KCCCGCTAAT GGTCCCG       5220
GGAGCGGCAT CAGGGGAAAA GGGCCTGTTC CCCTGTTGTG CCGATGGGGT GGTGACT       5280
CTGAGTCGGT GGCTCCGCAT CACTGGGTTG ATGACCTACA GGCCCGGCTC GGTGTGG       5340
AGGGTTACAC TCCCTGCATT GCTGGACCGG TGCTTTTGGT CGGTTTGGCG ATGGCGG       5400
GGGCTATCCT GGCACACTGG ACGGGGTCTC TGGTTGTAGT GACCAGTTGG GTTGTCA       5460
GGAACGGTAA CCCGCTGATA CAAAGCGCCT CTAGGGGCGT GGCKACYAGC GGTCCAT       5520
CAGTACCCCC AGATGGTGGT GAACGGTACC CATCAGACAT CAAGCCAATY ACTGAGG       5580
TGACCACCCT TGAGACTGCG TGCGGYTGGG GCCCAGCCGC GGCBAGTCTG GCTTATG       5640
AGGCCTGTGA AACTGGAACC ATGTTGGCTG ACAARGCGAG TGCTGCGTGG CAGGCTT       5700
CTGCAAACAA CTTTGTGCCT CCACCAGCAT CACACTCAAC TTCCTTGTTR CAGAGCT       5760
AYGCTGCGTT CACTTCAGCT TGGGATAGCG TGTTCACTCA CGGCCGTTCC TTGCTTG       5820
GGTTCACAGC TGCTTACGGC GCTCGGCGGA ACCCACCGCT GGGCGTCGGA GCCTCTT       5880
TGCTGGGCAT GTCATCGAGC CACYTRACTC ACGTCAGACT TGCTGCTGCG TTGCTCC       5940
GCGTCGGGGG TACCGTCCTA GGCACGCCTG CTACTGGGCT TGCTATGGCG GGTGCCT       6000
TCGCKGGGGG CAGCGTTACC GCTAACTGGC TGAGTATCAT TGTGGCTCTA ATCGGAG       6060
GGGAGGGGGC RGTKAACGCA GCCTCACTCA CCTTCGAYCT CCTGGCKGGG AAGTTAC       6120
CKAGYGAYGC TTGGTGCCTR GTCAGYTGCY TGGCCTCTCC GGGGGCTTCG GTGGCYG       6180
TGGCDCTVGG YCTDYTGCTV TGGTCTGTCA ARAAGGGTGT GGGWCARGAY TGGGTTA       6240
GAYTGTTGAC GATGATGCCA CGCAGTTCGG TGATGCCTGA CGATTTCTTC CTCAAAG       6300
AGTTCGTCAC CAAGGTGTCT ACTGTCCTGC GAAAGTTGTC ATTGTCAAGA TGGATCA       6360
CTCTTGTGGA CAAGCGGGAG ATGGAGATGG AGACMCCCGC TTCTCAGATT GTTTGGG       6420
TGCTTGACTG GTGCATCCGG CTRGGTCGGT TCCTGTACAA TAAACTYATG TTTGCTC       6480
CTAGGTTGCG CCTGCCGCTT ATCGGTTGCA GTACCGGTTG GGGTGGCCCG TGGGAGG       6540
ATGGTCATTT GGAAACAAGG TGTACTTGTG GCTGTGTGAT TACCGGTGAT ATTCACG       6600
GTATATTGCA CGACCTACAT TATACCTCCC TACTGTGCAG ACATTACTAC AAGAGGA       6660
TGCCTGTTGG CGTCATGGGC AATGCTGAGG GAGCAGTCCC CCTTGTGCCT ACTGGCG       6720
GAATCAGGAC TTACCAAATT GGGACTTCTG ACTGGTTTGA GGCTGTGGTC GTGCATG       6780
CAATCACGGT GCACGCCACC AGTTGCTATG AGTTGAAAGC TGCTGACGTT CGGAGGG       6840
TGCGAGCCGG CCCGACTTAC GTTGGTGGCG TACCTTGCAG CTGGAGCGCG CCGTGTA       6900
CGCCTGCGCT CGTTTACAGG CTAGGCCAGG GCATCAAAAT CGATGGAGCG CGCCGAC       6960
TGCCCTGTGA CTTAGCACAG GGAGCGCGCC ACCCCCGGT ATCTGGCAGT GTTGCCG       7020
GTGGTTGGAC AGATGAGGAC GAGAGGGACT TGGTGGAAAC CAAGGCTGCC GCCATCG       7080
CCATTGGGGC GGCCTTGCAC CTCCCTTCAC CGGAGGCTGC TCAGGCCGCT CTAGAGG       7140
TGGAGGAGGC TGCCGTGTCC CTGTTGCCCC ATGTGCCCGT CATTATGGGT GATGACT       7200
CATGCCGGGA TGAGGCGTTC CAAGGCCACT TCATCCCAGA ACCCAATGTG ACAGAGG       7260
CCATTGAGCC CACGGTCGGA GACGTGGAGG CACTCAAGCT GCGGGCTGCA GACCTGA       7320
CCAGGTTGCA AGACTTGGAG GCCATGGCTC TCGCCCGCGC TGAGTCAATC GAGGATG       7380
GCGCAGCTTC GATGCCTTCG CTCACCGAGG TGGACTCAAT GCCATCATTG GAGTCGA       7440
```

```
CTTGCTCCTC CTTTGAACAA ATCTCTTTAA CTGAAAGTGA CCCTGAGACT GTCGTCG      7500

CTGGCTTACC CTTGGAGTTC GTGAACTCCA ACACCGGGCC GTCTCCGGCT CGGAGGA      7560

TCAGAATCCG ACAGGCTTGC TGTTGTGACA GATCCACAAT GAAGGCCATG CCGTTGT      7620

TCACTGTCGG GGAGTGCCTC TTCGTTACTC GCTATGACCC GGACGGTCAC CAACTGT      7680

ACGAGCGAGG TCCGATAGAG GTATCTACTC CTATATGTGA AGTGATTGGG GACATCA      7740

TTCAGTGTGA CCAAATTGAG GAAACTCCAA CATCTTACTC TTACATCTGG TCAGGGG      7800

CCTTGGGTAC TGGGAGAAGT GTCCCCCAAC CCATGACGCG CCCTATAGGG ACCCATC      7860

CTTGTGACAC TACCAAAGTT TATGTTACTG ACCCTGATCG GGCCGCTGAG CGGGCCG      7920

AGGTTACAAT CTGGAGGGGT GATAGGAAGT ATGACAAGCA TTATGAGGCT GTCGTTG      7980

CTGTCCTGAA AAAGGCAGCC GCGACGAAGT CTCATGGCTG GACCTATTCC CAGGCTA      8040

CTAAAGTTAG GCGCCGAGCA GCCGCTGGAT ACGCAGCAA GGTGACCGCC TCCACAT       8100

CCACTGGTTG GCCTCACGTG GAGGAGATGC TGGACAAAAT AGCCAGGGGA CAGGAAG      8160

CTTTCACTTT TGTGACCAAG CGAGAGGTTT TCTTCTCCAA AACTACCCGT AAGCCCC      8220

GATTCATAGT TTTCCCACCT TTGGACTTCA GGATAGCTGA AAAGATGATT CTGGGTG      8280

CCGGCATCGT TGCAAAGTCA ATTCTGGGTG ACGCTTATCT GTTCCAGTAC ACGCCCA      8340

AGAGGGTCAA AGCTCTGGTT AAGGCGTGGG AGGGGAAGTT GCATCCCGCT GCGATCA      8400

TGGACGCCAC TTGTTTCGAC TCATCGATTG ATGAGCACGA CATGCAGGTG GAGGCTT      8460

TGTTTGCGGC GGCTAGTGAC AACCCCTCAA TGGTACATGC TTTGTGCAAG TACTACT      8520

GTGGCCCTAT GGTTTCCCCA GATGGGGTTC CCTTGGGGTA CCGCCAGTGT AGGTCGT      8580

GCGTGTTAAC AACTAGCTCG GCGAACAGCA TCACTTGTTA CATTAAGGTC AGCGCGG      8640

GCAGGCGGGT GGGGATTAAG GCACCATCAT TCTTTATAGC TGGAGATGAT GCTTGA       8700

TCTATGAAAA TGATGGAACT GATCCCTGCC CTGCTCTTAA GGCTGCCCTG GCCAACT      8760

GATACAGGTG TGAACCAACA AAGCATGCTT CACTGGACAC AGCTGAGTGT TGCTCGG      8820

ACTTGGCTGA GTGCGTAGCT GGGGGTGCCA AGCGCTGGTG GTTGAGCACG ACATGA       8880

AGCCGCTCGC AAGGGCGTCT TCCGAATATT CGGACCCAAT CGGCAGTGCT TTAGGGA      8940

TCTTGATGTA TCCCCGGCAT CCAATCGTGC GGTATGTTCT AATACCACAC GTACTAA      9000

TGGCTTACAG GAGTGGCAGC ACACCGGATG AGTTGGTTAT GTGTCAGGTT CAGGGAA      9060

ATTACTCTTT CCCGCTGCGG CTGCTGCCTC GCGTCTTGGT CTCTCTACAT GGTCCGT      9120

GCCTACAAGT CACCACGGAC AGTACGAAGA CTAGGATGGA GGCAGGCTCA GCSTTGC      9180

ATTTAGGAAT GAAATCCCTA GCCTGGCACC GCCGACGTGC CGGAAATGTG CGCACTC      9240

TCCTGAGGGG AGGCAAGGAG TGGGGGCACC TGGCCAGAGC CCTCCTCTGG CAYCCAG      9300

TGAAGGAGCA YCCCCCRCCC ATAAATTCAC TTCCAGGTTT TCAGCTGGCG ACGCCTT      9360

AACACCATGA AGAGGTCTTG ATCTCGATCA AGAGTCGACC ACCTTGGATA AGGTGGA      9420

TTGGTGCTTG TCTCTCGTTG CTGGCCGCCT TGCTGTGAAT TCGCTCCAGG CAGTAGG      9480

TTCGGGTCGG GGG                                                      9493
```

(2) INFORMATION FOR SEQ ID NO:24:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CCATAATCAT GAGCCGCGAG TTGAAGAGCA C                              31

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GCCAAGCCAT GGTGAATGTG                                           20

(2) INFORMATION FOR SEQ ID NO:26:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

GTATTGCGCC ATGGCTCGAC AAGCGTGGGT GGCCGGGG                        38

(2) INFORMATION FOR SEQ ID NO:27:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GGACTGCCAT GGTGGTATAG AAAAGAG                                   27

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

TATAATAAGC TTCTCGACAA GCGTGGGTGG CCGGGG                         36

(2) INFORMATION FOR SEQ ID NO:29:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GTATTGCGCC ATGGCACTGG GTGCAAGCCC AGAA                           34

(2) INFORMATION FOR SEQ ID NO:30:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

```
Met Ser Val Val Asp Thr Phe Thr Met Ala Trp Leu Trp Leu Leu
                 5                  10                  15

Cys Phe Pro Leu Ala Gly Gly Val Leu Phe Asn Ser Arg His Gln Cys
                20                  25                  30

Phe Asn Gly Asp His Tyr Val Leu Ser Asn Cys Cys Ser Arg
         35                  40                  45
```

(2) INFORMATION FOR SEQ ID NO:31:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

```
Met Gly Pro Pro Ser Ser Ala Ala Ala Cys Ser Arg Gly Ser Pro Arg
                 5                  10                  15

Ile Leu Arg Val Arg Ala Gly Gly Ile Ser Leu Phe Tyr Thr Ile Met
                20                  25                  30

Ala Val Leu Leu Leu Leu Leu Val Val Glu Ala Gly Ala Ile Leu Ala
             35                  40                  45

Pro Ala Thr His Ala Cys Arg Ala Asn Gly Gln Tyr Phe Leu Thr Asn
     50                  55                  60

Cys Cys Ala
 65
```

(2) INFORMATION FOR SEQ ID NO:32:

(i) SEQUENCE CHARACTERISTICS:
        (A) LENGTH: 9143 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:32:

```
ACCACAAACA CTCCAGTTTG TTACACTCCG CTAGGAATGC TCCTGGAGCA CCCCCCCTA      60

CAGGGCGTGG GGGATTTCCC CTGCCCGTCT GCAGAAGGGT GGAGCCAACC ACCTTAGT     120

GTAGGCGGCG GGACTCATGA CGCTCGCGTG ATGACAAGCG CCAAGCTTGA CTTGGATG     180

CCTGATGGGC GTTCATGGGT TCGGTGGTGG TGGCGCTTTA GGCAGCCTCC ACGCCCAC     240

CCTCCCAGAT AGAGCGGCGG CACTGTAGGG AAGACCGGGG ACCGGTCACT ACCAAGGA     300

CAGACCTCTT TTTGAGTATC ACGCCTCCGG AAGTAGTTGG GCAAGCCCAC CTATATGT     360

TGGGATGGTT GGGGTTAGCC ATCCATACCG TACTGCCTGA TAGGGTCCTT GCGAGGGG     420

CTGGGAGTCT CGTAGACCGT AGCACATGCC TGTTATTTCT ACTCAAACAA GTCCTGTA     480

TGCGCCCAGA ACGCGCAAGA ACAAGCAGAC GCAGGCTTCA TATCCTGTGT CCATTAAA     540
```

```
ATCTGTTGAA AGGGGACAAC GAGCAAAGCG CAAAGTCCAG CGCGATGCTC GGCCTCGT      600

TTACAAAATT GCTGGTATCC ATGATGGCTT GCAGACATTG GCTCAGGCTG CTTTGCCA      660

TCATGGTTGG GGACGCCAAG ACCCTCGCCA TAAGTCTCGC AATCTTGGAA TCCTTCTG      720

TTACCCTTTG GGGTGGATTG GTGATGTTAC AACTCACACA CCTCTAGTAG GCCCGCTG      780

GGCAGGAGCG GTCGTTCGAC CAGTCTGCCA GATAGTACGC TTGCTGGAGG ATGGAGTC      840

CTGGGCTACT GGTTGGTTCG GTGTCCACCT TTTTGTGGTA TGTCTGCTAT CTTTGGCC      900

TCCCTGTAGT GGGGCGCGGG TCACTGACCC AGACACAAAT ACCACAATCC TGACCAAT      960

CTGCCAGCGT AATCAGGTTA TCTATTGTTC TCCTTCCACT TGCCTACACG AGCCTGG      1020

TGTGATCTGC GCGGACGAGT GCTGGGTTCC CGCCAATCCG TACATCTCAC ACCCTTC      1080

TTGGACTGGC ACGGACTCCT TCTTGGCTGA CCACATTGAT TTTGTTATGG GCGCTCT      1140

GACCTGTGAC GCCCTTGACA TTGGTGAGTT GTGTGGTGCG TGTGTATTAG TCGGTGA      1200

GCTTGTCAGG CACTGGCTTA TTCACATAGA CCTCAATGAA ACTGGTACTT GTTACCT      1260

AGTGCCCACT GGAATAGATC CTGGGTTCCT AGGGTTTATC GGGTGGATGG CCGGCAA      1320

CGAGGCTGTC ATCTTCTTGA CCAAACTGGC TTCACAAGTA CCATACGCTA TTGCGAC      1380

GTTTAGCAGT GTACACTACC TGGCGGTTGG CGCTCTGATC TACTATGCCT CTCGGGG      1440

GTGGTATCAG TTGCTCCTAG CGCTTATGCT TTACATAGAA GCGACCTCTG GAAACCC      1500

CAGGGTGCCC ACTGGATGCT CAATAGCTGA GTTTTGCTCG CCTTTGATGA TACCATG      1560

TTGCCACTCT TATTTGAGTG AGAATGTGTC AGAAGTCATT TGTTACAGTC CAAAGTG      1620

CAGGCCTGTC ACTCTAGAGT ATAACAACTC CATATCTTGG TACCCCTATA CAATCCC      1680

TGCGAGGGGA TGTATGGTTA AATTCAAAAA TAACACATGG GGTTGCTGCC GTATTCG      1740

TGTGCCATCG TACTGCACTA TGGGCACTGA TGCAGTGTGG AACGACACTC GCAACAC      1800

CGAAGCATGC GGTGTAACAC CATGGCTAAC AACCGCATGG CACAACGGCT CAGCCCT      1860

ATTGGCTATA TTACAATACC CTGGGTCTAA AGAAATGTTT AAACCTCATA ATTGGAT      1920

AGGCCATTTG TATTTTGAGG GATCAGATAC CCCTATAGTT TACTTTTATG ACCCTGT      1980

TTCCACTCTC CTACCACCGG AGAGGTGGGC TAGGTTGCCC GGTACCCCAC CTGTGGT      2040

TGGTTCTTGG TTACAGGTTC CGCAAGGGTT TTACAGTGAT GTGAAAGACC TAGCCAC      2100

ATTGATCACC AAAGACAAAG CCTGGAAAAA TTATCAGGTC TTATATTCCG CCACGGG      2160

TTTGTCTCTT ACGGGAGTTA CCACCAAGGC CGTGGTGCTA ATTCTGTTGG GGTTGTG      2220

CAGCAAGTAT CTTATTTTAG CCTACCTCTG TTACTTGTCC CTTTGTTTTG GGCGCGC      2280

TGGTTACCCT TTGCGTCCTG TGCTCCCATC CCAGTCGTAT CTCCAAGCTG GCTGGGA      2340

TTTGTCTAAA GCTCAAGTAG CTCCTTTTGC TTTGATTTTC TTCATCTGTT GCTATCT      2400

CTGCAGGCTA CGTTATGCTG CCCTTTTAGG GTTTGTGCCC ATGGCTGCGG GCTTGCC      2460

AACTTTCTTT GTTGCAGCAG CTGCTGCCCA ACCAGATTAT GACTGGTGGG TGCGACT      2520

AGTGGCAGGG TTAGTTTTGT GGGCCGGCCG TGACCGTGGT CCACGTATAG CTCTGCT      2580

AGGTCCTTGG CCTCTGGTAG CGCTTTTAAC CCTCTTGCAT TTGGCTACGC CTGCTTC      2640

TTTTGACACC GAGATAATTG GAGGGCTGAC AATACCACCT GTAGTAGCAT TAGTTGT      2700

GTCTCGTTTT GGCTTCTTTG CTCACTTGTT ACCTCGCTGT GCTTTAGTTA ACTCCTA      2760

TTGGCAACGT TGGGAGAATT GGTTTTGGAA CGTTACACTA AGACCGGAGA GGTTTCT      2820

TGTGCTGGTT TGTTTCCCCG GTGCGACATA TGACACGCTG GTGACTTTCT GTGTGTG      2880

CGTAGCTCTT CTATGTTTAA CATCCAGTGC AGCATCGTTC TTTGGGACTG ACTCTAG      2940
```

```
TAGGGCCCAT AGAATGTTGG TGCGTCTCGG AAAGTGTCAT GCTTGGTATT CTCATTA      3000

TCTTAAGTTT TTCCTCTTAG TGTTTGGTGA GAATGGTGTG TTTTTCTATA AGCACTT      3060

TGGTGATGTC TTGCCTAATG ATTTTGCCTC GAAACTACCA TTGCAAGAGC CATTTTT      3120

TTTTGAAGGC AAGGCAAGGG TCTATAGGAA TGAAGGAAGA CGCTTGGCGT GTGGGGA      3180

GGTTGATGGT TTGCCCGTTG TTGCGCGTCT CGGCGACCTT GTTTTCGCAG GGTTAGC      3240

GCCGCCAGAT GGGTGGGCCA TTACCGCACC TTTTACGCTG CAGTGTCTCT CTGAACG      3300

CACGCTGTCA GCGATGGCAG TGGTCATGAC TGGTATAGAC CCCCGAACTT GGACTGG      3360

TATCTTCAGA TTAGGATCTC TGGCCACTAG CTACATGGGA TTTGTTTGTG ACAACGT      3420

GTATACTGCT CACCATGGCA GCAAGGGGCG CCGGTTGGCT CATCCCACAG GCTCCAT      3480

CCCAATAACC GTTGACGCGG CTAATGACCA GGACATCTAT CAACCACCAT GTGGAGC      3540

GTCCCTTACT CGGTGCTCTT GCGGGAGAC CAAGGGGTAT CTGGTAACAC GACTGGG       3600

ATTGGTTGAG GTCAACAAAT CCGATGACCC TTATTGGTGT GTGTGCGGGG CCCTTCC      3660

GGCTGTTGCC AAGGGTTCTT CAGGTGCCCC GATTCTGTGC TCCTCCGGGC ATGTTAT      3720

GATGTTCACC GCTGCTAGAA ATTCTGGCGG TTCAGTCAGC CAGATTAGGG TTAGGCC      3780

GGTGTGTGCT GGATACCATC CCCAGTACAC AGCACATGCC ACTCTTGATA CAAAACC      3840

TGTGCCTAAC GAGTATTCAG TGCAAATTTT AATTGCCCCC ACTGGCAGCG GCAAGTC      3900

CAAATTACCA CTTTCTTACA TGCAGGAGAA GTATGAGGTC TTGGTCCTAA ATCCCAG      3960

GGCTACAACA GCATCAATGC CAAAGTACAT GCACGCGACG TACGGCGTGA ATCCAAA      4020

CTATTTTAAT GGCAAATGTA CCAACACAGG GGCTTCACTT ACGTACAGCA CATATGG      4080

GTACCTGACC GGAGCATGTT CCCGGAACTA TGACGTCATC ATTTGTGACG AATGCCA      4140

TACCGATGCA ACCACCGTGT TGGGCATTGG AAAGGTTCTA ACCGAAGCTC CATCCAA      4200

TGTTAGGCTA GTGGTTCTTG CCACGGCTAC CCCCCCTGGA GTAATCCCTA CACCACA      4260

CAACATAACT GAGATTCAAT TAACCGATGA AGGCACTATC CCCTTTCATG GAAAAAA      4320

TAAGGAGGAA AATCTGAAGA AAGGGAGACA CCTTATCTTT GAGGCTACCA AAAAACA      4380

TGATGAGCTT GCTAACGAGT TAGCTCGAAA GGGAATAACA GCTGTCTCTT ACTATAG      4440

ATGTGACATC TCAAAAATCC CTGAGGGCGA CTGTGTAGTA GTTGCCACTG ATGCCTT      4500

TACAGGGTAC ACTGGTGACT TTGATTCCGT GTATGACTGC AGCCTCATGG TAGAAGG      4560

ATGCCATGTT GACCTTGACC CTACTTTCAC CATGGGTGTT CGTGTGTGCG GGTCTC       4620

AATAGTTAAA GGCCAGCGTA GGGGCCGCAC AGGCCGTGGG AGAGCTGGCA TATACTA      4680

TGTAGACGGG AGTTGTACCC CTTCGGGTAT GGTTCCTGAA TGCAACATTG TTGAAGC      4740

CGACGCAGCC AAGGCATGGT ATGGTTTGTC ATCAACAGAA GCTCAAACTA TTCTGGA      4800

CTATCGCACC CAACCTGGGT TACCTGCGAT AGGAGCAAAT TTGGACGAGT GGGCTGA      4860

CTTTTCTATG GTCAACCCCG AACCTTCATT TGTCAATACT GCAAAAGAA CTGCTGA       4920

TTATGTTTTG TTGACTGCAG CCCAACTACA ACTGTGTCAT CAGTATGGCT ATGCTGC      4980

CAATGACGCA CCACGGTGGC AGGGAGCCCG GCTTGGGAAA AAACCTTGTG GGGTTCT      5040

GCGCTTGGAC GGCGCTGACG CCTGTCCTGG CCCAGAGCCC AGCGAGGTGA CCAGATA      5100

AATGTGCTTC ACTGAAGTCA ATACTTCTGG GACAGCCGCA CTCGCTGTTG GCGTTGG      5160

GGCTATGGCT TATCTAGCCA TTGACACTTT TGGCGCCACT GTGTGCGGC GTTGCTG       5220

TATTACATCA GTCCCTACCG GTGCTACTGT CGCCCCAGTG GTTGACGAAG AAGAAAT      5280

GGAGGAGTGT GCATCATTCA TTCCCTTGGA GGCCATGGTT GCTGCAATCG ATAAGCT      5340
```

```
GAGTACAATA ACCACAACTA GTCCTTTCAC ATTGGAAACC GCCCTTGAAA AACTTAA      5400

CTTTCTTGGG CCTCATGCAG CTACAATCCT TGCTATCATA GAGTATTGCT GTGGCTT      5460

CACTTTACCT GACAATCCCT TTGCATCATG CGTGTTTGCT TTCATTGCGG GTATTAC      5520

CCCACTACCT CACAAGATCA AAATGTTCCT GTCATTATTT GGAGGCGCAA TTGCGTC      5580

GCTTACAGAC GCTAGAGGCG CACTGGCGTT CATGATGGCC GGGGCTGCGG GAACAGC      5640

TGGTACATGG ACATCGGTGG GTTTTGTCTT TGACATGCTA GGCGGCTATG CTGCCGC      5700

ATCCACTGCT TGCTTGACAT TTAAATGCTT GATGGGTGAG TGGCCCACTA TGGATCA      5760

TGCTGGTTTA GTCTACTCCG CGTTCAATCC GGCCGCAGGA GTTGTGGGCG TCTTGTC      5820

TTGTGCAATG TTTGCTTTGA CAACAGCAGG GCCAGATCAC TGGCCCAACA GACTTCT      5880

TATGCTTGCT AGGAGCAACA CTGTATGTAA TGAGTACTTT ATTGCCACTC GTGACAT      5940

CAGGAAGATA CTGGGCATTC TGGAGGCATC TACCCCCTGG AGTGTCATAT CAGCTTG      6000

CCGTTGGCTC CACACCCCGA CGGAGGATGA TTGCGGCCTC ATTGCTTGGG GTCTAGA      6060

TTGGCAGTAT GTGTGCAATT TCTTTGTGAT TTGCTTTAAT GTCCTTAAAG CTGGAGT      6120

GAGCATGGTT AACATTCCTG GTTGTCCTTT CTACAGCTGC CAGAAGGGGT ACAAGGG      6180

CTGGATTGGA TCAGGTATGC TCCAAGCACG CTGTCCATGC GGTGCTGAAC TCATCTT      6240

TGTTGAGAAT GGTTTTGCAA AACTTTACAA AGGACCCAGA ACTTGTTCAA ATTACTG      6300

AGGGGCTGTT CCAGTCAACG CTAGGCTGTG TGGGTCGGCT AGACCGGACC CAACTGA      6360

GACTAGTCTT GTCGTCAATT ATGGCGTTAG GGACTACTGT AAATATGAGA AATTGGG      6420

TCACATTTTT GTTACAGCAG TATCCTCTCC AAATGTCTGT TTCACCCAGG TGCCCCC      6480

CTTGAGAGCT GCAGTGGCCG TGGACGGCGT ACAGGTTCAG TGTTATCTAG GTGAGCC      6540

AACTCCTTGG ACGACATCTG CTTGCTGTTA CGGTCCGGAC GGTAAGGGTA AAACTGT      6600

GCTTCCCTTC CGCGTTGACG GTCACACACC TGGTGTGCGC ATGCAACTTA ATTTGCG      6660

TGCACTTGAG ACAAATGACT GTAATTCCAT AAACAACACT CCTAGTGATG AAGCCGC      6720

GTCCGCTCTT GTTTTCAAAC AGGAGTTGCG GCGTACAAAC CAATTGCTTG AGGCAAT      6780

AGCTGGCGTT GACACCACCA AACTGCCAGC CCCCTCCATC GAAGAGGTAG TGGTAAG      6840

GCGCCAGTTC CGGGCAAGAA CTGGTTCGCT TACCTTGCCT CCCCCTCCGA GATCCGT      6900

AGGAGTGTCA TGTCCTGAAA GCCTGCAACG AAGTGACCCG TTAGAAGGTC CTTCAAA      6960

CCCTTCTTCA CCACCTGTTC TACAGTTGGC CATGCCGATG CCCCTGTTGG GAGCAGG      7020

GTGTAACCCT TTCACTGCAA TTGGATGTGC AATGACCGAA ACAGGCGGAG GCCCTGA      7080

TTTACCCAGT TACCCTCCCA AAAAGGAGGT CTCTGAATGG TCAGACGGAA GTTGGTC      7140

GACTACAACC GCTTCCAGCT ACGTTACTGG CCCCCCGTAC CCTAAGATAC GGGGAAA      7200

TTCCACTCAG TCAGCCCCCG CCAAACGGCC TACAAAAAAG AAGTTGGGAA AGAGTGA      7260

TTCGTGCAGC ATGAGCTACA CTTGGACCGA CGTGATTAGC TTCAAAACTG CTTCTAA      7320

TCTGTCTGCA ACTCGGGCCA TCACTAGTGG TTTCCTCAAA CAAAGATCAT TGGTGTA      7380

GACTGAGCCG CGGGATGCGG AGCTTAGAAA ACAAAAAGTC ACTATTAATA GACAACC      7440

GTTCCCCCCA TCATACCACA AGCAAGTGAG ATTGGCTAAG GAAAAAGCTT CAAAAGT      7500

CGGTGTCATG TGGGACTATG ATGAAGTAGC AGCTCACACG CCCTCTAAGT CTGCTAA      7560

CCACATCACT GGCCTTCGGG GCACTGATGT TCGTTCTGGA GCAGCCCGCA AGGCTGT      7620

GGACTTGCAG AAGTGTGTCG AGGCAGGTGA GATACCGAGT CATTATCGGC AAACTGT      7680

AGTTCCAAAG GAGGAGGTCT TCGTGAAGAC CCCCCAGAAA CCAACAAAGA AACCCCC      7740
```

```
GCTTATCTCG TACCCCCACC TTGAAATGAG ATGTGTTGAG AAGATGTACT ACGGTCA      7800

TGCTCCTGAC GTAGTTAAAG CTGTCATGGG AGATGCGTAC GGGTTTGTCG ACCCACG      7860

CCGTGTCAAG CGTCTGTTGT CGATGTGGTC ACCCGATGCA GTCGGAGCCA CATGCGA      7920

AGTGTGTTTT GACAGTACCA TCACACCCGA GGATATCATG GTGGAGACAG ACATCTA      7980

AGCAGCTAAA CTCAGTGACC AACACCGAGC TGGCATTCAC ACCATTGCGA GGCAGTT      8040

CGCTGGAGGA CCGATGATCG CTTATGATGG CCGAGAGATC GGATATCGTA GGTGTAG      8100

TTCCGGCGTC TATACTACCT CAAGTTCCAA CAGTTTGACC TGCTGGCTGA AGGTAAA      8160

TGCAGCCGAA CAGGCTGGCA TGAAGAACCC TCGCTTCCTT ATTTGCGGCG ATGATTG      8220

CGTAATTTGG AAGAGCGCCG GAGCAGATGC AGACAAACAA GCAATGCGTG TCTTTGC      8280

CTGGATGAAG GTGATGGGTG CACCACAAGA TTGTGTGCCT CAACCCAAAT ACAGTTT      8340

AGAATTAACA TCATGCTCAT CAAATGTTAC CTCTGGAATT ACCAAAAGTG GCAAGCC      8400

CTACTTTCTT ACAAGAGATC CTCGTATCCC CCTTGGCAGG TGCTCTGCCG AGGGTCT      8460

ATACAACCCC AGTGCTGCGT GGATTGGGTA TCTAATACAT CACTACCCAT GTTTGTG      8520

TAGCCGTGTG TTGGCTGTCC ATTTCATGGA GCAGATGCTC TTTGAGGACA AACTTCC      8580

GACTGTGACC TTTGACTGGT ATGGGAAAAA TTATACGGTG CCTGTAGAAG ATCTGCC      8640

CATCATTGCT GGTGTGCACG GTATTGAGGC TTTCTCGGTG GTGCGCTACA CCAACGC      8700

GATCCTCAGA GTTTCCCAAT CACTAACAGA CATGACCATG CCCCCCCTGC GAGCCTG      8760

AAAGAAAGCC AGGGCGGTCC TCGCCAGCGC CAAGAGGCGT GGCGGAGCAC ACGCAAA      8820

GGCTCGCTTC CTTCTCTGGC ATGCTACATC TAGACCTCTA CCAGATTTGG ATAAGAC      8880

CGTGGCTCGG TACACCACTT TCAATTATTG TGATGTTTAC TCCCCGGAGG GGGATGT      8940

TGTTACACCA CAGAGAAGAT TGCAGAAGTT TCTTGTGAAG TATTTGGCTG TCATTGT      9000

TGCCCTAGGG CTCATTGCTG TTGGACTAGC CATCAGCTGA ACCCCAAAT TCAAAAT       9060

TTAACAGTTT TTTTTTTTTT TTTTTTTTTT TTTTAGGGCA GCGGCAACAG GGGAGAC      9120

GGGCTTAACG ACCCCGCGAT GTG                                          9143
```

REAGENTS AND METHODS USEFUL FOR CONTROLLING THE TRANSLATION OF HEPATITIS GBV PROTEINS

RELATED APPLICATIONS

This application is a continuation of U.S. Ser. No. 08/639,857, now abandoned, which is a continuation-in-part of U.S. Ser. No. 08/580,038, filed Dec. 21, 1995, now U.S. Pat. No. 5,867,670 which is a continuation-in-part application of, and claimed the benefit of, U.S. provisional application Serial No. 60/002,265 filed Aug. 14, 1995, which is related to patent application U.S. Ser. No. 60/002,255 filed Aug. 14, 1995, which is related to patent applications U.S. Ser. No. 08/480,995 filed Jun. 7, 1995, now abandoned, U.S. Ser. No. 08/473,475 filed Jun. 7, 1995, now U.S. Pat. No. 5,843,450 and U.S. Ser. No. 08/417,629, filed Apr. 6, 1995, which are continuation-in-part applications of U.S. Ser. No. 08/424,550 filed Jun. 5, 1995, which is a continuation-in-part application of U.S. Ser. No. 08/377,557 filed Jan. 30, 1995, now abandoned, which is a continuation-in-part of U.S. Ser. No. 08/344,185 filed Nov. 23, 1994, now abandoned and U.S. Ser. No. 08/344,190 filed Nov. 23, 1994, now abandoned which are each continuation-in-part applications of U.S. Ser. No. 08/283,314 filed Jul. 29, 1994, now abandoned which is a continuation-in-part application of U.S. Ser. No. 08/242,654, filed May 13, 1994, now abandoned which is a continuation-in-part application of U.S. Ser. No. 08/196,030 filed Feb. 14, 1994, now abandoned, all of which enjoy common ownership and each of which is incorporated herein by reference.

BACKGROUND OF THE INVENTION

This invention relates generally to the family of hepatitis GB viruses (HGBV) and more particularly, relates to reagents such as antisense nucleic acid sequences and methods utilizing these nucleic acid sequences which are useful for controlling translation of HGBV-A, -B, or -C, both in vivo and in vitro, by either increasing or decreasing the expressions of HGBV-A, -B or -C proteins.

Recently, a new family of flaviviruses detected in patients with clinically diagnosed hepatitis was reported. This new family of viruses has been named the "GB" viruses, after the initials of the patient first infected with the virus. These viruses have been reported by J. N. Simons et al., *Proc. Natl. Acad. Sci. USA* 92:3401–3405 (1995); and J. N. Simons et al., *Nature Medicine* 1(6):564–569 (1995). Three members of the family have been identified to date: GBV-A, GBV-B and GBV-C. T. P. Leary, et al., *J. Med. Virol.* 48:60–67 (1995) While HGBV-A appears at this time to be of non-human primate source, HGBV-C is clearly of human source. Currently, the source of HGBV-B is unknown. These viruses are thought to play a role in transmittable hepatitis disease of viral origin.

The GB viruses appear to be members of the Flaviviridae family. They possess RNA genomes approximately 9.5 kb in size which contain a single long open reading frame (ORF). Structural and nonstructural proteins are encoded in the N-terminal one-third and C-terminal two-thirds of the putative viral polyproteins, respectively. Phylogenetic analyses of the nonstructural helicase and replicase genes demonstrate that these viruses are related to, but distinct from, the HCV genus of the Flaviviridae. See, for example, T. P. Leary, et al., supra and A. S. Muerhoff et al., *J. Virol.* 69:5621–5630 (1995). Specifically, GBV-A and GBV-C appear most closely related as they share a common ancestor, while the GBV-A/C ancestor, GBV-B and HCV all appear to be equally divergent from other members of the Flaviviridae.

However, when the 5' nontranslated regions (NTRs) and structural genes are examined, a more striking division between the GB viruses and the other members of the Flaviviridae becomes apparent. GBV-B appears similar to the HCV and pestivirus genera of the Flaviviridae. Conserved sequences present in the 5' NTRs of HCV and pestiviruses are found in the 5' NTR of GBV-B, and GBV-B and HCV share closely related RNA secondary structures within the 5' NTR. (M. Honda, E. A. Brown and S. M. Lemon, manuscript submitted).

Moreover, a basic (pI=11.1) core protein is present at the N-terminus of the GBV-B putative polyprotein precursor, and two putative envelope glycoproteins with several potential N-linked glycosylation sites arc located downstream of core in GBV-B. A. S. Muerhoff et al., supra. These structural proteins appear in all members of the Flaviviridae examined to date. See, for example, M. S. Collett et al., *J. Gen. Virol.* 69:2637–2643 (1989) and R. H. Miller and R. H. Purcell, *Proc. Natl. Acad. Sci. USA* 87:2057–2061 (1990).

In contrast to GBV-B, examination of GBV-A and GBV-C reveals marked differences between these viruses and other genera of the Flaviviridae. GBV-A and GBV-C contain long 5' NTRs that have limited sequence identity at the 5' NTR to each other but no identity to the 5' NTRs GBV-B, HCV or pestiviruses. GBV-A and GBV-C also encode putative envelope proteins that contain relatively few potential N-linked glycosylation sites. Most strikingly, clearly discernible basic core proteins are not found in the cDNA sequences cloned thus far from these viruses.

The absence of core proteins would distinguish GBV-A and GBV-C from other genera of the Flaviviridae. However, several important aspects of the structure of the GBV-A and GBV-C genomes remain undefined. Primary among these is the identification of the AUG codons at which translation of the viral polyproteins initiate. The sequence of GBV-A contains two potential in-frame initiator AUG codons 27 nucleotides (9 amino acids) and immediately upstream of the putative E1 signal sequence. Similarly, multiple GBV-C sequences possess two to three potential in-frame initiator AUG codons. See, T. P. Leary et al., supra: and J. Linnen et al., *Science* 271:505–508 (1996). However, none of these AUGs have been demonstrated to serve as the initiator codon, and initiation at any of these sites would result in a severely truncated core protein at best. It is conceivable that deletions during the cloning of these virus RNAs could have resulted in the elimination of core sequences or a disruption of the true ORF in this region of the genome, as suggested by Leary et al., supra. However, multiple RT-PCR products generated from the 5' ends of GBV-A and GBV-C using a variety of primers, polymerases and conditions (unpublished data), in addition to determining the 5' end sequences of over 35 separate GBV-C isolates (U.S. Ser. No. 08/580,038, filed Dec. 21, 1995, previously incorporated herein by reference) provide no support for the existence of additional sequence missing from the previously described cDNA clones. Thus, it is possible that the 5' ends of these viruses are complete (or nearly complete), and that GBV-A and GBV-C do not encode core proteins.

Of the genera that comprise the Flaviviridae, the viruses classified in the flaviviruses genus (e.g., yellow fever virus, dengue virus) contain relatively short 5' NTRs of 97 to 119 nucleotides. In these viruses, translational initiation is thought to utilize a conventional eukaryotic ribosome scanning mechanism in which ribosomes bind the RNA at a 5' cap structure and scan in a 3' direction until encountering an AUG codon in a favorable context for initiation. See, M. Kozak, Cell 44:283–292 (1989) and M. Kozak, *J. Cell. Biol.* 108:229–241 (1989).

In contrast to the flavivirus genus, genomic RNAs from members of the pestiviruses and HCV genera contain relatively long 5' NTRs of 341 to 385 nucleotides which in some ways are similar to those of picornaviruses. Extensive studies of the picornavirus 5' NTRs reveal that translation initiation occurs through a mechanism of internal ribosome entry. R. J. Jackson et al., *Mol. Biol. Reports* 19:147–159 (1994); K. Meerovitch and N. Sonnenberg, *Semin. Virol.* 67:3798–3807 (1993). This internal entry requires a defined segment of the viral 5' NTR known as an "internal ribosome entry site" (IRES) or "ribosome landing pad." The RNA comprising the cis-acting IRES forms highly ordered structures which interact with trans-acting cellular translation factors to bind the 40S ribosome subunit at an internal site on the viral message, often many hundreds of nucleotides downstream of the 5' end of the molecule. Such translation initiation functions in a 5' cap-independent fashion, and is generally not influenced by structure or sequence upstream of the IRES.

Practically, the ability of a sequence to function as an IRES is assessed by insertion of the sequence between two cistrons of a bicistronic RNA. If the intercistronic sequence contains an IRES, there is significant translation of the downstream cistron which is generally independent of the translational activity of the upstream cistron. Studies of the 5' NTRs of HCV and pestiviruses using bicistronic mRNAs demonstrate the presence of IRESs in these sequences. See, for example, T. L. Poole et al., *Virology* 206:750–754 (1995); R. Rijnbrand et al., *FEBS Letters* 365:115–119 (1995); K. Tsukiyama-Kohara et al., *J. Virol.* 66:1476–1483 (1992); and C. Wang et al., *J. Virol.* 67:3338–3344 (1993).

Structural changes in the IRES influence the rate of translation initiation. Thus, by modifying a virus' s IRES, one can control the amount of viral protein being made. Control of the translation process of the nucleic acids of GB viruses could provide an effective means of treating viral disease. The ability to control translation could result in a decrease of the expression of viral proteins. Also, the ability to increase expression may prove useful by producing greater amounts of GB viral proteins which could be utilized in a variety of ways, both diagnostically and therapeutically. Further, the ability to increase translation of the GB viruses in vivo may provide a means for increasing immune stimulation in an individual.

It therefore would be advantageous to provide reagents and methods for controlling the translation of HGBV proteins from HGBV nucleic acids. Such reagents would comprise antisense nucleic acid sequences or other compound which may specifically destabilize (or stabilize) the IRES structure. Such nucleic acid sequences or compounds could greatly enhance the ability of the medical community to provide a means for treating an individual infected with GB virus(es). In addition, IRESs are among the most highly consereved nuclcotide sequences. Identification of such a sequence immediately suggests a target for probe-based detection reagents. Diagnostic or screening tests developed from these reagents could provide a safer blood and organ supply by helping to eliminate GBV in these blood and organ donations, and could provide a better understanding of the prevalence of HGBV in the population, epidemiology of the disease caused by HGBV and the prognosis of infected individuals. Additionally, these consereved structures may provide a means for purifying GBV proteins for use in diagnostic assays.

SUMMARY OF THE INVENTION

The present invention provides unique reagents comprising nucleic acid sequences for HGBV-A, -B or -C that are useful for controlling the translation of HGBV nucleic acids to proteins. These nucleic acid sequences may be DNA or RNA, derivatized DNA or RNA, PNA in both the antisense or sense orientations.

The present invention also provides a method for controlling the translation of HGBV nucleic acids to HGBV proteins, comprising contacting a first nucleic acid sequence with HGBV nucleic acid sequence under conditions which permit hybridization of the first nucleic acid sequence and the HGBV nucleic acid sequence, and altering the level of translation of the HGBV nucleic acid. The first nucleic acid sequence is an antisense nucleic acid sequence which is substantially complementary to a sequence of the sense strand within the 5' NTR region of the HGBV nucleic acid sequence. The sense strand is of genomic or messenger RNA that is subjected to the translation process. The method described herein is performed in an individual infected with HGBV.

The present invention also provides a method of enhancing the translation of a nucleic acid comprising operably linking a nucleic acid with a nucleic acid having a sequence corresponding to the sequence of GBV-A, -B or -C 5' region, to form a combined nucleic acid capable of being translated.

Further, the invention herein provides a composition for enhancing the translation of a nucleic acid, which composition comprises a nucleic acid having a sequence corresponding to the sequence of GBV-A, -B, or -C 5' region, for operable linkage to nucleic acid to be translated. Further, a composition for controlling translation of hepatitis GB virus -A, -B, or -C from GBvirus -A, -B or -C nucleic acids is provided, which comprises a first non-naturally occurring nucleic acid having a sequence complementary to, or capable of being transcribed to form, a nucleic acid having a sequence complementary to, a sequence of the sense strand within the 5' -NTR region of HGBV-A, -B, or -C, wherein said first nucleic acid comprises a sequence selected from the 5' NTR region of GBV-A, -B, or -C, and a cleavage arc at which the full length GBV-A, -B, or -C RNA is cleaved to form a subgenomic HGBV-A, -B, or -C RNA. The first nucleic acid can be a nucleic acid analog, and it can be linked to a cholesteryl moiety at the 3' end.

BRIEF DESCRIPTION OF THE DRAWINGS

FIG. 5A presents a schematic of the monocistronic templates and FIG. 5B presents a PhosphorImager scan of IVTT products generated with pA15-665/CAT (lane 2), pA15-629/CAT (lane 3), pA15-596/CAT (lane 4), pC1-592/CAT (lane 6), pC1-553/CAT (lane 7) and pC1-526/CAT (lane 8). Control reactions are shown in lanes 1 (pA15-707/CAT), 5 (pC1-631/CAT) and 9 (pHAV-CAT1).

FIGS. 6A and 6B show the translation of bicistronic GBV and HCV vectors, wherein FIG. 6A presents a schematic of the bicistronic T7 templates, and FIG. 6B presents the luciferase activity (Luc-A, light units ×10⁻³), luciferase protein (Luc-P, band volume ×10⁻³) and protein production of IVTTs programmed with the bicistronic vectors.

DETAILED DESCRIPTION OF THE INVENTION

Figure 1:
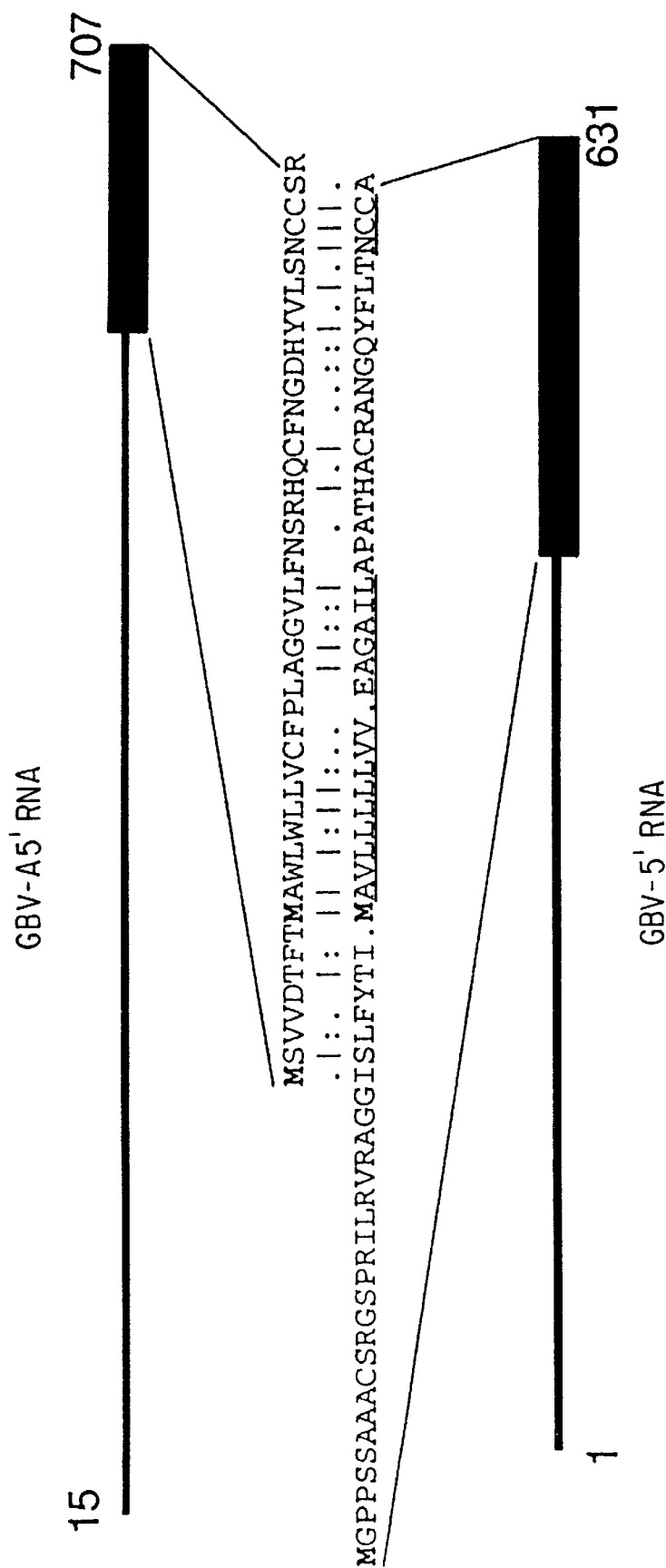
FIG. 1 presents the alignment of GBV-A and GBV-C 5' sequences and amino acid alignment of their respective ORF's. The putative E1 signal sequence in GBV-C and the Asn-Cys-Cys motif are underlined.

The present invention provides reagents and methods useful for controlling the translation of HGBV-A, HGBV-B or HGBV-C nucleic acid to protein.

The term "Hepatitis GB Virus" or "HGBV", as used herein, collectively denotes a viral species which causes non-A, non-B, non-C, non-D, non-E hepatitis in man, and attenuated strains or defective interfering particles derived therefrom. This may include acute viral hepatitis transmitted by contaminated foodstuffs, drinking water, and the like; hepatitis due to HGBV transmitted via person to person contact (including sexual transmission, respiratory and parenteral routes) or via intraveneous drug use. The methods as described herein will allow the treatment of individuals who have acquired HGBV. Individually, the HGBV isolates are specifically referred to as "HGBV-A", "HGBV-B" and "HGBV-C." As described herein, the HGBV genome is comprised of RNA. Analysis of the nucleotide sequence and deduced amino acid sequence of the HGBV reveals that viruses of this group have a genome organization similar to that of the Flaviridae family. Based primarily, but not exclusively, upon similarities in genome organization, the International Committee on the Taxonomy of Viruses has recommended that this family be composed of three genera: Flavivirus, Pestivirus, and the hepatitis C group. Similarity searches at the amino acid level reveal that the hepatitis GB virus subclones have some, albeit low, sequence resemblance to hepatitis C virus. It now has been demonstrated that HGBV-C is not a genotype of HCV. See, for example, U.S. Ser. No. 08/417,629, filed Apr. 6, 1995, previously incorporated herein by reference.

The term "similarity" and/or "identity" are used herein to describe the degree of relatedness between two polynucleotides or polypeptide sequences. The techniques for determining amino acid sequence "similarity" and/or "identity" are well-known in the art and include, for example, directly determining the amino acid sequence and comparing it to the sequences provided herein; determining the nucleotide sequence of the genomic material of the putative HGBV (usually via a cDNA intermediate), and determining the amino acid sequence encoded therein, and comparing the corresponding regions. In general, by "identity" is meant the exact match-up of either the nucleotide sequence of HGBV and that of another strain(s) or the amino acid sequence of HGBV and that of another strain(s) at the appropriate place on each genome. Also, in general, by "similarity" is meant the exact match-up of amino acid sequence of HGBV and that of another strain(s) at the appropriate place, where the amino acids are identical or possess similar chemical and/or physical properties such as charge or hydrophobicity. The programs available in the Wisconsin Sequence Analysis Package, Version 8 (available from the Genetics Computer Group, Madison, Wis., 53711), for example, the GAP program, are capable of calculating both the identity and similarity between two polynucleotide or two polypeptide sequences. Other programs for calculating identity and similarity between two sequences are known in the art.

Additionally, the following parameters are applicable, either alone or in combination, in identifying a strain of HGBV-A, HGBV-B or HGBV-C. It is expected that the overall nucleotide sequence identity of the genomes between HGBV-A, HGBV-B or HGBV-C and a strain of one of these hepatitis GB viruses will be about 45% or greater, since it is now believed that the HGBV strains may be genetically related, preferably about 60% or greater, and more preferably, about 80% or greater.

Also, it is expected that the overall sequence identity of the genomes between HGBV-A and a strain of HGBV-A at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence. Also, it is expected that the overall sequence identity of the genomes between HGBV-B and a strain of HGBV-B at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence. Also, it is expected that the overall sequence identity of the genomes between HGBV-C and a strain of HGBV-C at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence.

A polynucleotide "derived from" a designated sequence for example, the HGBV cDNA, or from the HGBV genome, refers to a polynucleotide sequence which is comprised of a sequence of approximately at least about 6 nucleotides, is preferably at least about 8 nucleotides, is more preferably at least about 10–12 nucleotides, and even more preferably is at least about 15–20 nucleotides corresponding, i.e., similar to or complementary to, a region of the designated nucleotide sequence. Preferably, the sequence of the region from which the polynucleotide is derived is similar to or complementary to a sequence which is unique to the HGBV genome. Whether or not a sequence is complementary to or similar to a sequence which is unique to an HGBV genome can be determined by techniques known to those skilled in the art. Comparisons to sequences in databanks, for example, can be used as a method to determine the uniqueness of a designated sequence. Regions from which sequences may be derived include but are not limited to regions encoding specific epitopes, as well as non-translated and/or non-transcribed regions.

The derived polynucleotide will not necessarily be derived physically from the nucleotide sequence of HGBV, but may be generated in any manner, including but not limited to chemical synthesis, replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, either by methylation and/or by capping, and unmodified forms of the polynucleotide.

The terms "polynucleotide," "oligomer," "oligonucleotide," "oligo" and "primer" are used interchangeably herein.

"HGBV containing a sequence corresponding to a cDNA" means that the HGBV contains a polynucleotide sequence which is similar to or complementary to a sequence in the designated DNA. The degree of similarity or complementarity to the cDNA will be approximately 50% or greater, will preferably be at least about 70%, and even more preferably will be at least about 90%. The sequence which corresponds will be at least about 70 nucleotides, preferably at least about 80 nucleotides, and even more preferably at least about 90 nucleotides in length. The correspondence between the HGBV and the cDNA can be determined by methods known in the art, and include, for example, a direct comparison of the sequenced material with the cDNAs described, or hybridization and digestion with single strand nucleases, followed by size determination of the digested fragments.

"Purified viral polynucleotide" refers to an HGBV genome or fragment thereof which is essentially free, i.e., contains less than about 50%, preferably less than about 70%, and even more preferably, less than about 90% of polypeptides with which the viral polynucleotide is naturally associated. Techniques for purifying viral polynucleotides are well known in the art and include, for example, disruption of the particle with a chaotropic agent, and separation of the polynucleotide(s) and polypeptides by ion-exchange chromatography, affinity chromatography, and sedimentation according to density. Thus, "purified viral polypeptide" means an HGBV polypeptide or fragment thereof which is essentially free, that is, contains less than about 50%, preferably less than about 70%, and even more preferably, less than about 90% of cellular components with which the viral polypeptide is naturally associated. Methods for purifying are known to the routineer.

"Polypeptide" as used herein indicates a molecular chain of amino acids and does not refer to a specific length of the product. Thus, peptides, oligopeptides, and proteins are included within the definition of polypeptide. This term, however, is not intended to refer to post-expression modifications of the polypeptide, for example, glycosylations, acetylations, phosphorylations and the like.

A "polypeptide" or "amino acid sequence" derived from a designated nucleic acid sequence or from the HGBV genome refers to a polypeptide having an amino acid sequence identical to that of a polypeptide encoded in the sequence or a portion thereof wherein the portion consists of at least 3 to 5 amino acids, and more preferably at least 8 to 10 amino acids, and even more preferably 15 to 20 amino acids, or which is immunologically identifiable with a polypeptide encoded in the sequence.

A "recombinant polypeptide" as used herein means at least a polypeptide of genomic, semisynthetic or synthetic origin which by virtue of its origin or manipulation is not associated with all or a portion of the polypeptide with which it is associated in nature or in the form of a library and/or is linked to a polynucleotide other than that to which it is linked in nature. A recombinant or derived polypeptide is not necessarily translated from a designated nucleic acid sequence of HGBV or from an HGBV genome. It also may be generated in any manner, including chemical synthesis or expression of a recombinant expression system, or isolation from mutated HGBV.

The term "synthetic peptide" as used herein means a polymeric form of amino acids of any length, which may be chemically synthesized by methods well-known to the routineer. These synthetic peptides are useful in various applications.

"Recombinant host cells," "host cells," "cells," "cell lines," "cell cultures," and other such terms denoting microorganisms or higher eucaryotic cell lines cultured as unicellular entities refer to cells which can be, or have been, used as recipients for recombinant vector or other transfer DNA, and include the original progeny of the original cell which has been transfected.

As used herein "replicon" means any genetic element, such as a plasmid, a chromosome or a virus, that behaves as an autonomous unit of polynucleotide replication within a cell. That is, it is capable of replication under its own control.

A "vector" is a replicon in which another polynucleotide segment is attached, such as to bring about the replication and/or expression of the attached segment.

The term "control sequence" refers to polynucleotide sequences which are necessary to effect the expression of coding sequences to which they are ligated. The nature of such control sequences differs depending upon the host organism. In prokaryotes, such control sequences generally include promoter, ribosomal binding site and terminators; in eukaryotes, such control sequences generally include promoters, terminators and, in some instances, enhancers. The term "control sequence" thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences.

The term "open reading frame" or "ORF" refers to a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

The term "immunologically identifiable with/as" refers to the presence of epitope(s) and polypeptide(s) which also are present in and are unique to the designated polypeptide(s), usually HGBV proteins. Immunological identity may be determined by antibody binding and/or competition in binding. These techniques are known to the routineer and also are described herein. The uniqueness of an epitope also can be determined by computer searches of known data banks, such as GenBank, for the polynucleotide sequences which encode the epitope, and by amino acid sequence comparisons with other known proteins.

As used herein, "epitope" means an antigenic determinant of a polypeptide. Conceivably, an epitope can comprise three amino acids in a spatial conformation which is unique to the epitope. Generally, an epitope consists of at least five such amino acids, and more usually, it consists of at least eight to ten amino acids. Methods of examining spatial conformation are known in the art and include, for example, x-ray crystallography and two-dimensional nuclear magnetic resonance.

The term "individual" as used herein refers to vertebrates, particularly members of the mammalian species and includes but is not limited to domestic animals, sports animals, primates and humans; more particularly the term refers to tamarins and humans.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an HGBV epitope" means naturally occurring HGBV polypeptides or fragments thereof, as well as polypeptides prepared by other means, for example, chemical synthesis or the expression of the polypeptide in a recombinant organism.

The term "transformation" refers to the insertion of an exogenous polynucleotide into a host cell, irrespective of the method used for the insertion. For example, direct uptake, transduction, or f-mating are included. The exogenous polynucleotide may be maintained as a non-integrated vector, for example, a plasmid, or alternatively, may be integrated into the host genome.

"Treatment" refers to prophylaxis and/or therapy.

The term "plus strand" (or "+") as used herein denotes a nucleic acid that contains the sequence that encodes the polypeptide. The term "minus strand" (or "−") denotes a nucleic acid that contains a sequence that is complementary to that of the "plus" strand.

"Positive stranded genome" of a virus denotes that the genome, whether RNA or DNA, is single-stranded and encodes a viral polypeptide(s).

The term "test sample" refers to a component of an individual's body which is the source of the analyte (such as, antibodies of interest or antigens of interest). These components are well known in the art. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitorurinary tracts, tears, saliva, milk, white blood cells, myelomas and the like; biological fluids such as cell culture supernatants; fixed tissue specimens; and fixed cell specimens.

"Purified HGBV" refers to a preparation of HGBV which has been isolated from the cellular constituents with which the virus is normally associated, and from other types of viruses which may be present in the infected tissue. The techniques for isolating viruses are known to those skilled in the art and include, for example, centrifugation and affinity chromatography.

"PNA" denotes a "peptide nucleic analog" which may be utilized in various diagnostic, molecular or therapeutic methods. PNAs are neutrally charged moieties which can be directed against RNA or DNA targets. PNA probes used in assays in place of, for example, DNA probes, offer advantages not achievable when DNA probes are used. These advantages include manufacturability, large scale labeling, reproducibility, stability, insensitivity to changes in ionic strength and resistance to enzymatic degradation which is present in methods utilizing DNA or RNA. These PNAs can be labeled with such signal generating compounds as fluorescein, radionucleotides, chemiluminescent compounds, and the like. PNAs or other nucleic acid analogs such as morpholino compounds thus can be used in various methods in place of DNA or RNA. It is within the scope of the routineer that PNAs or morpholino compounds can be substituted for RNA or DNA with appropriate changes if and as needed in reagents and conditions utilized in these methods.

The detection of HGBV in test samples can be enhanced by the use of DNA hybridization assays which utilize DNA oligomers as hybridization probes. Since the amount of DNA target nucleotides present in a test sample may be in minute amounts, target DNA usually is amplified and then detected. Methods for amplifying and detecting a target nucleic acid sequence that may be present in a test sample are well-known in the art. Such methods include the polymerase chain reaction (PCR) described in U.S. Pat. Nos. 4,683,195 and 4,683,202 which are incorporated herein by reference, the ligase chain reaction (LCR) described in EP-A-320 308, gap LCR (GLCR) described in European Patent Application EP-A-439 182 and U.S. Pat. No. 5,427,930 which are incorporated herein by reference, multiplex LCR described in International Patent Application No. WO 93/20227, NASBA and the like. These methods have found widespread application in the medical diagnostic field as well as in the fields of genetics, molecular biology and biochemistry.

The reagents and methods of the present invention are made possible by the provision of a family of closely related nucleotide sequences present in the plasma, serum or liver homogenate of an HGBV infected individual, either tamarin or human. This family of nucleotide sequences is not of human or tamarin origin, since it hybridizes to neither human nor tamarin genomic DNA from uninfected individuals, since nucleotides of this family of sequences are present only in liver (or liver homogenates), plasma or serum of individuals infected with HGBV. In addition, the family of sequences has shown no significant identity at the nucleic acid level to sequences contained within the HAV, HBV, HCV, HDV and HEV genome, and low level identity, considered not significant, as translation products. Infectious sera, plasma or liver homogenates from HGBV infected humans contain these polynucleotide sequences, whereas sera, plasma or liver homogenates from non-infected humans has not contained these sequences. Northern blot analysis of infected liver with some of these polynucleotide sequences has demonstrated that they are derived from a large RNA transcript similar in size to a viral genome. Sera, plasma or liver homogenates from HGBV-infected humans contain antibodies which bind to this polypeptide, whereas sera, plasma or liver homogenates from non-infected humans do not contain antibodies to this polypeptide; these antibodies are induced in individuals following acute non-A, non-B, non-C, non-D and non-E hepatitis infection. By these criteria, it is believed that the sequence is a viral sequence, wherein the virus causes or is associated with non-A, non-B, non-C, non-D and non-E hepatitis.

Using determined portions of the isolated HGBV nucleic acid sequences as a basis, oligomers of approximately eight nucleotides or more can be prepared, either by excision or synthetically, which hybridize with the HGBV genome and are useful in identification of the viral agent(s), further characterization of the viral genome, as well as in detection of the virus(es) in diseased individuals. The natural or derived probes for HGBV polynucleotides are a length which allows the detection of unique viral sequences by hybridization. While six to eight nucleotides may be a workable length, sequences of ten to twelve nucleotides are preferred, and those of about 20 nucleotides may be most preferred. These sequences preferably will derive from regions which lack heterogeneity. These probes can be prepared using routine, standard methods including automated oligonucleotide synthetic methods. A complement of any unique portion of the HGBV genome will be satisfactory. Complete complementarity is desirable for use as probes, although it may be unnecessary as the length of the fragment is increased.

Synthetic oligonucleotides may be prepared using an automated oligonucleotide synthesizer such as that described by Warner, *DNA* 3:401 (1984). If desired, the synthetic strands may be labeled with $^{32}$P by treatment with polynucleotide kinase in the presence of $^{32}$P-ATP, using standard conditions for the reaction. DNA sequences including those isolated from genomic or cDNA libraries, may be modified by known methods which include site directed mutagenesis as described by Zoller, *Nucleic Acids Res.* 10:6487 (1982). Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. Culture of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions suitable for hybridization with the correct strand, but not with the unmodified sequence. The sequences which have been identified by hybridization are recovered and cloned.

Polymerase chain reaction (PCR) and ligase chain reaction (LCR) are techniques for amplifying any desired nucleic acid sequence (target) contained in a nucleic acid or mixture thereof. In PCR, a pair of primers are employed in excess to hybridize at the outside ends of complementary strands of the target nucleic acid. The primers are each extended by a polymerase using the target nucleic acid as a template. The extension products become target sequences themselves, following dissociation from the original target strand. New primers are then hybridized and extended by a polymerase, and the cycle is repeated to geometrically increase the number of target sequence molecules. PCR is disclosed in U.S. Pat. Nos. 4,683,195 and 4,683,20, previously incorporated herein by reference.

LCR is an alternate mechanism for target amplification. In LCR, two sense (first and second) probes and two antisense (third and fourth) probes are employed in excess over the target. The first probe hybridizes to a first segment of the target strand and the second probe hybridizes to a second segment of the target strand, the first and second segments being positioned so that the primary probes can be ligated into a fused product. Further, a third (secondary) probe can hybridize to a portion of the first probe and a fourth (secondary) probe can hybridize to a portion of the second probe in a similar ligatable fashion. If the target is initially double stranded, the secondary probes will also hybridize to the target complement in the first instance. Once the fused strand of sense and antisense probes are separated from the target strand, it will hybridize with the third and fourth probes which can be ligated to form a complementary, secondary fused product. The fused products are functionally equivalent to either the target or its complement. By repeated cycles of hybridization and ligation, amplification of the target sequence is achieved. This technique is described in EP-A-320,308, hereby incorporated by reference. Other aspects of LCR technique are disclosed in EP-A-439,182, which is incorporated herein by reference.

The 5'-NTR region of HGBV-A is approximately 592 nucleotides long (SEQUENCE ID NO 23). This region in HGBV-B is approximately 445 nucleotides long (SEQUENCE ID NO 32), and the 5' NTR region of HGBV-C is approximately 533 nucleotides in length (SEQUENCE ID NO 4). To functionally characterize the 5' ends of GBV-A and GBV-C RNAs, the sites and mechanism of translation initiation of both monocistronic and bicistronic RNAs were examined in a cell-free in vitro translation system. Weak IRES elements were found to be present in the 5' RNAs of GBV-A and GBV-C suggesting that these sequences are complete or nearly complete. In addition, the position of the initiating AUG codons in the monocistronic RNAs, and presumably in the viral genomic RNA as well, demonstrated that GBV-A and GBV-C do not contain core proteins at the N-termini of their polyproteins. Thus, GBV-A and GBV-C appear unique from other members of the Flaviviridae and may constitute a separate group within this family. Consistent with this hypothesis, we also discovered that the secondary structures of the 5' ends of these viruses are different from the conserved structures present in the 5' NTRs of the pestiviruses, HCV and GBV-B.

The present invention provides nucleic acids that are capable of interacting with distinct cis-acting control elements of HGBV and thus are capable of blocking, enhancing or suppressing the translation of HGBV nucleic acids.

In a first embodiment, a method for controlling the translation of HGBV nucleic acids to proteins is provided. This method comprises the steps of contacting a first non-naturally occurring nucleic acid with HGBV nucleic acid. This first nucleic acid has a sequence that is complementary to a sequence of the sense strand within the 5' NTR region of HGBV-A, -B or -C. This first nucleic acid is contacted with an HGBV nucleic acid for times and under conditions suitable for hybridization to occur, and thus form a hybridization product. The hybridization results in the alteration of the level of translation of the HGBV nucleic acid.

The antisense nucleic acid of the present invention is RNA, DNA or a modified nucleic acid such as a PNA or morpholino compound, degradation-resistant sulfurized and thiophosphate derivatives of nucleic acids, and the like. Modified nucleic acids preferably will be able to increase the intracellular stability and/or permeability of the nucleic acid, increase the affinity of the nucleic acid for the sense strand or decrease the toxicity of the nucleic acid. Such advantages are well known in the art, and are described in, for example, S. T. Crooke et al., eds., *Antisense Research and Applications,* CRC Press (1993).

Antisense nucleic acids thus can be modified or altered to contain modified bases, sugars or linkages, be delivered in specialized systems such as liposomes or by gene therapy, or may have attached moieties. Such attached moieties, such as hydrophobic moieties such as lipids and in particular, cholesterols, can enhance the interaction of the nucleic acid with cell membranes. In addition, such attached moieties can act as charge neutralizers of the phosphate backbone (for example, polycationic moieties such as polylysine). These moieties can be attached at either the 5' or the 3' end of the nucleic acids, and also can be attached through a base, sugar or internucleotide linkage. Other moieties can act as capping groups which are specifically placed at the 3' or the 5' ends of the nucleic acids to prevent exonucease degradation. These capping groups include, for example, hydroxyl protecting groups including glycols such a polyethylene glycols (PEG), tetraethylene glycol (TEG) and the like.

The first nucleic acid will have at least 10 nucleotides in a sequence substantially complementary to a sequence of the sense strand within the 5' NTR region of HGBV-A, -B, or -C. Preferably, the first nucleic acid has about 12 nucleotides in such a complementary sequence; more preferably, the first nucleic acid has about 15 nucleotides; and still more preferably, the first nucleic acid has about 20 nucleotides. It is preferred that such a first nucleic acid have less than 100 nucleotides in such a complementary sequence, and more preferably, a first nucleic acid will have less than 50 nucleotides. Most preferably, the first nucleic acid will have between 20 to 30 nucleotides that are capable of forming a stable hybridization product with a sense sequence of the 5' NTR region of HGBV-A, -B or -C.

The 5' NTR region of HGBV-A is set forth in SEQUENCE ID NO 23; the 5' NTR region of HGBV-B is set forth in SEQUENCE ID NO 32; and the 5' NTR region of HGBV-C is set forth in SEQUENCE ID NO 4. The nucleic acid can be placed in the cell through several ways known to those in the art. For example, cells can be transfected with a second nucleic acid capable of generating the first nucleic acid as a transcription product (for example, by including the second nucleic acid in a viral carrier as detailed by U.S. Pat. No. 4,493,002, incorporated herein by reference, or by gene therapy methods such as including the second nucleic acid in a retroviral vector). Gene therapy methods are known to those of skill in the art.

The present invention further encompasses means for placing the first nucleic acid or the second nucleic acid into cells infected with HGBV-A, -B or -C or into cells which are to be protected from HGBV infection. Examples of such means include but are not limited to vectors, liposomes and lipid suspensions, such as N-(1-(2,3-dioleoyloxy)propul)-N,N,N-thrimethylammonium methylsulfate (DOTAP), N-[1-(2,3-dioleyloxy)propul]-N,N,N-trimethylammonium chloride (DOTMA), and the like. The lipid may be covalently linked directly to the first nucleic acid in an alternative embodiment.

The antisense nucleic acid also may be linked to moieties that increase cellular uptake of the nucleic acid. Such moieties may be hydrophobic (such as, phospholipids or lipids such as steroids [for example, cholesterol]) or may be polycationic moieties that are attached at any point to the antisense nucleic acid, including at the 5' or 3' ends, base, sugar hydroxyls and internucleoside linkages. A moiety known to increase uptake is a cholesteryl group, which may be attached through an activated cholesteryl chloroformate or cholic acid, by means known in the art.

Further, enhancement of translation may allow for stronger immune responses. Blocking or decreasing translation of viral nucleic acid may decrease the pathology of the viral infection.

Nucleic acid or nucleic acid analogs can be provided as compositions for pharmaceutical administration. Injection preparations and suppositories may usually contain 1–10 mg of the nucleic acid or nucleic acid analog per dose (ampule or capsule). For humans the daily dose of about 0.1 to 1000 mg, preferably 1–100 mg (from about 10–20 mg/kg to 1000 to 2000 mg/kg body weight) is the daily dosage. As is known to those in the art, however, a particular dose for a particular individual depends on a variety of factors, including but not limited to, effectiveness of the particular nucleic acid or nucleic acid analog used, the age, weight and general state of health of the individual, the diet and sex of the individual, the mode of administration of the dosage, the rate of elimination and half life of the composition, whether this composition is used in combination with other medications and the clinical severity of the individual's disease. Such compositions which are pharmaceutical articles of manufacture include articles whose active ingredients are contained in an effective amount of attain the intended purpose. A preferred range has been described hereinabove, and determination of the most effective amounts for treatment of each HGBV infection is well within the skill of the rountineer.

In addition to the nucleic acid and nucleic acid analogs of the present invention, contemplated pharmaceutical preparations may contain suitable excipients and auxiliaries which facilitate processing of the active compounds. These preparations can be administered orally, rectally, parenterally, bucally or sublingually. All may contail from 0.1 to 99% by weight of active ingredients, together with an excipient. A preferred method of administration is parenteral, especially intraveneous administration.

Suitable formulations for parenteral administration include aqueous solutions of the active compounds in water-soluble or water-dispersible form. Additionally, suspensions of the active compounds as appropriate oily injection suspensions may be administered. Suitable lipophilic solvents or vehicles include fatty oils (for example, sesame oil or synthetic fatty acid esters such as ethyloleate or triglycerides). Aqueous injection suspensions may contain substances which increase the viscosity of the suspension, for example, sodium carboxymethyl cellulose, sorbitol, and/or dextran. The suspension also may contain stabilizers.

It is within the scope of the present invention that the compositions described herein may be administered encapsulated in liposomes, pharmaceutical compositions wherein the active ingredient is contained either dispersed or variously present in corpuscles consisting of aqueous concentric layers adherent to lipidic layers. Methods of utilizing this technology are known in the art.

The present invention will now be described by way of examples, which are meant to illustrate, but not to limit, the spirit and scope of the invention.

EXAMPLES

Example 1
Internal Ribosome Entry Site in 5' NTR of GBV-B

Several positive strand RNA viruses, such as picornaviruses and pestiviruses, possess large 5' nontranslated regions (NTRs). These large NTRs control the initiation of cap-independent translation by functioning as internal ribosome entry sites (IRESs) (Pelletier and Sonenberg, *Nature* (London) 334:320–325). The IRES is thought to form a specific RNA structure which allows ribosomes to enter and begin translation of an RNA without using the cellular machinery required for cap-dependent translation initiation. The large 5' NTR of HCV has been shown to possess an IRES (Tsukiyama-Kohara et al. J. Virol. 66:1476–1483, 1992; Wang et al. *J. Virol.* 67:3338–3344, 1993; Rijnbrand et al. FEBS Letters 365:115–119, 1995). Due to the high level of sequence conservation between the 5' NTRs of GBV-B and HCV, it was reasoned that GBV-B may also contain an IRES.

To test for IRES function in GBV-B (SEQUENCE ID NO 32), the 5' NTR of this virus was used to replace the 5' NTR of hepatitis A virus (HAV) in the pLUC-HAV-CAT plasmid described by Whetter et al. (*J. Virol.* 68:5253–5263, 1994). The 5' NTR of GBV-B was amplified from a plasmid clone using SEQUENCE ID NO. 58 (UTR-B.1) and SEQUENCE ID. NO. 59 (NTR-B-a1) as primers Briefly, a 50 μl PCR was set up using a Perkin-El mer PCR kit as described by the manufacturer with 1 μM primers, 2 mM MgCl$_2$ and approximately 10 ng of plasmid. This reaction was amplified for 20 cycles (94° C., 20 sec; 55° C., 30 sec; 72° C., 30 sec) followed by a final extension at 72° C. for 10 min. The completed reaction then was held at 4° C. This product was extracted with phenol:chloroform and precipitated as described in the art. The 3' terminal adenosine residues added by the AmpliTaq® polymerase were removed from this product by incubation with T4 DNA polymerase and deoxynucleotide triphosphates as described (Sambrook et al., *Molecular Cloning: A Laboratory Manual,* Cold Spring Harbor Press, 1989). After heat inactivation, the product was digested with Xba I and gel purified as described in the art. The purified product was ligated to pHAV-CAT1 (Whetter et al. *J. Virol.* 68:5253–5263, 1994) that had been cut with HindIII, end-filled with Klenow polymerase and deoxynucleotide triphosphates, heat-inactivated, digested with Xba I, treated with bacterial alkaline phosphatase, extracted with phenol:chloroform, and precipitated as described in the art. The constructed plasmid, pGBB-CAT1, was digested with Sac I, blunt-ended with T4 DNA polymerase and deoxynucleotide triphosphates, heat-inactivated, and digested with Not I as described in the art. The 1.3 kbp product from these reactions was gel purified and cloned into pLUC-HAV-CAT (Whetter et al. *J. Virol.* 68:5253–5263, 1994) that had been digested with HindIII, end-filled with Klenow polymerase and deoxynucleotide triphosphates, heat-inactivated, digested with Not I, treated with bacterial alkaline phosphatase, extracted with phenol:chloroform, and precipitated as described in the art.

The resultant plasmid, pLUC-GBB-CAT was used in in vitro transcription-translation experiments to test for an IRES function.

An in vitro transcription-translation assay was performed using the T$_N$T™ T7 coupled reticulocyte lysate system from Promega (Madison, Wis.) as described by the manufacturer. The plasmids tested were pLUC-GBB-CAT (described above), pLUC-HAV-CAT (positive control from Whetter et al. J. Virol. 68:5253–5263, 1994), and pLUC-Δ355–532 (negative control from Whetter et al. *J. Virol.* 68:5253–5263, 1994). The products (labeled with $^{35}$S-methionine) were run on a 10% Laemmli gel as described in the art. The gel was fixed in 10% methanol, 20% acetic acid for 10 minutes, dried down and exposed to a PhosphoImager® screen (Molecular Dynamics, Sunnyvale, Calif.). The products were visualized with the PhosphoImager®. In addition, the reactions were examined for Luc and CAT activity using commercially available kits (Promega, Madison, Wis.) (data not shown).

All three reactions contained luciferase activity and a band consistent with the size expected for luciferase (transcribed from the LUC gene in the plasmid). LUC expression, which is a measure of the level of translation that initiates from the 5' end of the mRNA, appeared to be equivalent in the three reactions. Thus, equivalent amounts of RNA templates were present in a translatable form in these three reactions. The pLUC-HAV-CAT and the pLUC-GBB-CAT reactions also possessed chloramphenicol acetyltransferase (CAT) activity and contained a band consistent with the size expected for CAT (from the CAT gene in the plasmid). This band is not seen in the pLUC-Δ355–532 negative control. CAT expression measures the level of internal translation initiation. Because translation of the CAT gene requires the existence of an IRES in this plasmid construct, the 5' NTR of GBV-B must be providing this function. Therefore, similar to HCV, GBV-B's 5' NTR contains an IRES. Further studies of these plasmids, both in vitro and in vivo are ongoing to better characterize the IRES in GBV-B.

Example 2
Internal Ribosome Entry Site in 5' NTR of GBV-A and -C
A. Plasmids Various monocistronic and bicistronic plasmids were constructed with PCR-amplified sequences of GBV-A and GBV-C. PCRs utilized components of the GeneAmp PCR Kit with AmpliTaq (Perkin-Elmer) as directed by the manufacturer with final reaction concentrations of 1 μM for oligonucleotide primers and 2 mM MgCl$_2$. PCR products were digested with restriction endonucleases, gel purified and cloned using standard procedures as described by J. Sambrook et al., *Molecular Cloning: A Laboratory Manual.* Cold Spring Harbor Laboratory, Cold Spring Harbor (1989). Monocistronic fusions between GBV sequences and bacterial chloramphenicol acetyltransferase (CAT) were generated by replacing the hepatitis A virus (HAV) HindIII/XbaI fragment of pHAV-CAT1 (described by L. E. Whetter et al., J. Virology 68:5253–5263 (1994) with PCR-amplified cDNA from the 5' ends of GBV-A and GBV-C. The bicistronic constructs were generated in pT7/CAT/ICS/Luc, described by D. Macejak et al., in M. A. Brinton et al., eds., New Aspects of Positive-Strand RNA Viruses, American Society for Microbiology, Washington, D.C.,1990, p. 152–157, and provided as a gift by P. Sarnow, in a two step procedure. First, monocistronic fusions between GBV and luciferase (Luc) were constructed by inserting GBV sequences into the HindIII/NcoI-cut pT7/CAT/ICS/Luc. Bicistronic vectors were constructed by cloning the HindIII/ blunt/SacI GBV fragment from these monocistronic vectors into pT7/CAT/ICS/Luc which had been digested with SalI (blunt) and SacI. The sequence of the cloned inserts and ligation junctions were confirmed by dsDNA sequencing (Sequenase 2.0, USB, Cleveland). Nomenclature (e.g. A15-707) describes the source (GBV-A) and range (nts 15 to 707) of sequence incorporated into the various vectors.

GBV-A sequences (GenBank accession no. U22303) were amplified from a plasmid clone. PCRs for the GBV-A monocistronic and bicistronic constructs utilized the sense primer 5'-TATAAT AAGCTTGCCCCGGACCTCCCACCGAG-3' (HindIII site underlined) (SEQUENCE ID NO 5) coupled with 5'-GC TCTAGATCGGGAACAACAATTGGAAAG (SEQUENCE ID NO 6), 5'-GC TCTAGAGCACTGGTGCCGCGAGT (SEQUENCE ID NO 11), 5'-GCTCTAGAGAGGGGGAAGCAAACCA (SEQUENCE ID NO 12) and 5'-GC TCTAGACATGGTGAATGTGTCGACCAC (Xba I sites underlined) (SEQUENCE ID NO 13) for the monocistronic vectors pA15-707/CAT, pA15-665/CAT, pA15-629/CAT and pA15-596/CAT, respectively; and 5' CCATAA TCATGAGGGAACAACAATTGGAAAG (SEQUENCE ID NO 17), 5'-CCATAA TCATGAGCCGCGAGTTGAAGAGCAC (SEQUENCE ID NO 24), and 5' GCCAAGCCATGGTGAATGTG 3' (BspHI or NcoI sites underlined) (SEQUENCE ID NO 25) for the bicistronic vectors pCAT/A15-705/Luc, pCAT/A15-657/Luc and pCAT/A15-596/Luc, respectively. In addition, a GBV-A sequence amplified with 5'-TATAAT AAGCTTGCCGCGAGTTGAAGAGCAC (SEQUENCE ID NO 21) and 5'-CCATAA TCATGAGCCCCGGACCTCCCACCGAG (SEQUENCE ID NO 22) were used to construct pCAT/A657-15/Luc which contain GBV-A sequences in the antisense orientation.

GBV-C sequences were amplified from a plasmid generated during the cloning of GBV-C 5' sequences, as described in U.S. Ser. No. 08/580,038, previously incorporated herein by reference. The sequence of this GBV-C cDNA (nts 1 to 631, SEQUENCE ID NO 4) corresponds to nts 30 to 659 of GenBank accession no. U44402, the longest GBV-C isolate reported to date and nts 13 to 643 of SEQUENCE ID NO.3. PCRs for the GBV-C monocistronic and bicistronic plasmids utilized the sense primer 5'-TATAAT AAGCTTCACTGGGTGCAAGCCCCA (HindIII site underlined) (SEQUENCE ID NO 7) coupled with 5'-GC TCTAGAGGCGCAACAGTTTGTGAGGAA (SEQUENCE ID NO 8),5'-GC TCTAGAACAAGCGTGGGTGGCCGGGG (SEQUENCE ID NO 14),5'-GC TCTAGAGACCACGAGAAGGAGCAGAAG (SEQUENCE ID NO 15) and 5'-GC TCTAGACATGATGGTATAGAAAAGAG (Xba I site underlined) (SEQUENCE ID NO 16) for the monocistronic vectors pC1-631/CAT, pC1-592/CAT, pC1-553/CAT and pC1-526/CAT, respectively; and 5'-CATG CCATGGCGCAACAGTTTGTGAGGAA (SEQUENCE ID NO 18),5'-GTATTGCG CCATGGCTCGACAAGCGTGGGTGGCCGGGG (SEQUENCE ID NO 26), and 5'-GGACTG CCATGGTGGTATAGAAAAGAG (NcoI sites underlined) (SEQUENCE ID NO 27) for the bicistronic vectors pCAT/C1-629/Luc, pCAT/C1-596/Luc and pCAT/C1-526/Luc, respectively. Additional GBV-C sequences were amplified with 5'-GCTCTAGACACTGGGTGCAAGCCCCA (XbaI site underlined) (SEQUENCE ID NO 9) and 5'-TATAAT AAGCTTGGCGCAACAGTTTGTGAG (HindIII site underlined) (SEQUENCE ID NO 10) for the monocistronic pC631-1/CAT plasmid, and 5'- TATAAT AAGCTTCTCGACAAGCGTGGGTGGCCGGGG 3' (HindIII site underlined) (SEQUENCE ID NO 28) and 5'-GTATTGCG CCATGGCACTGGGTGCAAGCCCCAGAA (NcoI site underlined) (SEQUENCE ID NO 29) for the bicistronic pCAT/C596-1/Luc plasmid. Both of these plasmids contain GBV-C sequences in the antisense orientation.

HCV sequences were amplified from a plasmid clone of a genotype 1a isolate using the sense primer 5'-TATAAT AAGCTTCACTCCCCTGTGAGGAACTAC (HindIII site underlined) (SEQUENCE ID NO 19) coupled with 5'-GTATTGCGTCATGATGGTTTTTCTTTGGGGTTTAG (SEQUENCE ID NO 20) or 5'-CCATAA TCATGATGCACGGTCTACGAGACCT (BspHI sites underlined) (SEQUENCE ID NO 30) to generate the bicistronic vectors pCAT/HCV39-377/Luc and pCAT/HCV39-345/Luc, respectively.

Site-specific nucleotide changes were generated in pA15-707/CAT and pC1-631/CAT using the MORPH™ site-specific plasmid DNA mutagenesis kit (5 Prime→3 Prime, Inc., Boulder, Colo.) as directed by the manufacturer. Nucleotide changes were confirmed by dsDNA sequencing as described above.

B. In vitro Transcription/Translation

In vitro transcription/translation (IVTT) reactions were performed with the TNT™ T7 Coupled Reticulocyte Lysate System (Promega) according to manufacturer's instructions. Reactions (25 μl) contained 20 units rRNasin (Promega), 20 μCi $^{35}$S-cysteine (1000 Ci/mmol, Amersham), and 0.5 μg of plasmid template. After incubation at 30° C. for 60 minutes, 5 μl aliquots were denatured (5 minutes, 99° C.) in an equal volume of 2× SDS/PAGE loading buffer (125 mM Tris, pH 6.8, 4% SDS, 20% glycerol, 10% 2-mercaptoethanol and 0.2 mg/ml bromophenol blue) and electrophoretically separated on 10 to 20% SDS-polyacrylamide gels (Bio-Rad). The gels were fixed in 10% methanol, 20% acetic acid, dried and analyzed with a PhosphorImager SI™ using ImageQuaNT™ software (Molecular Dynamics, Inc.). Image exposure time, white-black range and product quantitations are presented hereinbelow corresponding figure descriptions.

C. Reporter Gene Enzymatic Assays

Luciferase assays were performed by mixing 50 μl of 1× Luciferase Assay Reagent (Promega) with 1 μl of a 10-fold dilution of a rabbit reticulocyte lysate reaction. Activity was assayed immediately by a 5 second count in a Clinilumat LB9502 Luminometer (Berthold Systems Inc., Pittsburgh). CAT assays were completed with a commercially available kit (Promega) according to manufacturer's instructions. Briefly, 5 μl of lysate was incubated with [$^3$H] chloramphenicol and n-butyryl CoA in a 125 μl reaction for one hour at 37° C. Butyrylated [$^3$H]chloramphenicol products were isolated by xylene extraction and quantitated by liquid scintillation counting.

D. Secondary RNA Structure

A model of the secondary structure of the 5' nontranslated RNA of the GBV-C genome was constructed using a combination of phylogenetic and thermodynamic approaches. A first level phylogenetic analysis considered nucleotide sequences representing the 5' RNA of GBV-C strains present in 35 different patient sera, as presented in U.S. Ser. No. 08/580,038, filed Dec. 21, 1995, previously incorporated herein by reference. These were aligned with the program PLEUP (Wisconsin Sequence Analysis Package, version 8, September 1994; Genetics Computer Group, Madison, Wis.) and subjected to a manual search for covariant nucleotide substitutions indicative of conserved helical structures. In addition to canonical Watson-Crick base pairs, G-U base pairs were considered acceptable for this analysis. Conserved helical structures identified by the presence of one or more covariant nucleotide substitutions were forced to base pair in the subsequent computer-based folding of the prototype GBV-C sequence (GenBank accession no. U36380) (SEQUENCE ID NO 3) which used the program MFOLD. Separate MFOLD analyses were carried out with sequences representing nts 1–611, 43–522 (both closed at 273–418), 273–418, and 43–180 of SEQUENCE ID NO 3. MFOLD predicts a series of alternative structures with different predicted folding energies. These were reviewed to determine which predicted structures were most permissive for covariant and noncovariant nucleotide substitutions present in the other GBV-C sequences. Where no predicted structure could accommodate most nucleotide substitutions, the sequence was left single stranded in the final model. A second level phylogenetic analysis involved the alignment of GBV-C sequences with the 5' RNA sequences of 5 separate GBV-A strains (as described in G. G. Schlauder et al., *Lancet* 346:447 [1995] and J. N. Simons et al., *Proc Nat. Acad. Sci. USA* 92:3401–3405 [1995]), followed by a manual search for covariant substitutions indicative of similar structures in the 5' sequences of these related viruses.

E. Results

1. Translation of Monocistronic Transcripts Containing 5' GBV RNA

Figure 2A:
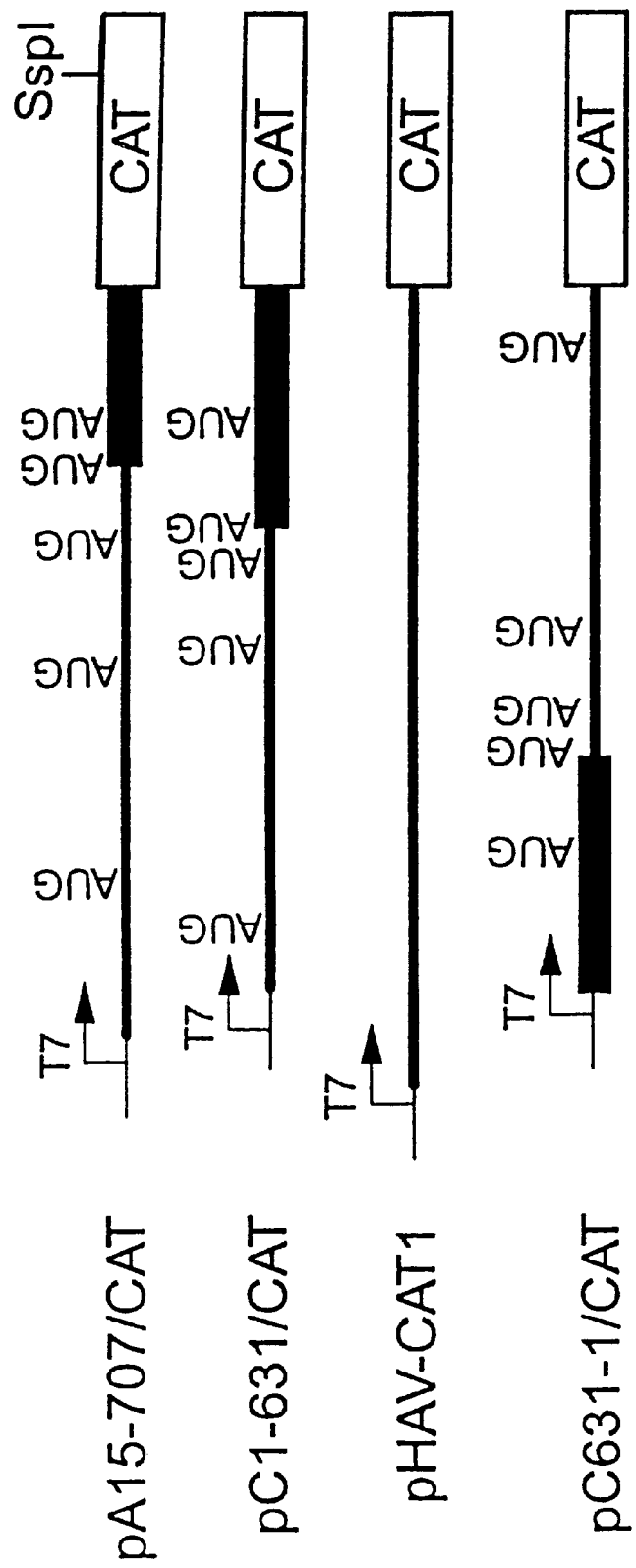
FIG. 2A presents a schematic representation of monocistronic T7 templates, wherein viral RNA sequence is represented as a bold line, the positions of the AUG codons (AUG) and ORFs (box) are indicated.

A common Asn-Cys-Cys motif homologous to the HCV E1 Asn-Ser-Cys motif is found near the N-termini of the putative E1 proteins of GBV-A, GBV-B and GBV-C (T. P. Leary et al., supra and FIG. 1). Located near the N-termini of the GBV-A and GBV-C large ORFs, this tripeptide sequence appears to be the 5' most conserved motif between HCV and the GB viruses. Because it is within the coding regions of GBV-B and HCV and in-frame with the long ORF, this sequence was believed likely to be translated in GBV-A and GBV-C as well. To determine whether the 5' ends of GBV-A and -C could direct translation, nts 15 to 707 of GBV-A (SEQUENCE ID NO 23) and nts 1 to 631 of GBV-C (SEQUENCE ID NO 4) were cloned into plasmid vectors to create pA I 5-707/CAT and pC1-631 /CAT, respectively. These vectors contained a T7 promoter driving transcription of the 5' GBV sequences, which were ligated in-frame (relative to the Asn-Cys-Cys motif) with the bacterial chloramphenicol acetyltransferase (CAT) gene, as shown in FIG. 2A. For GBV-C, only AUGs conserved in all isolated examined are depicted.

Figure 2B:
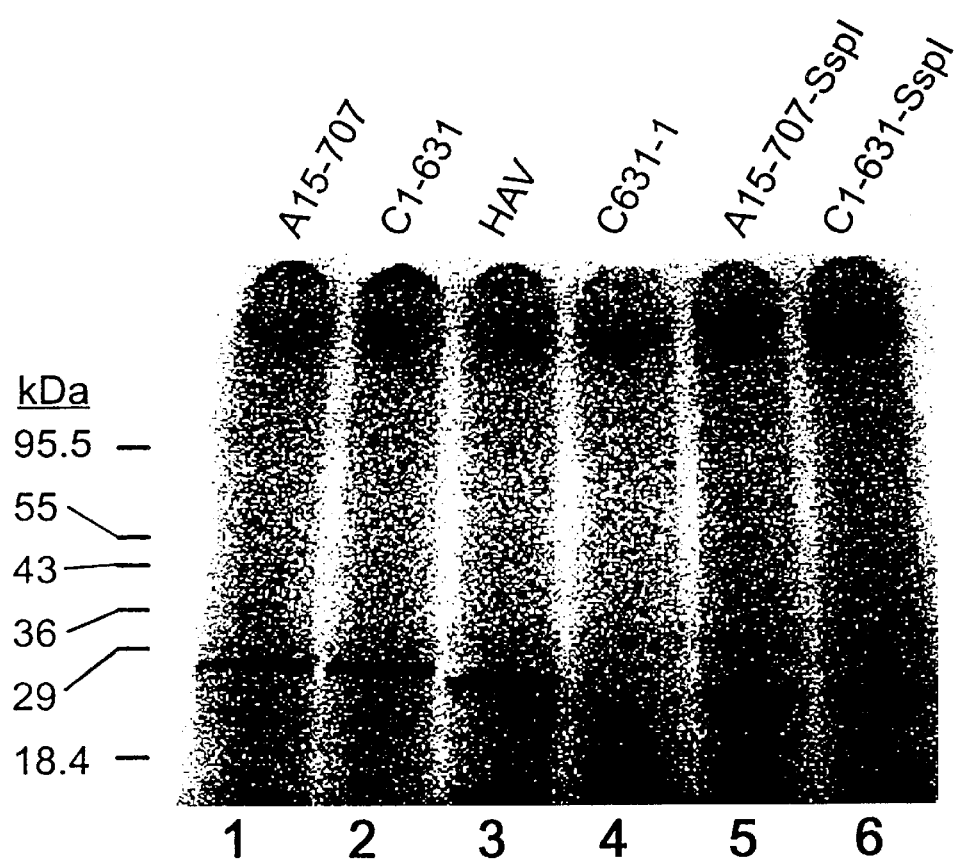
FIG. 2B shows a Phosphorimager scan of products generated by IVTT reactions programmed with pA15-707/CAT (A 15-707, lane 1), pC1-631/CAT (C1-631, lane 2), pHAV-CAT1 (HAV, lane 3), pC631-1/CAT (C631–1, lane 4), SspI-linearized pA15-707/CAT (A15-707-SspI, lane 5) and pC1-631/CAT (C1 -631-SspI, lane 6).

In vitro transcription-translation (IVTT) reactions containing rabbit reticulocyte lysates were programmed with pA15-707/CAT, pC1-631/CAT and a positive control plasmid, pHAV-CAT1, which contained the 5' NTR of hepatitis A virus (HAV) inserted upstream of CAT. All three plasmid DNAs directed the translation of discreet products migrating with somewhat different molecular masses in SDS-PAGE, as shown in FIG. 2B. Referring to the FIG. 2B, the image was generated from a 16 h exposure with a linear range of 7 to 200. GBV-CAT product in lanes 1 and 2 are present at 26 to 27% of the level of the CAT product made from pHAV-CAT1 (lane 3) when the number of Cys residues have been normalized for each product. The products derived from pA15-707/CAT and pC1-631/CAT were slightly larger than that derived from pHAV-CAT1, indicating that translation was initiating upstream of the site of GBV-CAT fusion. In contrast, no product was detected in IVTT reactions programmed with pC631-1/CAT which contained the GBV-C sequences inserted in the antisense orientation relative to CAT. Only the pHAV-CAT1-programmed reaction possessed detectable CAT activity (data not shown). The absence of activity in the products of reactions programmed with pA15-707/CAT and pC1-631/CAT was likely to be due to the misfolding of the CAT protein as a result of its fusion with the N-terminal segment of the GBV polyprotein.

To confirm that the products of the reactions programmed with pA15-707/CAT and pC1-631/CAT were in fact GBV-CAT fusion proteins, the pA15-707/CAT and p1-631/CAT plasmids were digested with SspI prior to being used to program reactions. SspI linearized these plasmids within the CAT coding region so that run-off transcripts produced from these plasmids would lack sequences encoding the C-terminal 45 amino acids of CAT. As expected, reactions programmed with the SspI-digested pA15-707/CAT and pC1-631/CAT DNAs (FIG. 2B, lanes 5 and 6, respectively) contained products that were approximately 5 kDa smaller than those found in reactions programmed with undigested pA15-707/CAT and pC1-631/CAT plasmids (lanes 1 and 2 of FIG. 2B, respectively).

2. Site of Translation Initiation in GBV-A and GBV-C

Figure 3A:
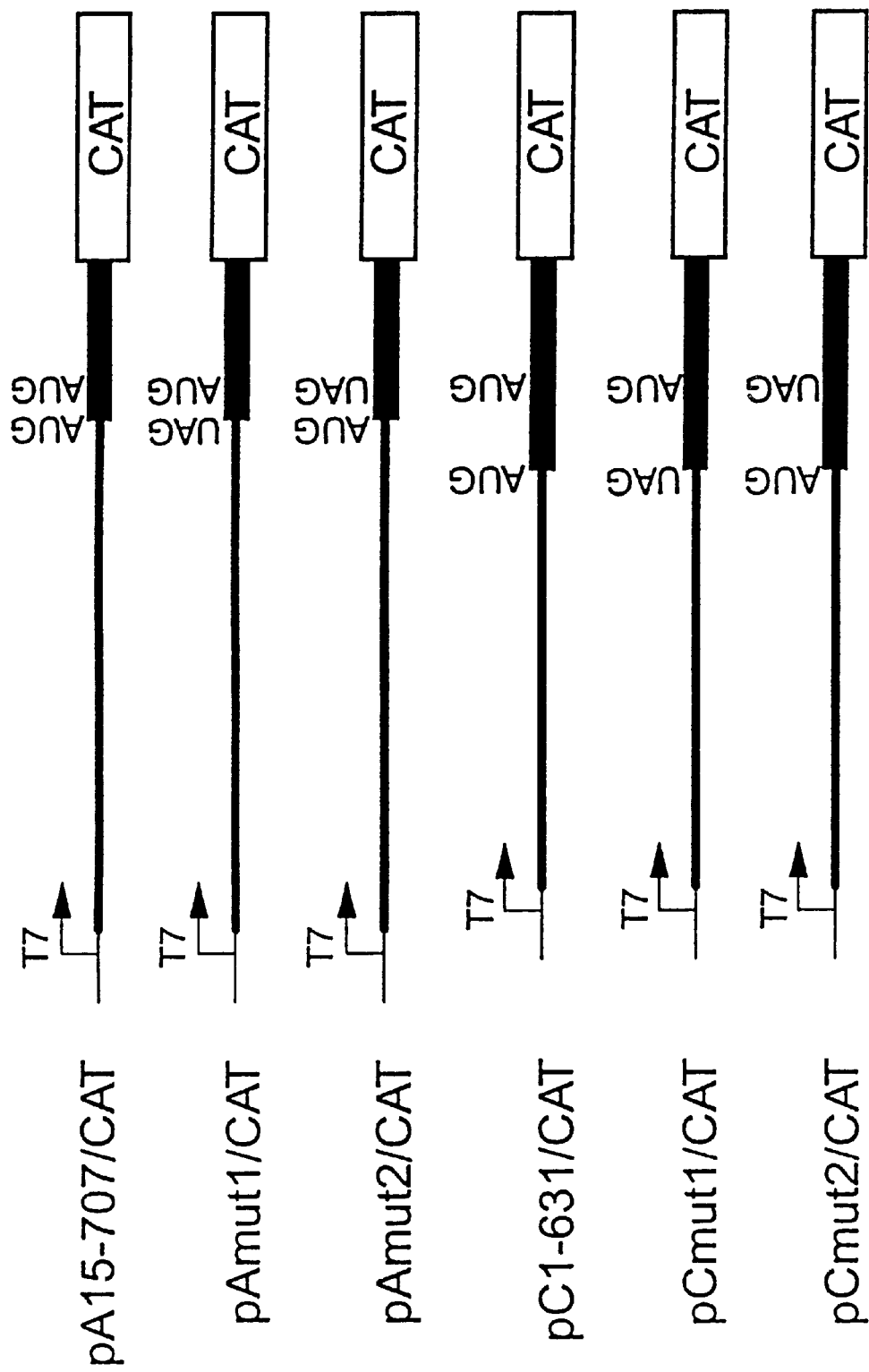
FIG. 3A presents the organization of site-specific mutants of GBV-CAT monocistronic templates.

The apparent molecular masses of the GBV-CAT fusion proteins shown in FIG. 2B suggested possible sites of translation initiation. As indicated in FIG. 1, the GBV-A and GBV-C ORFs that were ligated to CAT in pA15-707/CAT and pC1-631/CAT each contained two in-frame AUG codons that might serve as potential sites of translation initiation within the sequence immediately upstream of CAT. These were the fourth and fifth AUG codons in each of the GBV-A and GBV-C sequences (see FIG. 2A). If initiation occurred at the fourth AUG, the resultant fusion proteins would contain 46 amino acids of GBV-A (adding 5.1 kDa to the 24 kDa of CAT) (SEQUENCE ID NO 30) or 67 amino acids of GBV-C (adding 7.5 kDa to CAT) (SEQUENCE ID NO 31), respectively. In contrast, initiation at the fifth AUG in these transcripts would produce CAT fusion proteins containing 38 and 36 amino acids of GBV-A and GBV-C encoded protein, respectively, adding 4.1 kDa to CAT. The apparent molecular mass of the ~28 kDa fusion proteins detected in the reactions programmed with pA15-707/CAT and pC1-631/CAT suggested that translation initiates at the fifth AUG in each transcript (i.e., the second in-frame Met codons in the long ORF, which are located at nt 594 of the GBV-A sequence [SEQUENCE ID NO 23] and nt 524 of the GBV-C sequence [SEQUENCE ID NO 4]). To identify the sites of translation initiation, the first and second in-frame AUG codons in GBV-A (SEQUENCE ID NO 23) and GBV-C (SEQUENCE ID NO 4)were changed to UAG stop codons producing pAmut1/CAT, pAmut2/CAT, pCmut1/CAT and pCmut2/CAT, as shown in FIG. 3A. These plasmids were used to program IVTT reactions.

Figure 3B:
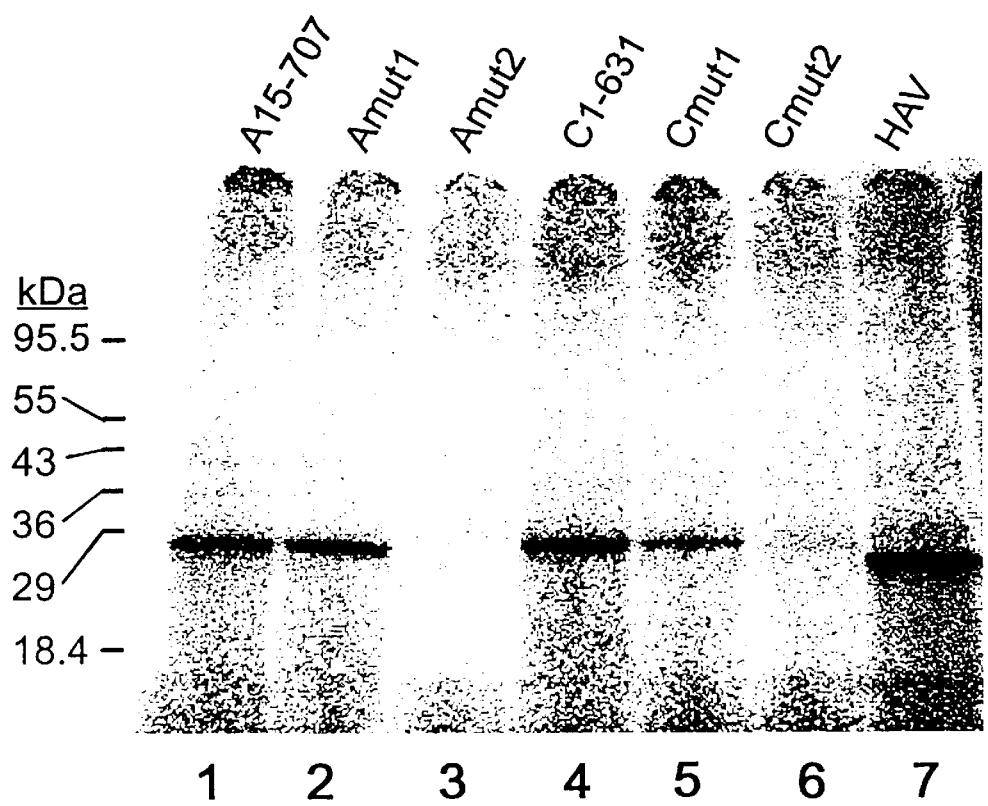
FIG. 3B shows a Phosphorimager scan of IVTT products generated from GBV-CAT mutant templates, wherein Lanes 1, 4 and 7 are control reactions programmed with pA15-707/CAT, pC1-631/CAT and pHAV-CAT1, respectively; products generated from reactions programmed with the mutant templates are found in lanes 2 (pAmut1/CAT), 3 (pAmut2/CAT), 5 (pCmut1/CAT) and 6 (pCmut2/CAT).

GBV-CAT fusion proteins were detected in reactions programmed with pAmut1/CAT and pCmut1/CAT, as shown in FIG. 3B, lanes 2 and 5, respectively). Referring to FIG. 3B, image characteristics are identical to those of FIG. 2B. The GBV-CAT proteins in Lanes 1 and 4 are present at 35 to 41% of the level of CAT produced from pHAV-CAT1 template (lane 7). Amut 1 (lane 2) is 94% of A15-707 (lane 1); Cmut1 (lane 5) is 42% of C1-631 (lane 4). Reactions programmed with pAmut2/CAT and pCmut2/CAT (FIG. 3B, lanes 3 and 6, respectively) did not produce detectable quantities of fusion protein. Thus, because the 28 kDa GBV-CAT protein was detected when the first in-frame AUG codon (nt. 570 in GBV-A [SEQUENCE ID NO 23]

and nt. 431 in GBV-C [SEQUENCE ID NO 4]) was replaced with a stop codon, initiation did not occur at this position. However, mutation of the second in-frame AUG codon (nt. 594 in GBV-A [SEQUENCE ID NO 23] and nt. 524 in GBV-C [SEQUENCE ID NO 4]) completely abrogated protein production directed by these constructs, consistent with the second in-frame AUG being the site of translation initiation in both GBV-A (SEQUENCE ID NO 23) and GBV-C (SEQUENCE ID NO 4). In a related experiment, IVTT reactions programmed with a plasmid containing GBV-C sequence with an AUG to ACG change at the position of the second in-frame AUG (nt 524) produced protein of identical size to pC1-631/CAT, although at a diminished level (data not shown). Because initiation has been found to occur with lower efficiency at ACG codons in other mRNAs (R. Bock et al., *EMBO J* 13:3608–3617 [1994]), these data are consistent with translation of the GBV-C/CAT fusion protein initiating at the ACG codon.

Figure 4B:
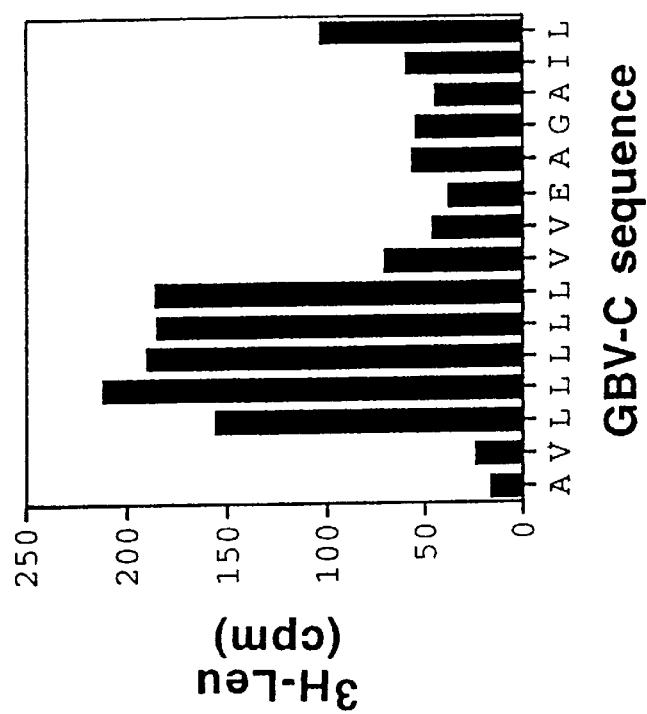
FIGS. 4A AND 4B show an Edman degradation of ³H-Leu-labeled GBV-CAT fusion products, wherein IVTT reactions programmed with pA15-707/CAT are presented in 4A and those programmed with pC1-631/CAT are presented in 4B.
Figure 4A:
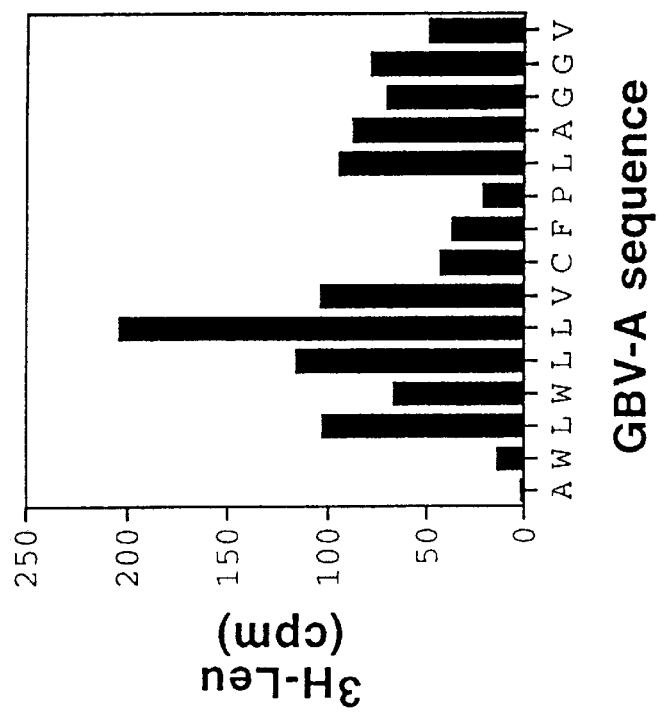

The number and position of Leu residues immediately downstream of the initiator Met in both GBV-A (SEQUENCE ID NO 23) and GBV-C (SEQUENCE ID NO 4) provided a biochemical method to confirm the position of the initiation site in the GBV-CAT fusion proteins. IVTT reactions containing $^3$H-Leu were programmed with pA15-707/CAT and pC1-631/CAT. Reaction products were separated by SDS-PAGE, transferred onto a solid support, and the 28 kDa protein bands were excised. The N-terminal amino acids of the resultant GBV-CAT fusion proteins were sequentially removed by Edman degradation and each fraction was analyzed by scintillation counting. These results are shown in FIGS. 4A and 4B. The $^3$H-Leu profile obtained from the pA15-707/CAT product was consistent with the expected sequence of GBV-A downstream of the second in-frame AUG, as shown in FIG. 4A) assuming that the N-terminal Met residue is removed (see, F. Sherman et al., *Bioessays* 3:27–31 [1985]). Some trailing of the $^3$H signal was noted which may be attributed to incomplete removal of the N-terminal Met. However, for the pC1-631/CAT product, the $^3$H-Leu profile exactly matched the expected amino acid sequence downstream of the second in-frame AUG for GBV-C, as shown in FIG. 4B). Referring to FIG. 4B, CPM following each degradation cycle is plotted above the predicted N-terminal sequences (minus initiator Met) of HGBV-A (SEQUENCE ID NO 30) and GBV-C (SEQUENCE ID NO 31). These experiments thus confirm that translation is initiated at nt 594 of the GBV-A sequence (SEQUENCE ID NO 23) and nt 524 of the GBV-C sequence (SEQUENCE ID NO 4). The relative length of the 5' nontranslated RNA segments and the multiple AUG codons (some of which are in good context for translation initiation) upstream of the authentic initiator AUG in these transcripts both suggest that translation is initiated on these RNAs by internal ribosomal entry, rather than by a conventional 5' scanning mechanism. Thus, we concluded that it is likely that the GBV-A and GBV-C 5' sequences contain an IRES.

Figure 5A:
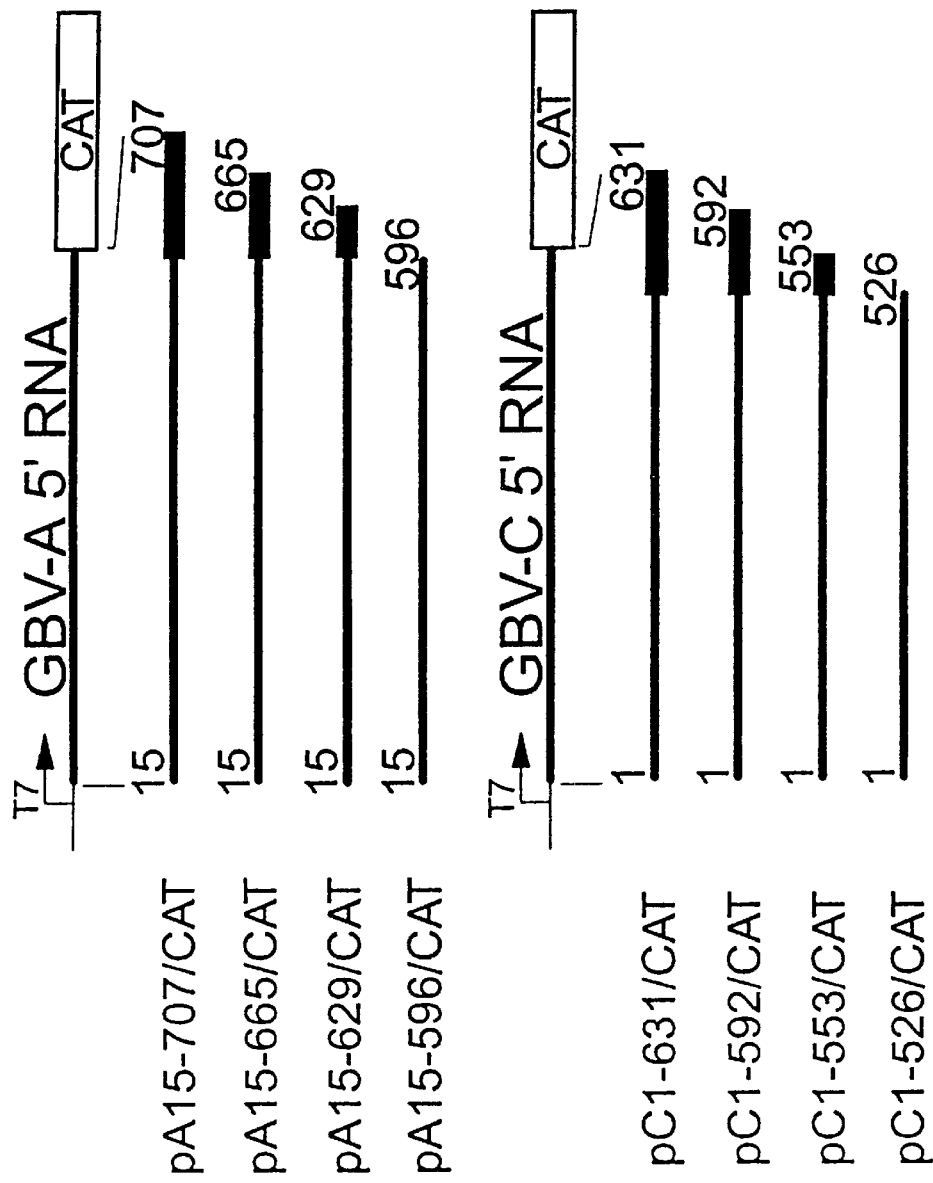
FIGS. 5A and 5B show the translation of monocistronic RNAs containing 3' GBV deletions.
Figure 5B:
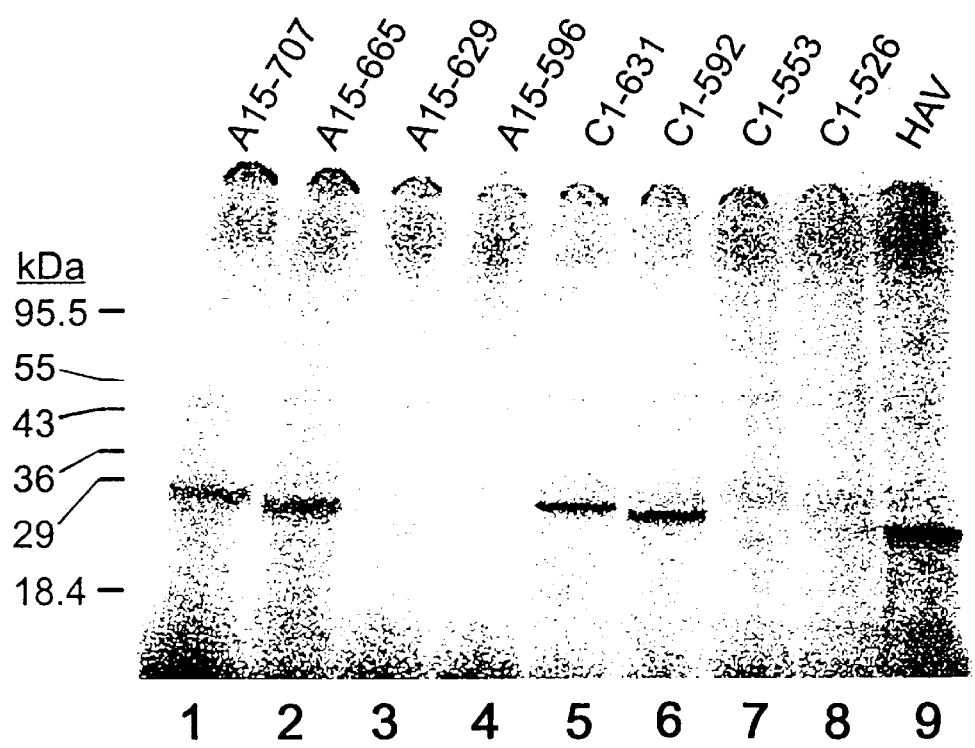

3. GBV Coding Sequence is Required for Efficient Translation of Monocistronic RNAs The results of the in vitro translation reactions described above demonstrated that initiation begins at the Met residue positioned immediately upstream of the putative E1 signal sequence in both pA15-707/CAT and pC1-631/CAT. To determine the 3' limits of the apparent IRES in GBV-A and GBV-C, and whether any amount of GBV sequence is necessary for protein production in the IVTT assays, several 3' deletions were made which reduced the amount of GBV sequence in the GBV-CAT fusion proteins. A schematic of these constructs is shown in FIG. 5A. Protein production was observed in reactions programmed with the deletion constructs pA15-665/CAT and pC1-592/CAT, which encode 72 and 69 nucleotides of the GBV-A (SEQUENCE ID NO 23) and GBV-C (SEQUENCE ID NO 4) coding sequence fused to CAT, respectively, and as shown in FIG. 5B, lanes 2 and 6). Referring to FIG. 5B, image characteristics are identical to those of FIG. 2B. GBV-CAT protein (lanes 1, 2, 5 and 6) is present at 20 to 36% of the level of CAT produced from the pHAV-CAT1 template (lane 9). In contrast, no protein was detected in reactions programmed with the deletion constructs pA15-596/CAT, pC1-526/CAT, pA15-629/CAT or pC1-553/CAT which contain three (pA15-596/CAT, pC1-526/CAT), 36 (pA15-629/CAT) or 30 (pC1-553/CAT) nts of the GBV coding sequence ligated in-frame with CAT. These results demonstrate, rather surprisingly, that sequences downstream of the predicted initiator AUG are necessary for efficient translation initiation in vitro. Given that the authentic initiator codons are in good context in both GBV-A (SEQUENCE ID NO 23) and GBV-C (SEQUENCE ID NO 4), these data provide further evidence that translation is not initiated by a conventional 5' scanning mechanism.

The quantity of CAT produced from the control plasmid, pHAV-CAT1 (seen in FIG. 5B, lane 9), was considerably greater than that produced from either the GBV-A (SEQUENCE ID NO 23) or GBV-C (SEQUENCE ID NO 4) monocistronic constructs. This is of interest, because the HAV IRES has been known to direct the internal initiation of translation with very low efficiency relative to other picornaviral IRES elements (L. E. Whetter et al., J. Virol. 68:5253–5263 [1994]). The low production of GBV-CAT proteins was believed not likely to be due to differences in T7 transcriptional efficiency in these IVTT assays, as similar results were obtained with reactions programmed with equal amounts of RNA (data not shown). Thus, it appears that the level of GBV-CAT protein reflects the extremely low efficiency with which the GBV IRESs direct internal initiation in vitro.

4. Translation of Bicistronic GBV RNAs

Figure 6A:
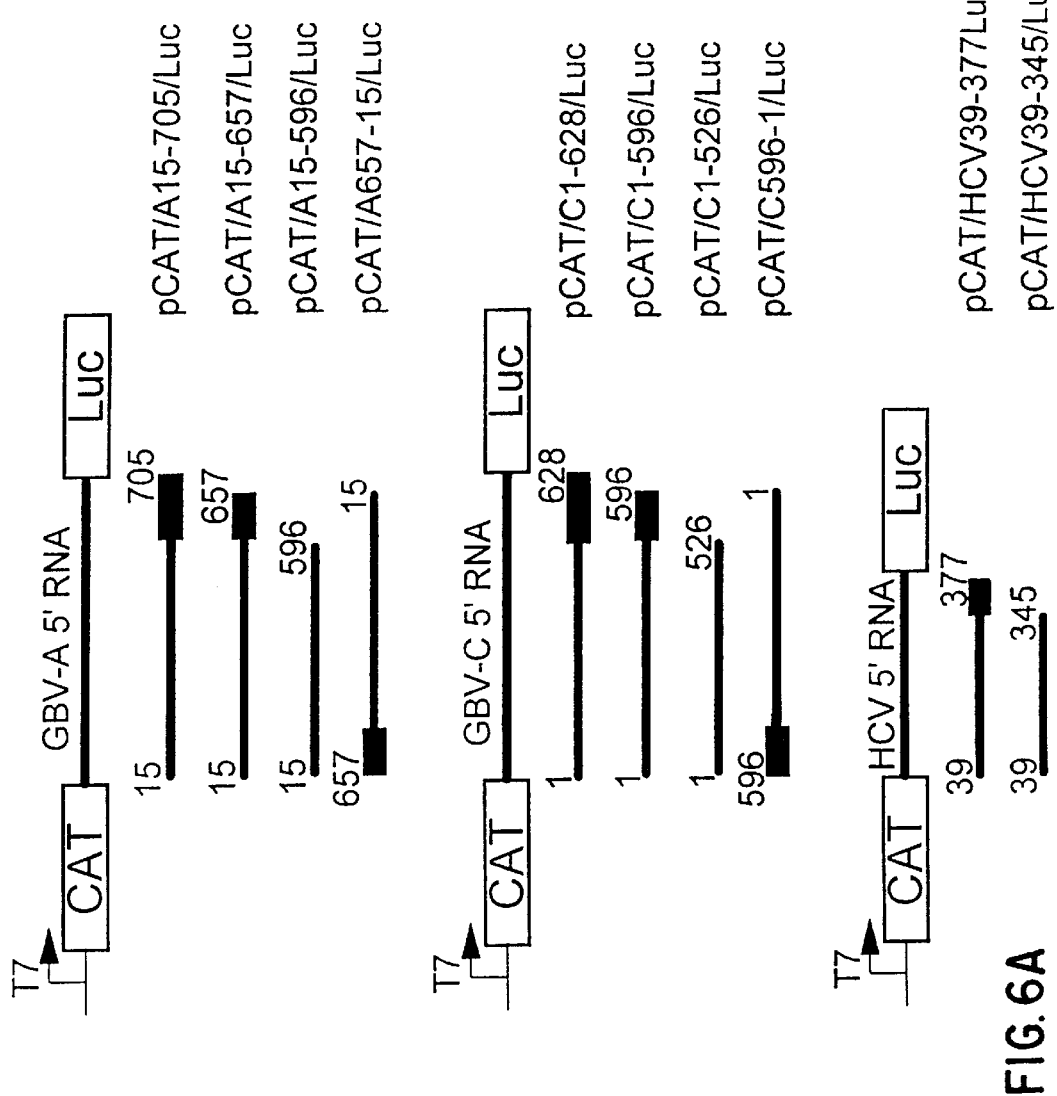
Figure 6B:
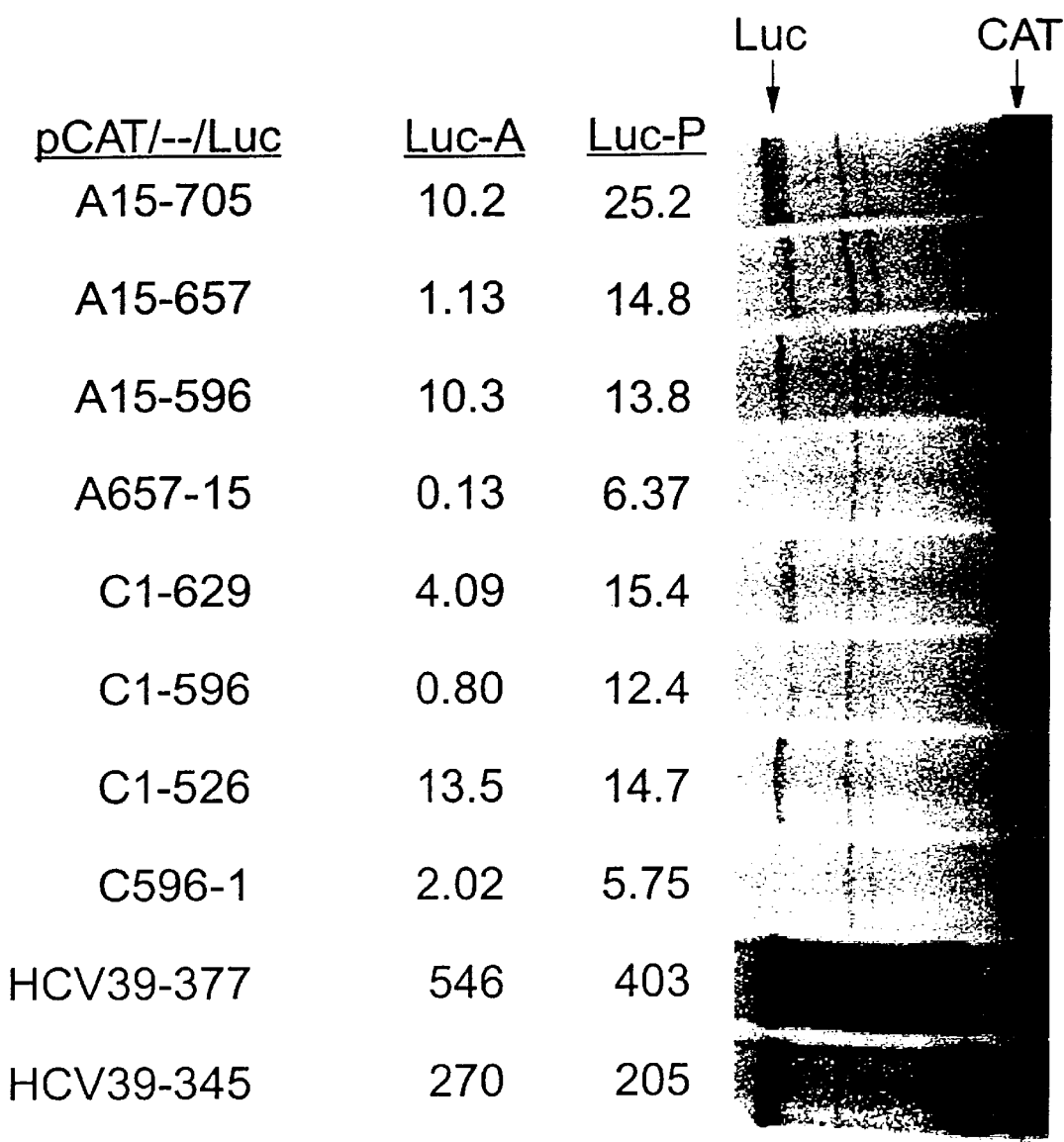

In an effort to formally demonstrate that the 5' RNA sequences of GBV-A and GBV-C contain IRESs, these sequences were inserted between CAT and luciferase (Luc) genes to create bicistronic T7 transcriptional units. These results are graphically shown in FIG. 6A. IVTT reactions programmed with the bicistronic constructs produced equivalent amounts of CAT activity and CAT protein, as shown in FIG. 6B). Referring to FIG. 6B, CAT activity was equivalent in the reactions shown (157,000±3,550 cpm). The PhosphorImager scan was generated from a 72 h exposure with a linear range of 25 to 600. Band volumes are reported in FIG. 6B without background subtraction. This confirmed that essentially equivalent amounts of RNA were being transcribed in each reaction. In contrast, the level of Luc activity and amount of Luc protein produced was dependent on the sequence cloned into the intercistronic space upstream of Luc. Although much less than the level of Luc produced from two positive control plasmids containing the IRES of HCV in the intercistronic space (270,000 to 540,000 light units, FIG. 6B), detectable levels of Luc activity were produced only in reactions programmed with GBV bicistronic constructs containing GBV-A (SEQUENCE ID NO 23) and GBV-C sequences (SEQUENCE ID NO 4) in the sense orientation (10,300 to 13,300 light units, FIG. 6B). Although the quantities of Luc produced were barely detectable by SDS-PAGE, PhosphorImager analysis of these gels indicated that Luc enzymatic activity did not correlate with the protein detected in the IVTT assays (FIG. 6B, Luc-A versus Luc-P). This was most likely due to altered activity as a result of the GBV fusion. Of greater importance, however, was the fact that no detectable protein and only minimal Luc activities (130 and 2020 light units) were produced in reactions programmed with bicistronic constructs containing GBV-A (SEQUENCE ID NO 23) and GBV-C sequences (SEQUENCE ID NO 4) in the antisense orientation. These results suggest that these viruses utilize internal ribosome entry for initiation of translation, but the extraordinarily low activities of the putative GBV IRES elements when placed in a bicistronic context raises a number of issues which are discussed hereinbelow.

5. Secondary Structure of the 5' NTR of GBV-C

Figure 7A:
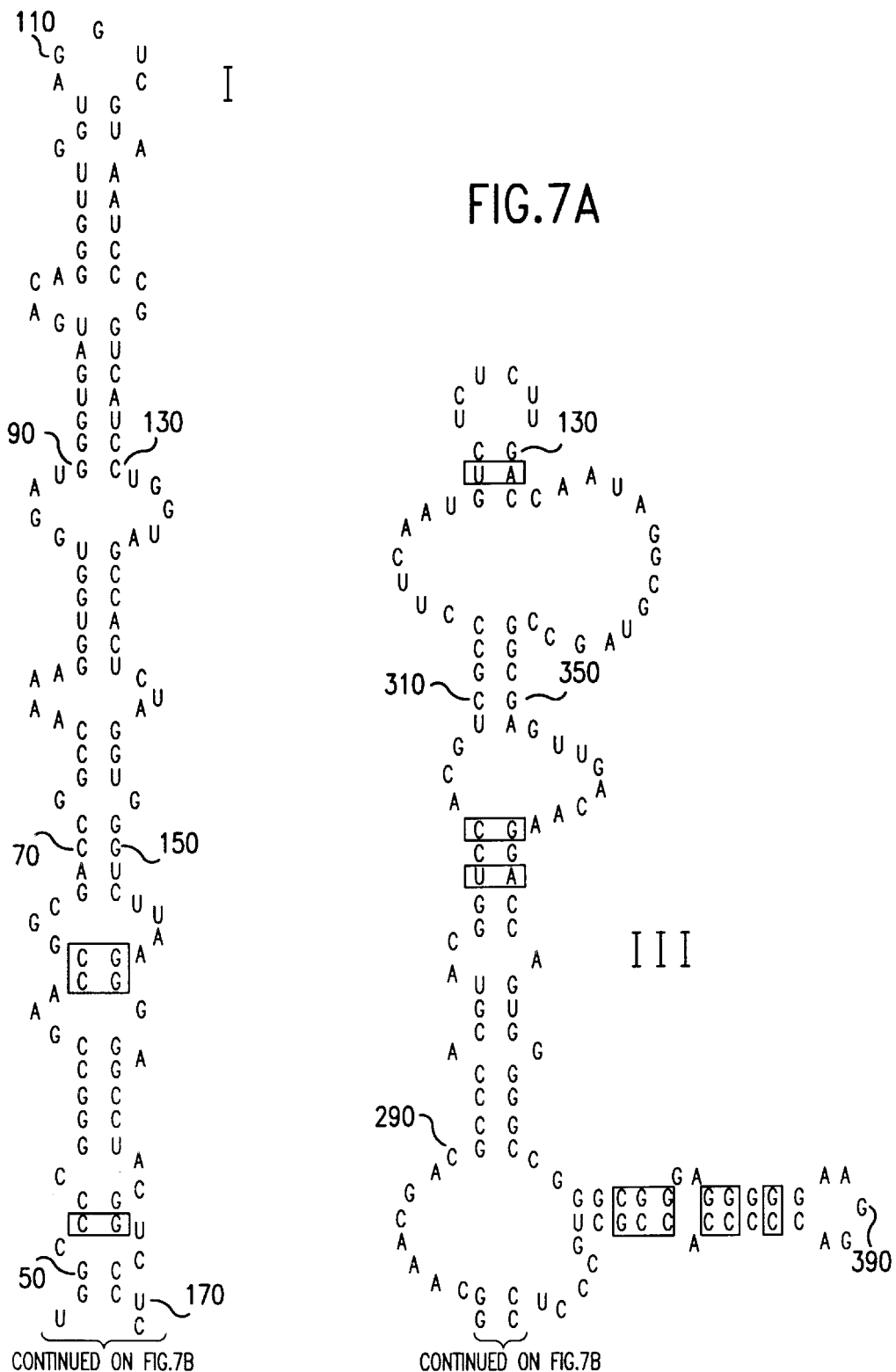
FIG. 7 presents a schematic that depicts a preliminary model of the secondary RNA structures which are present near the 5' end of the GBV-C genome (GenBank accession no. U36380) (SEQUENCE ID NO 3), wherein major putative structural domains are labeled I–V with roman numerals; base pairs which are sites of covariant nucleotide substitutions in different strains of GBV-C are shown in boxes; the putative initiator AUG codon (first in-frame AUG codon which is conserved in all GBV-C sequences) is located between domains IV and V (highlighted bases); (Inset) presents the preliminary model of GBV-A domain V; and covariance between GBV-A and sequences from GBV-A-like viruses found indigenous to tamarins are boxed.
Figure 7B:
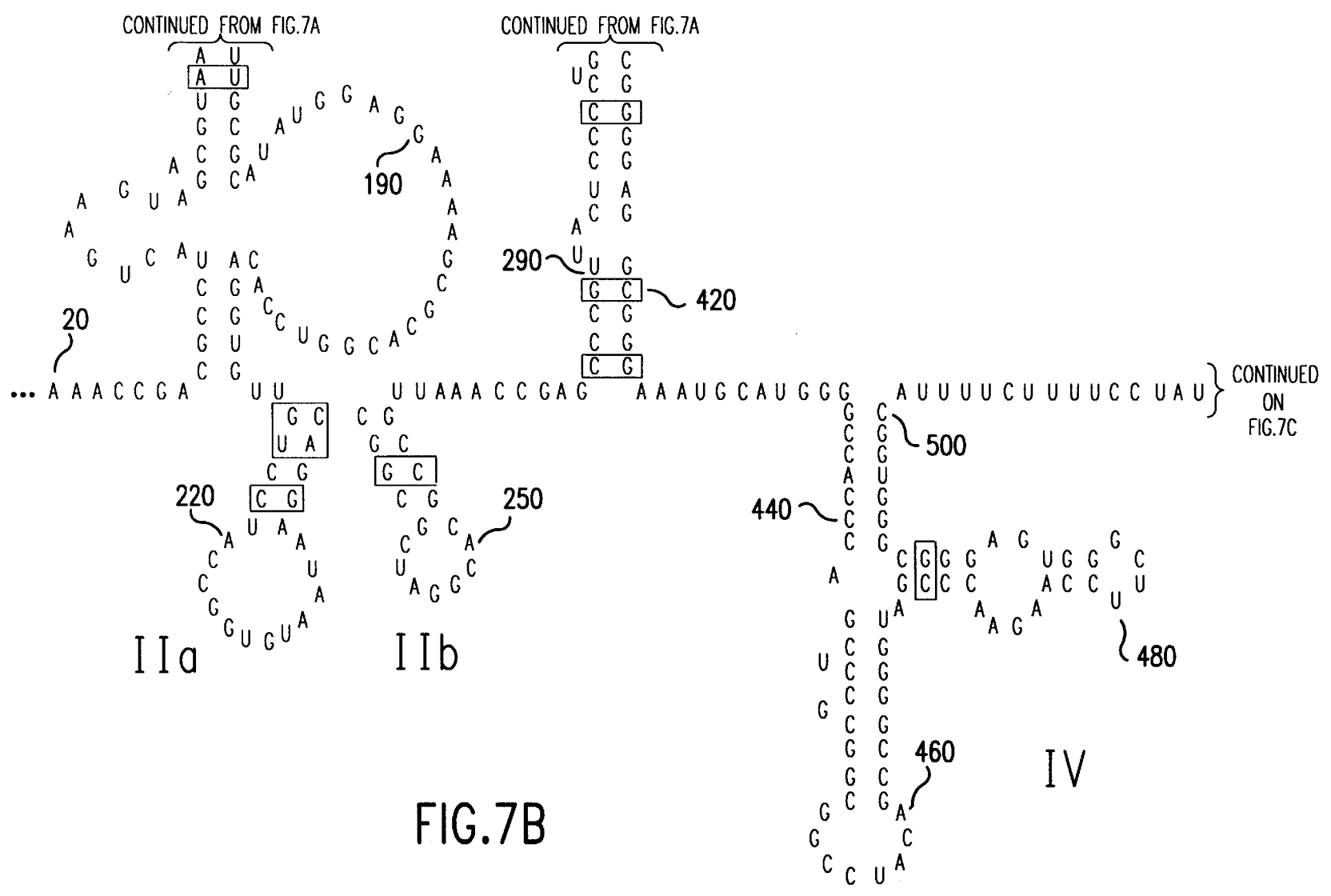
Figure 7D:
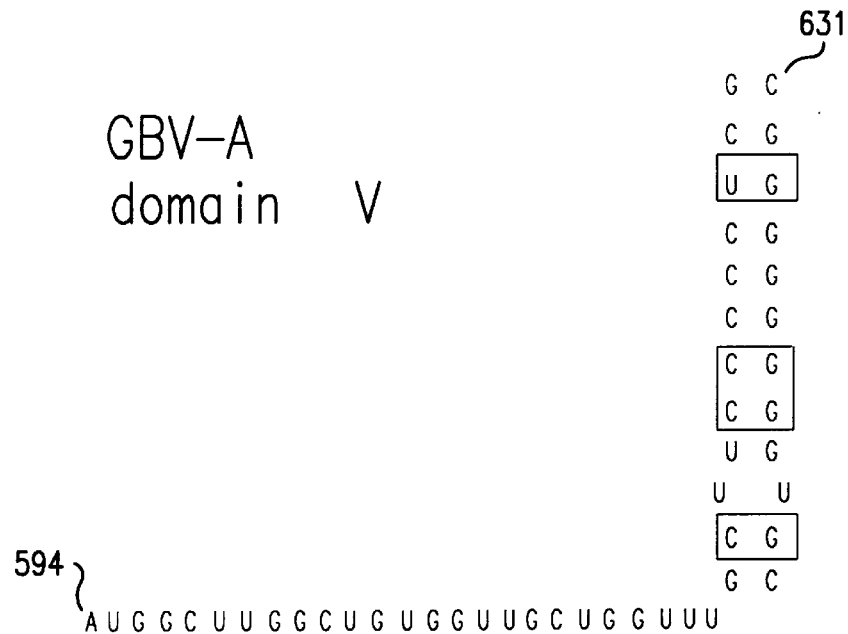
Figure 7C:
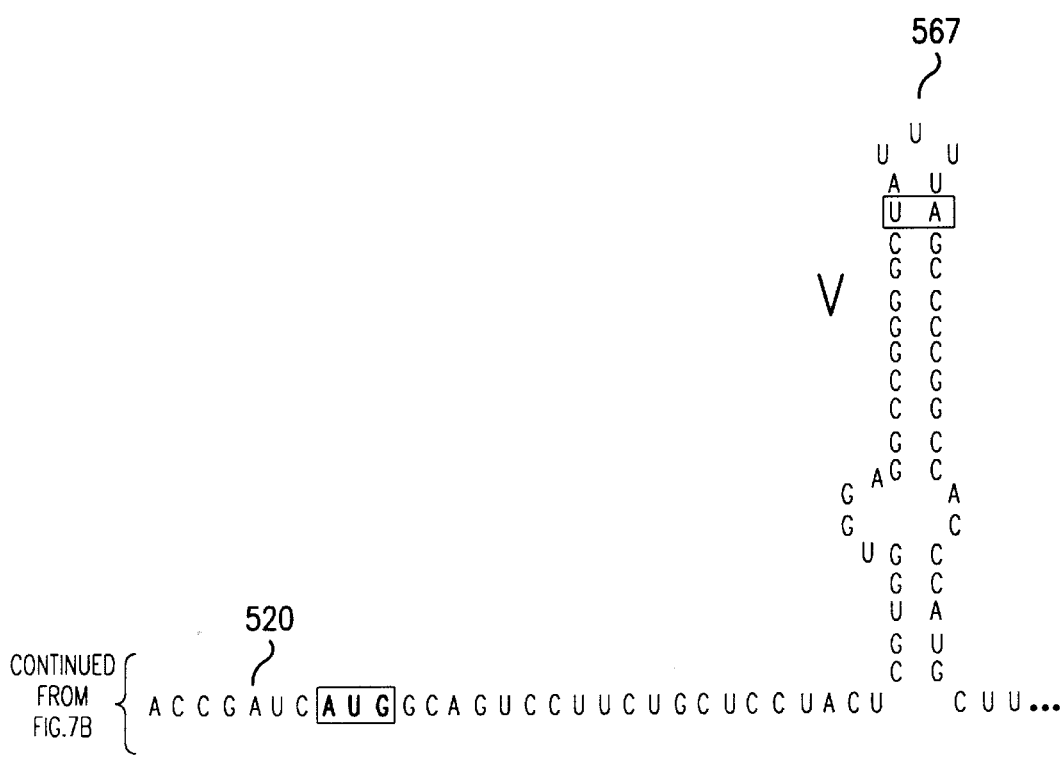

The results presented above suggested that translation of the GBV-A and GBV-C polyproteins is initiated by an unusual mechanism of internal ribosomal entry, which is likely to be controlled by RNA structures within the 5' nontranslated RNA, and which is also dependent upon sequence downstream of the initiator AUG (see FIG. 5). Thus, we attempted to characterize the secondary structure near the 5' end of GBV-C RNA using a combination of phylogenetic analysis and thermodynamic predictions. Covariant nucleotide substitutions indicative of conserved base-pair interactions were identified by manual search of an alignment of 41 different GBV-C sequences. These were used to constrain the folding of the RNA by the computer program, MFOLD. Alternative structures were reviewed to determine which were most permissive for observed variations in the nucleotide sequence, resulting in the model for secondary structure shown in FIG. 7. Referring to FIG. 7, the model structure resulted from a combination of phylogenetic analysis and computational thermodynamic prediction. With minor variation, the structure shown can be assumed by all available known GBV-C sequences. The predicted secondary structure of the 5' NTR of GBV-C is very different from that of HCV (E. A. Brown et al., Nuc. Acid Res. 20:5041–5045 [1992] and M. Honda et al., manuscript submitted) suggesting that the 5' NTRs of these viruses have distinctly different evolutionary histories.

The model suggests that the 5' RNA of GBV-C contains 4 major secondary structure domains upstream of the authentic initiator AUG at nt 524 which is conserved in all GBV-C sequences (domains I–IV in FIG. 7). Domain I consists of an extended stem-loop structure, which is highly conserved in nucleotide sequence between nts 68–152, but which contains several covariant nucleotide substitutions within the flanking RNA segments near its base (FIG. 7, boxed base pairs). The predicted structure of the conserved sequence between nts 68–152 is confirmed by the presence of covariant nucleotide substitutions in alignments of GBV-C with GBV-A, which shares a very similar overall 5' NTR secondary structure (not shown). Domain II contains two small stem-loops (IIa and IIb), both of which are supported by the presence of covariant substitutions in different GBV-C strains. The larger, complex stem-loops which comprise domains III and IV of the model structure are also well supported by covariant substitutions among different GBV-C strains (FIG. 7). Of particular interest, given the requirement for the inclusion of coding sequence for efficient translation of monocistronic GBV transcripts (FIG. 5), is evidence suggesting the existence of a very stable, conserved stem-loop containing 9–10 G-C base-pairs within the ORF, downstream of the putative 5' NTR (see below) (FIG. 7). The existence of this stable helical structure is supported by the presence of a single covariant substitution among different GBV-C strains. This stem-loop appears to be an extension of a larger, well conserved structure (domain V, FIG. 7), located 20 nts downstream of the putative initiator AUG. Importantly, a very similar structure is present near the 5' end of the ORF of GBV-A (FIG. 7, inset).

F. Discussion

Monocistronic mRNAs containing the 5' ends of the GBV-A and GBV-C genomic RNAs fused to CAT directed the production of GBV-CAT fusion proteins in IVTT reactions. Site-specific mutagenesis and Edman degradation of the translation products indicated that translation of these transcripts, and presumably GBV-A and GBV-C genomic RNAs as well, initiates immediately upstream of the putative E1 envelope signal sequence, at the AUG located at nt 594 in GBV-A (SEQUENCE ID NO 23) and nt 524 in the GBV-C sequence (SEQUENCE ID NO 4). The site of initiation identified in GBV-C is corroborated by analysis of the 5' RNA sequences obtained from 35 different GBV-C positive individuals. When these sequences are aligned, the only conserved AUG codon which is in-frame with the GBV-C polyprotein is the AUG at nt 524. Downstream of this AUG codon, nucleotide substitutions in the different GBV-C strains generally result in either silent or conservative amino acid changes. In contrast, upstream of this AUG codon nucleotide substitutions, deletions and insertions drastically change the encoded amino acid sequence in different strains. These data suggest that there is a selective pressure acting downstream of the AUG at nt 524 to maintain a protein coding sequence while no selective pressure exists to maintain such a sequence upstream of this codon.

The fact that translation initiates at the fifth AUG codon in both viral RNAs, many hundreds of nucleotides from the 5' end, is strongly reminiscent of translation in the picornaviruses and HCV, and suggests that translation may be initiated by binding of the 40S ribosomal subunit at an internal site on the RNA. Thus, it seems likely that the 5' NTRs of these viruses may contain an IRES. Because the functional activities of the IRES elements of HCV and the picornaviruses are known to be highly dependent on RNA secondary structure within the 5' NTR, we sought evidence for conserved secondary RNA structures within the 5' NTRs of these viruses. Although the 5' nucleotide sequences of the GBV-C and GBV-A virus genomes have only ~50% nucleotide identity within the 500 nts preceding the initiator AUG of GBV-C, we found the secondary structures of these RNAs to be remarkably similar. Each of the major secondary structural domains shown for GBV-C in FIG. 7 is conserved in the structure of GBV-A with only minimal changes (data not shown). However, both the GBV-A and GBV-C 5' NTR structures are very different from those of the pestiviruses, HCV, and GBV-B, despite the fact that these viruses share a common genome organization as well as multiple sequence motifs within their nonstructural proteins (T. P. Leary et al., supra and A. S. Muerhoff et al., supra). While the 5' NTRs of GBV-B, HCV and the pestiviruses are particularly closely related to each other at the structural level (E. A. Brown et al., supra and M. Honda et al., supra), the prominent domain III pseudoknot and complex stem-loop III structures of these viruses are completely lacking in GBV-C and GBV-A. In addition there is no clear-cut structural relatedness to HCV or the pestiviruses in any of the upstream secondary structures of GBV-A and GBV-C. Thus, similar to the existence of two distinct types of 5' NTR structures among the picornaviruses (one in the cardioviruses, aphthoviruses, and hepatoviruses, and another in the enteroviruses and rhinoviruses [R. J. Jackson et al., Mol. Biol. Reports 19:147–159 {1994}]), there are two distinct types of 5' NTR structures present in the flaviviruses. This has interesting implications for the evolution of these agents.

A prominent feature of the 5' NTR sequences of GBV-C and GBV-A is the presence of a short oligopyrimidine tract located just upstream of the initiator AUG. While this tract is somewhat variable in sequence, it is present in all of the GBV-C sequences and is positioned approximately 21 nts upstream of the initiator AUG. Thus, this region of the 5' NTR bears remarkable similarity to the "box A"/"box B" motif identified at the 3' end of picornaviral 5' NTRs by Pilipenko et al. (E. V. Pilipenki et al., Cell 68:119–131 [1992]), including the distance (20 to 25 nts) between the start of the pyrimidine tract and the first downstream AUG in GBV-C (the initiator AUG), which Pilipenko et al. found to be critical to poliovirus IRES-directed translation. It is interesting that the segment intervening between the oligopyrimidine tract and the first downstream AUG is somewhat shorter in the GBV-A viruses (approximately 17 nts). By analogy with the picornaviruses (Pilipenko et al., supra), this might be expected to result in a preference for initiation of translation at the second in-frame AUG codon in GBV-A (nt +25 with respect to the first AUG). We confirmed this experimentally (see FIG. 4A). The striking differences between the 5' NTR structures of these viruses and that of HCV, coupled with these similarities between the translation of GBV-A and GBV-C and picornaviral 5' NTRs, suggests that the mechanism of translation might be closer to that of picornaviruses than HCV. In HCV, relatively strong evidence supports the concept that the 40S ribosomal subunit binds RNA directly at the site of translation initiation (Honda et al., supra). In contrast, the 40S subunit appears to scan for a variable distance from an upstream primary binding site to the initiator AUG in some picornaviruses (R. J. Jackson et al, supra). Given the variable distances between the authentic initiator codons and the upstream oligopyrimidine tracts in GBV-A and GBV-C, this appears likely to be the case with GBV-A (and possibly also GBV-C).

Both GBV-A and GBV-C contain a very stable stem-loop structure within the translated open reading frame (domain V, FIG. 7.). This conserved structure is located about 20 nts downstream of the initiator AUG in GBV-C, although it is possible that additional, less well conserved base-pair interactions may bring the base of this structure closer to the AUG. It is tempting to speculate that this stem-loop may function to enhance initiation by a scanning 40S ribosomal subunit, much as M. Kozak, Proc. Natl. Acad. Sci USA 87:8301–8305 (1990) has shown that stable stem-loops placed downstream of an AUG can result in a "pausing" of the ribosome over the AUG, enhancing the likelihood of initiation at that codon. This phenomenon may explain why the efficient translation of reporter proteins fused to the 5' NTR requires inclusion of the most 5' sequence of the GBV-C open reading frame. If so, this would provides a novel mechanism by which sequence within the open-reading frame can contribute to regulation of translation in flaviviruses. Both HCV and the GBV-B viruses differ from GBV-A and GBV-C in that their initiator AUG is located within the loop segment of a stem-loop which straddles the 5' end of the open reading frame (M. Honda, supra). Initiation of translation of these viral RNAs is thus dependent upon melting of this stem-loop while, in the case of GBV-A and GBV-C, initiation of translation is likely to be dependent on maintenance of the integrity of the domain V stem-loop.

The domain V stem-loop for which is required for efficient translation of the monocistronic transcripts does not appear to be required for efficient translation in the bicistronic transcripts (compare FIGS. 5 and 6). This apparent discrepancy may be a result of the different reporter genes being utilized in these transcripts. Similar findings have been reported for HCV. Specifically, Reynolds et al., supra, using bicistronic vectors with the IRES-dependent reporter genes secreted alkaline phosphatase or a truncated influenza virus nonstructural protein, show efficient translation directed by the 5' end of HCV requires the inclusion of coding sequences. In contrast, Wang et al., supra, using monocistronic and bicistronic vectors with luciferase as the IRES-dependent reporter gene, find the inclusion of HCV coding sequences is not necessary for efficient translation. Addressing these conflicting results, Reynolds et al., supra, hypothesize that the 5' end of the luciferase gene may complement the function provided by the HCV coding sequences. A similar argument may explain the discordance between the results obtained with the monocistronic GBV-CAT constructs and the bicistronic GBV-Luc constructs.

Although all of these observations suggest the strong likelihood that GBV-A and GBV-C translation is initiated by internal ribosomal entry, only minimal translation of the downstream cistron was noted from bicistronic transcripts containing the 5' NTRs of these viruses in the intercistronic space. Translation directed by the GBV-A and GBV-C 5' NTRs within a bicistronic context was only 2 to 5% that of the HCV IRES in rabbit reticulocyte lysates in vitro (FIG. 6). The very low activities of the GBV-A and GBV-C IRESs suggest several possibilities. First, it is possible that these viruses may in fact have IRES elements with extraordinarily low activity. This is supported by a very low level of translation directed by monocistronic transcripts containing the 5' ends of GBV-A and GBV-C in the in vitro system. Specifically, after adjustment for the number of Cys residues in each construct, GBV-CAT fusion proteins were translated from pA15-707/CAT and pC1-631/CAT transcripts at only 20 to 41% of the level produced by the IRES of HAV. The HAV IRES is known to have very low activity, in the range of 2% of the Sabin poliovirus type I IRES within HAV permissive cells (see, D. E. Schultz et al., J. Virol. 70:1041–1049 [1996] and L. E. Whetter et al., supra). Thus, the low GBV IRES activity noted in vitro may be a true reflection of the strength of these translation elements. Limiting production of viral proteins within an infected host might act to reduce recognition of the infection by the immune system and thus promote viral persistence. Alternatively, it is possible that the low IRES activity detected in reticulocyte lysates reflects a requirement for a specific host cell translation factor which is absent in reticulocyte lysates. The nuclear autoantigen, La, is an example of such a specific cellular factor. It is required for efficient translation directed by the poliovirus IRES, but is not present in sufficient amounts in reticulocyte lysates. K. Meerovitch et al., J. Virol. 67:3798–3807 (1993). It is difficult to comment more specifically on this possibility, since the cellular tropisms of GBV-A and GBV-C are unknown. Yet a third possibility is that the low translational activity of the GBV-A and GBV-C 5' NTRs may reflect a requirement for additional, yet to be identified 5' viral sequences that may be present in these viral genomes. It is also conceivable that translation is initiated by a mechanism distinct from both the classic 5' scanning and IRES-directed translation initiation mechanism. For example, relatively efficient translation initiation at an internal site in monocistronic transcripts but low translational activity in the bicistronic context could be explained by a mechanism involving "ribosome shunting" (J. Fütterer et al., Cell 73:789–802 [1993]) following recognition of the 5' end of the RNA by the 40S ribosome subunit. Further studies will be required to distinguish between these different possibilities.

The proteins located at or near the amino termini of the polyproteins of yellow fever virus (protein C), a flavivirus, bovine viral diarrhea virus, a pestivirus, and HCV (core) are small and highly basic (Q.-L. Choo et al., *Proc. Natl. Acad. Sci. USA* 88:2451–2455 [1991]; M. S. Collett et al., supra; R. H. Miller et al., *Proc. Natl. Acad. Sci. USA* 87:2057–2061 [1990]). Because GBV-A and GBV-C are phylogenetically related to these viruses (12, 18) it was expected that such a protein would be encoded in these viruses. However, the position of the initiation codons in GBV-A and GBV-C eliminates the possibility of a basic core protein being located at the N-termini of the viral polyproteins. The possibility that the core coding sequences may have been deleted during RT-PCR amplification or cloning of the 5' ends of GBV-A and GBV-C is unlikely for several reasons. First, identical deletions would have had to occur consistently in each of the several clones generated during the sequencing of GBV-A and GBV-C, in addition to the 42 separate GBV-C isolates described by U.S. Ser. No. 08/580, 038, filed Dec. 21, 1995 and previously incorporated herein by reference, and the 2 HGV isolates described by Linnen et al., supra. This consistency, in addition to the correspondence between PCR and infective titers for GBV-A (G. G. Schlauder et al., *J. Med. Virol.* 46:81–90 [1995] and J. N. Simons, *Proc. Natl. Acad. Sci USA*, supra), argues against GBV-A and GBV-C sequences being derived from defective interfering particles in the cloning sources. Second, the deletion of core sequences would have had to occur without disturbing the translational activity of the 5' ends of these viruses. But because proper initiation requires sequences located in the coding regions of GBV-A and GBV-C, the coupling between the translational activity and the coding regions appear to make this an impossibility. Finally, several RT-PCR experiments using different virus isolates, different primer combinations, and different RT-PCR conditions and polymerases provide no evidence for additional virus sequence (data not shown).

The lack of a core-like protein at the N-terminus of the viral polyprotein distinguishes GBV-A and GBV-C from all other members of the Flaviviridae. In fact, searches of all six potential reading frames of the three full length GBV-C sequences (T. P. Leary et al., supra and L. Linnen et al., supra) or the GBV-A sequence (SEQUENCE ID NO. 23) present in GenBank does not reveal a conserved open reading frame encoding a core-like protein. Thus, these viruses appear distinct from enveloped viruses in general as they do not appear to encode a basic protein which mediates the packaging of the viral nucleic acid into the virion envelope. Core-less infectious particles have been generated artificially using the vesicular somatitis virus glycoprotein. M. M. Rolls et al., *Cell* 79:497–506 (1994). Thus, it is possible that GBV-A and GBV-C may be truly "core-less" enveloped viruses. However, it is possible that a cellular RNA-binding protein has been appropriated by these viruses to facilitates the specific and efficient packaging of the virion RNA into the envelope. Whether GBV-A and GBV-C contain core proteins and the source of these cores awaits the biochemical characterization of these viruses.

The present invention is intended to be limited only by the appended claims.

What is claimed is:

1. A method for altering the translation of a hepatitis GB virus (HGBV) nucleic acid(s) to an HGBV protein(s) in vitro, comprising:

(a) hybridizing a non-naturally occurring nucleic acid sequence to a sequence of the sense strand within the 5' non-translated region (NTR) of HGBV-A, HGBV-B or HGBV-C wherein said nucleic acid sequence has at least 10 nucleotides and is complementary to said 5' NTR region of HGBV-A, HGBV-B or HGBV-C; and (b) translating said sequence of said sense strand.

2. The method of claim 1 wherein said non-naturally occurring nucleic acid sequence is an antisense nucleic acid sequence.

3. The method of claim 1 wherein said non-naturally occurring nucleic acid sequence is a nucleic acid analog.

4. The method of claim 3 wherein said nucleic acid analog is selected from the group consisting of a morpholino compound, a peptide nucleic acid analog and a phosphorothioate nucleic acid analog.

5. A method of enhancing the translation of a first nucleic acid in vitro comprising:

(a) forming a combined nucleic acid by operably linking said first nucleic acid with a second nucleic acid having a sequence of the HGBV-A, HGBV-B or HGBV-C 5' NTR region, wherein said second nucleic acid controls translation of said first nucleic acid; and (b) translating said combined nucleic acid.

* * * * *